United States Patent
Singh et al.

(10) Patent No.: US 12,318,357 B2
(45) Date of Patent: Jun. 3, 2025

(54) SMALL MOLECULE DRUGS AND RELATED METHODS FOR TREATMENT OF DISEASES RELATED TO TDP-43, ALPHA-SYNUCLEIN, HUNTINGTIN'S PROTEIN AND TAU PROTEIN OLIGOMER FORMATION

(71) Applicant: ACELOT, INC., Palo Alto, CA (US)

(72) Inventors: Ambuj K. Singh, Santa Barbara, CA (US); Christian A. Lang, Santa Barbara, CA (US)

(73) Assignee: ACELOT, INC., South San Francisco, CA (US)

( * ) Notice: Subject to any disclaimer, the term of this patent is extended or adjusted under 35 U.S.C. 154(b) by 130 days.

(21) Appl. No.: 16/873,866

(22) Filed: Jul. 31, 2020

(65) Prior Publication Data

US 2021/0052519 A1    Feb. 25, 2021

Related U.S. Application Data

(60) Provisional application No. 62/922,316, filed on Aug. 2, 2019.

(51) Int. Cl.
| | |
|---|---|
| A61P 25/16 | (2006.01) |
| A61K 31/137 | (2006.01) |
| A61K 31/167 | (2006.01) |
| A61K 31/277 | (2006.01) |
| A61K 31/357 | (2006.01) |
| A61K 31/40 | (2006.01) |
| A61K 31/452 | (2006.01) |
| A61K 31/495 | (2006.01) |
| A61K 31/5375 | (2006.01) |
| A61P 25/28 | (2006.01) |

(52) U.S. Cl.
CPC .......... *A61K 31/137* (2013.01); *A61K 31/167* (2013.01); *A61K 31/277* (2013.01); *A61K 31/357* (2013.01); *A61K 31/40* (2013.01); *A61K 31/452* (2013.01); *A61K 31/495* (2013.01); *A61K 31/5375* (2013.01)

(58) Field of Classification Search
CPC .. A61K 31/167; A61K 31/137; A61K 31/277; A61K 31/357; A61P 21/00; A61P 25/14; A61P 25/16; A61P 25/28
See application file for complete search history.

(56) References Cited

U.S. PATENT DOCUMENTS

| | | | |
|---|---|---|---|
| 4,175,136 A | 11/1979 | Nedelec et al. | |
| 9,175,094 B2 | 11/2015 | Pfeifer et al. | |
| 9,938,263 B2* | 4/2018 | Tanzi ................... | C07D 487/04 |
| 10,220,011 B2 | 3/2019 | Boudes et al. | |
| 10,301,381 B2 | 5/2019 | Weihofen et al. | |
| 2005/0272722 A1 | 12/2005 | Lansbury et al. | |
| 2009/0069432 A1 | 3/2009 | Snow et al. | |
| 2013/0274260 A1 | 10/2013 | Griffioen et al. | |
| 2018/0222899 A1 | 8/2018 | Wrasidlo et al. | |
| 2020/0223788 A1* | 7/2020 | Singh ................... | C07D 207/06 |

FOREIGN PATENT DOCUMENTS

| | | | |
|---|---|---|---|
| AU | 2006230674 A1 | 11/2006 | |
| JP | 2014-196269 A | 10/2014 | |
| WO | WO-2006101454 A1 * | 9/2006 | .............. A61P 29/00 |
| WO | WO-2008/154083 | 12/2008 | |
| WO | WO-2010/015040 A1 | 2/2010 | |
| WO | WO-2014/207240 A1 | 12/2014 | |
| WO | WO 2019/089066 A1 | 5/2019 | |
| WO | WO-2021/025723 A1 | 2/2021 | |

OTHER PUBLICATIONS

Bryson et al. (Human Molecular Genetics, 2012, vol. 21, No. 17 3871-3882. doi: 10.1093/hmg/dds215. Advance Access published on Jun. 7, 2012.) (Year: 2012).*
Dick RM (2011). "Chapter 2. Pharmacodynamics: The Study of Drug Action". In Ouellette R, Joyce JA. Pharmacology for Nurse Anesthesiology. Jones & Bartlett Learning:pp. 17-26. (Year: 2011).*
J. G. Cannon Chapter Nineteen in Burger's Medicinal Chemistry and Drug Discovery, Fifth Edition, vol. I: Principles and Practice, Wiley-Interscience 1995, pp. 783-802, 784. (Year: 1995).*
Li et al. (Aging Cell (2006) 5, pp. 153-165. https://doi.org/10.1111/j.1474-9726.2006.00200.x) (Year: 2006).*
Prasad et al, "Molecular Mechanisms of TDP-43 Misfolding and Pathology in Anyotrophic ... " Frontiers in Molecular Neuroscience (2019) vol. 12 pp. 1-36.
Downey, M.A. et al. (Jan. 2019). "Inhibiting and Remodeling Toxic Amyloid-Beta Oligomer Formation Using a Computationally Designed Drug Molecule That Targets Alzheimer's Disease," *Journal of the American Society for Mass Spectrometry* 30(1):85-93.
Dedeoglu, A. et al. (Oct. 15, 2002). "Therapeutic effects of cystamine in a murine model of Huntington's disease," *The Journal of Neuroscience* 22(20):8942-8950.
Extended European Search Report mailed on Jul. 25, 2023, for EP Patent Application No. 20849202.5, 29 pages.
Karpuj, M.V. et al. (Feb. 2002). "Prolonged survival and decreased abnormal movements in transgenic model of Huntington disease, with administration of the transglutaminase inhibitor cystamine," *Nature Medicine* 8(2):143-149.

(Continued)

*Primary Examiner* — Amanda L. Aguirre
*Assistant Examiner* — Chris E Simmons
(74) *Attorney, Agent, or Firm* — MINTZ, LEVIN, COHN, FERRIS, GLOVSKY AND POPEO, P.C.

(57) ABSTRACT

The present invention provides small molecule drugs and pharmaceutical compositions for the treatment and prevention of diseases related to the formation of certain types of oligomers in a subject. More specifically, the drugs and compositions reduce or prevent the formation of oligomers formed from tau protein, TDP-43, Huntingtin's protein and/or alpha-synuclein. It further provides a method of reducing formation of or disrupting TDP-43, alpha-synuclein, Huntingtin's protein and/or tau protein oligomers in a subject, the method comprising the step of administering to the subject in need thereof a therapeutically effective amount of a pharmaceutical composition.

5 Claims, 50 Drawing Sheets

(56) References Cited

OTHER PUBLICATIONS

Tanaka, M. et al. (May 1, 2005). "A novel therapeutic strategy for polyglutamine diseases by stabilizing aggregation-prone proteins with small molecules," *Journal of Molecular Medicine* 83(5):343-352.

Calingasan, N.Y. et al. (2005). "β-amyloid 42 accumulation in the lumbar spinal cord motor neurons of amyotrophic lateral sclerosis patients," *Neurobiol Dis* 19:340-347.

Jamali, A.M. et al. (Aug. 2023). "PET and SPECT Imaging of ALS: An Educational Review," *Molecular Imaging* 2023:5864391.

Koistinen, H. et al. (Oct. 2006). "Elevated levels of amyloid precursor protein in muscle of patients with amyotrophic lateral sclerosis and a mouse model of the disease," *Muscle Nerve* 34(4):444-450.

Matías-Guiu, J.A. et al. (Jun. 4, 2016). "Amyloid- and FDG-PET imaging in amyotrophic lateral sclerosis," *Eur J Nucl Med Mol Imaging* 43:2050-2060.

\* cited by examiner

| # | Structure | $MolName | EC50 |
|---|-----------|----------|------|
| 1 | 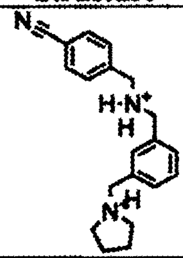 | AC0107 | 0.45 |
| 2 | 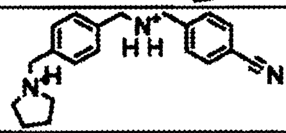 | AC0105 | 0.51 |
| 3 | 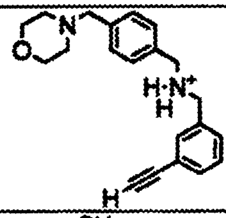 | AC0104 | 0.7 |
| 4 | 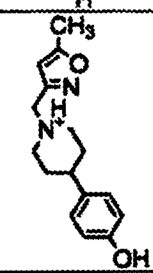 | AC0106 | 1 |
| 5 | 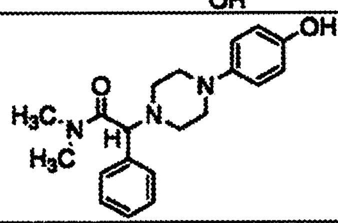 | AC0103 | 1.3 |
| 6 | 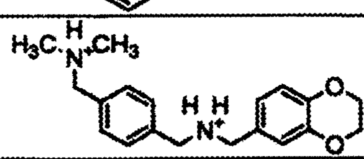 | AC0102 | 3.5 |
| 7 | 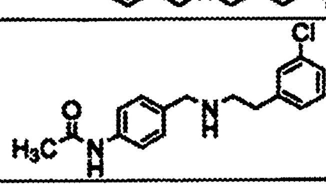 | AC0101 | 3.9 |

112

114

116

118

120

122

136

138

140

142

144

146

148

150

152

154

156

158

160

162

164

166

168

170

172

174

176

178

180

182

184

186

188

190

192

194

196

198

200

202

204

206

208

210

212

214

216

218

Z3059201471 (Benzald1)

Z3059201528

Z3059201486

Z3059201535

Z3059201492

Z30592201542

Z3059201512 (Fluorophenyl)

Z90525960 (Dimethoxy)

Z3059201521 (Aminofluorophenyl)

Z2181805484

Prod2

Prod3

Prod1

Prod46

Prod79

Prod88

Prod8

Prod28

Prod42

Prod43

Prod51

Prod84

Prod59

Prod72

Prod50

Prod7

Prod73

Prod76

Prod33

Prod87

Prod29

SCHEME I

SCHEME II

SCHEME III

SCHEME 4

SCHEME 5

SCHEME 6

SCHEME 7

SCHEME 8

SCHEME 9

SCHEME 10

Benzald1

Fluorophenyl

Aminofluorphenyl

Dimethoxy

Verapamil

Dobutamine

| No. | Structure | Amount delivered, g | Purity, % | Comments |
|---|---|---|---|---|
| Z3059201471<br>AC0201 | 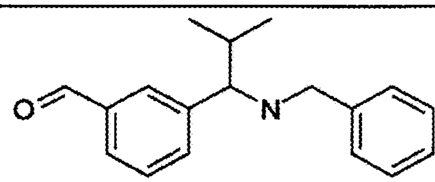 | 0.012 | 95 | - |
| Z3059201512<br>AC0202 | 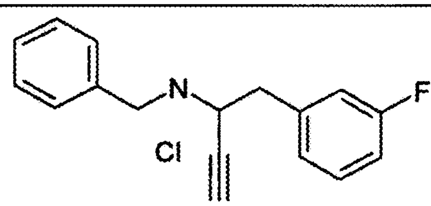 | 0.015 | 95 | - |
| Z3059201521<br>AC0203 | 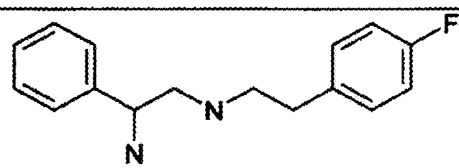 | 0.01 | 95 | - |
| Z90525960<br>AC0204 | 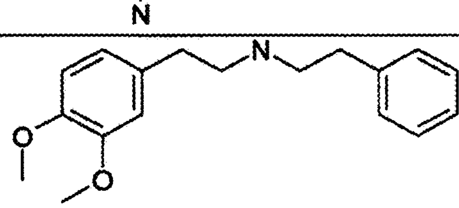 | 0.01 | 95 | - |

SMALL MOLECULE DRUGS AND RELATED METHODS FOR TREATMENT OF DISEASES RELATED TO TDP-43, ALPHA-SYNUCLEIN, HUNTINGTIN'S PROTEIN AND TAU PROTEIN OLIGOMER FORMATION

CROSS-REFERENCES TO RELATED APPLICATIONS

This application claims priority from U.S. Provisional Patent Appl. No. 62/922,316, filed Aug. 2, 2019, entitled, "SMALL MOLECULE DRUGS AND RELATED METHODS FOR TREATMENT OF DISEASES RELATED TO TDP-43, ALPHA-SYNUCLEIN, HUNTINGTIN'S PROTEIN AND TAU PROTEIN OLIGOMER FORMATION," which is hereby incorporated by reference into this application in its entirety.

This invention was made with Government support under NSF SBIR Phase I Award #1143484 entitled, "Identifying Drug Leads Via 3D Pharmacophore Space Analysis".

FIELD OF THE INVENTION

The present invention provides small molecule drugs and pharmaceutical compositions for the treatment and prevention of diseases, typically neurodegenerative diseases such as Alzheimer's, related to the formation of certain types of oligomers in a subject. More specifically, the drugs and compositions reduce or prevent the formation of oligomers formed from Tau protein, TDP-43, alpha-synuclein and/or Huntingtin Protein.

BACKGROUND OF THE INVENTION

There have been reports of compounds and compositions that interact with tau protein, TDP-43, alpha-synuclein, Huntingtin protein and related oligomers. U.S. Pat. No. 10,220,011, entitled "TDP-43-binding polypeptides useful for the treatment of neurodegenerative diseases" is allegedly directed to the following: "Provided herein are antigen-binding constructs such as antibodies that bind to the RRM-1 domain of TDP-43. The antigen-binding constructs are capable of blocking the interaction of TDP-43 with NF-kappa-B in cells. Also provided herein are method of using the antigen-binding constructs in the treatment of diseases associated with TPD-43 proteinopathy, such as amyotrophic lateral sclerosis (ALS), frontotemperal lobar degeneration (FTLD), Lewy body disease and motor neuron disease." Abstract.

U.S. Pat. No. 10,301,381, entitled "Anti-alpha synuclein binding molecules" is allegedly directed to the following: "Provided are anti-human alpha-synuclein-specific binding molecules, e.g., antibodies or antigen-binding fragments, variants or derivatives thereof, as methods related thereto. Further provided are anti-human alpha-synuclein binding molecules which bind to specific N-terminal and C-terminal epitopes on human alpha-synuclein. The binding molecules described herein can be used in pharmaceutical and diagnostic compositions for alpha-synuclein targeted immunotherapy and diagnosis, respectively." Abstract.

U.S. Pat. No. 9,175,094, entitled "Monoclonal antibody" is allegedly directed to the following: "The present invention is related to methods and compositions for the therapeutic and diagnostic use in the treatment of diseases and disorders which are caused by or associated with amyloid or amyloid-like proteins including amyloidosis, a group of disorders and abnormalities associated with amyloid protein such as Alzheimer's disease. The present invention provides novel methods and compositions comprising highly specific and highly effective antibodies having the ability to specifically recognize and bind to specific epitopes from a range of beta-amyloid proteins. The antibodies enabled by the teaching of the present invention are particularly useful for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD)." Abstract.

Despite the various reports, there is still a need for novel compounds, compositions and methods for the treatment of diseases associated with the formation of tau protein, TDP-43, alpha synuclein and Huntingtin protein oligomers.

SUMMARY OF THE INVENTION

In one aspect, the present invention provides a method of reducing formation of or disrupting TDP-43, alpha-synuclein, tau protein and/or Huntingtin protein oligomers in a subject, the method comprising the step of administering to the subject in need thereof a therapeutically effective amount of a pharmaceutical composition comprising a compound selected from the group consisting of AC0101, AC0102, AC0103, AC0104, AC0105, AC0106, AC0107, AC0201, AC0202, AC0203 and AC0204.

In another aspect, administration of the pharmaceutical composition results in improved or enhanced movement in a subject with decreased movement. In another embodiment, the subject is diagnosed with ALS or is at risk for developing ALS.

In another aspect, the compound administered for reducing formation of or disrupting TDP-43, alpha-synuclein, tau protein and/or Huntingtin protein oligomers in a subject is N-[4-({[2-(3-chlorophenyl)ethyl]amino}methyl)-phenyl] acetamide (AC0101); (2,3-dihydro-1,4-benzodioxin-6-ylmethyl)({4 [(dimethylamino)-methyl]phenyl}methyl)amine (AC0102); 2-[4-(4-hydroxyphenyl) piperazin-1-yl]-N,N-dimethyl-2 phenylacetamide (AC0103); 3-[({[4-(morpholin-4 ylmethyl)phenyl]methyl}amino)-methyl]benzonitrile (AC0104); 4-({[3-(1-pyrrolidinylmethyl)benzyl]amino}methyl)benzonitrile (AC0105); 4-{1-[(5-methyl-1,2-oxazol-3-yl)methyl]-1,2,3,6 tetrahydropyridin-4-yl}phenol (AC0106); 4-[({[3-(pyrrolidin-1-ylmethyl)phenyl] methyl}amino)methyl]benzonitrile (AC0107); AC0201; AC0202; AC0203; and AC0204.

In another aspect, the present invention provides a method of reducing formation of or disrupting TDP-43, alpha-synuclein, tau protein and/or Huntingtin protein oligomers in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224 (which are shown in FIGS. 9-29).

DETAILED DESCRIPTION OF THE INVENTION

Figure 1:
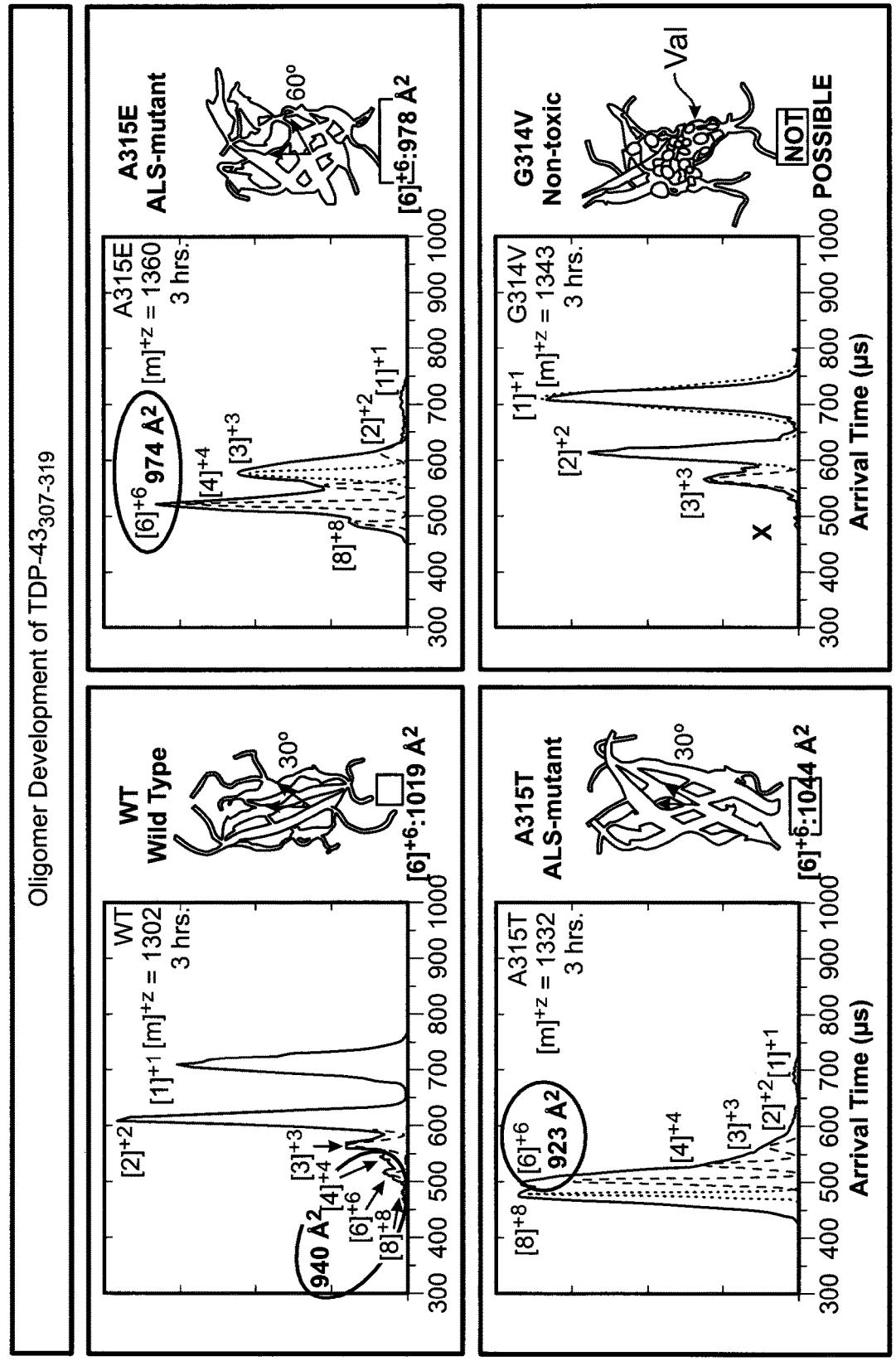
FIG. 1 shows oligomer development of TDP-43307-319.
Figure 2:
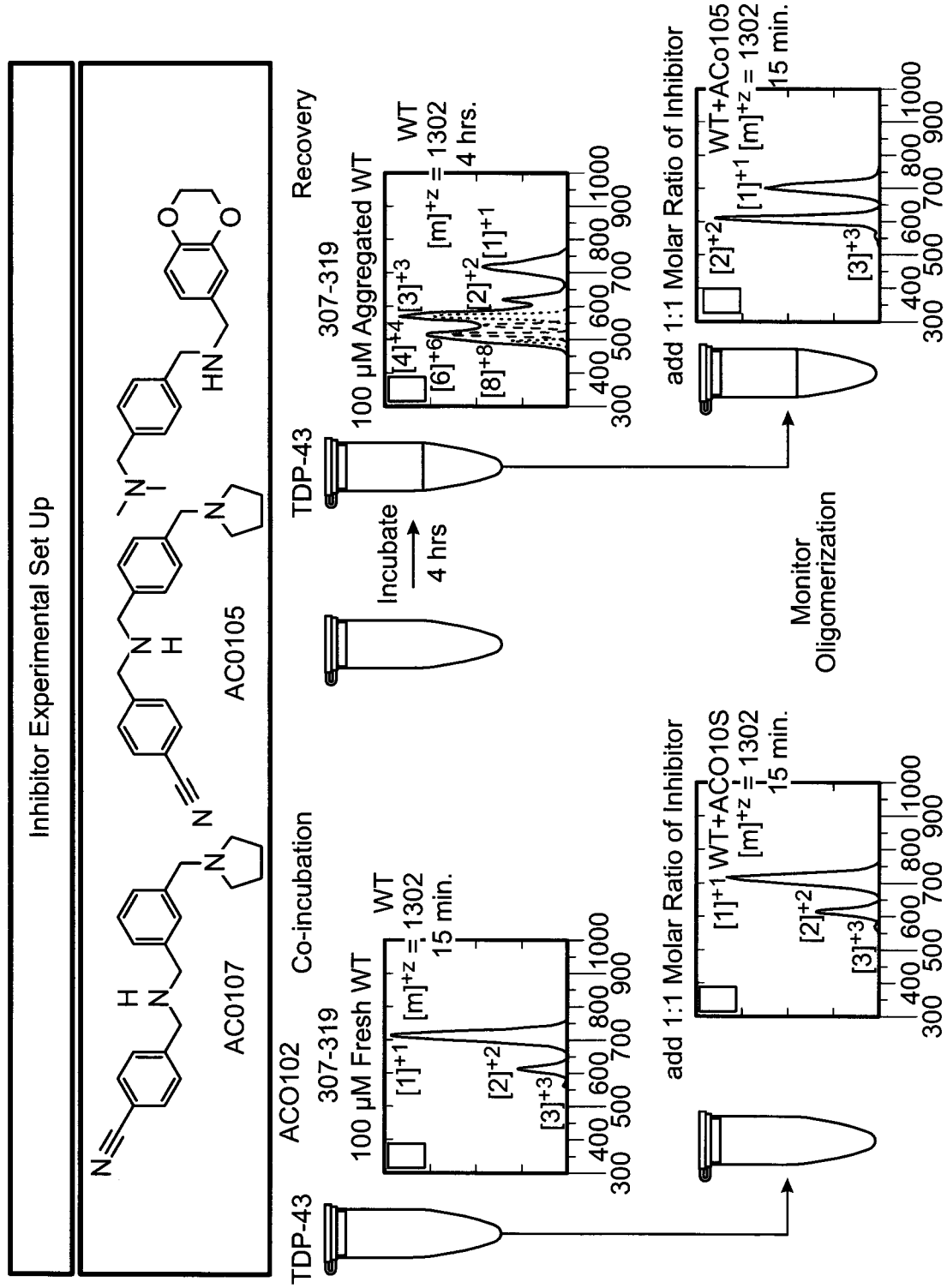
FIG. 2 shows an experimental set up for inhibitor analysis.
Figure 3:
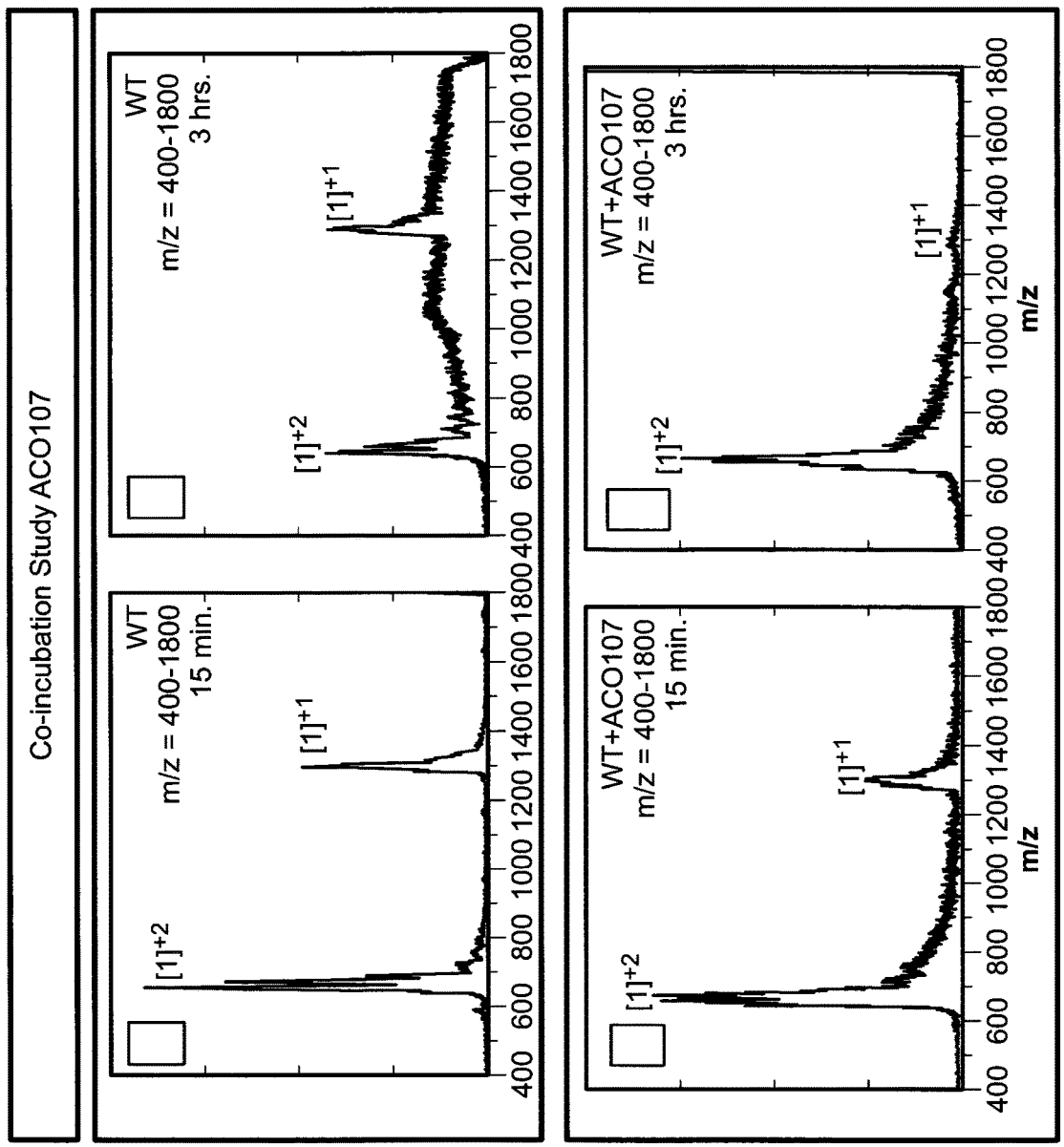
FIG. 3 shows a co-incubation study with AC0107.
Figure 4:
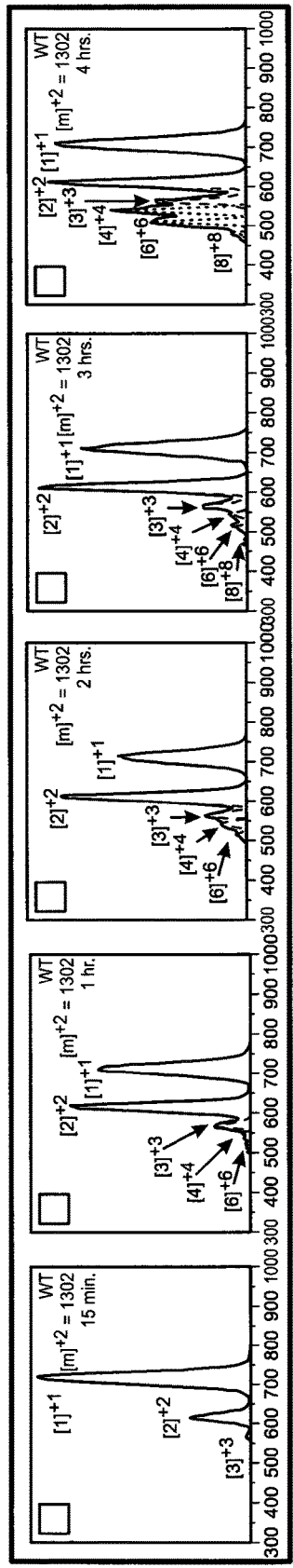
FIG. 4 shows further results of the co-incubation study with AC0107.
Figure 4:
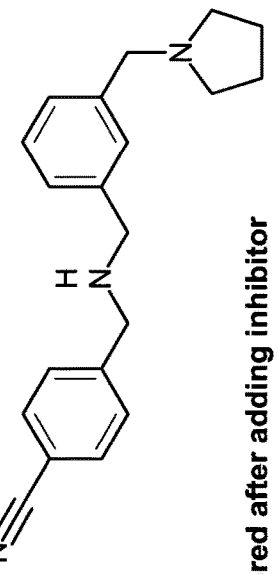
Figure 4:
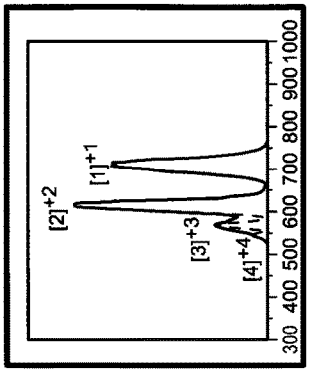
Figure 4:
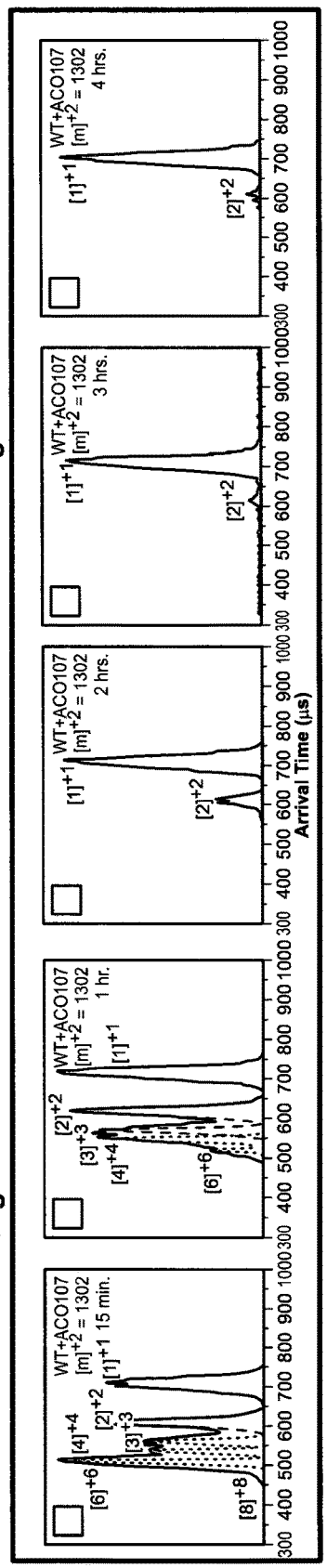
Figure 5:
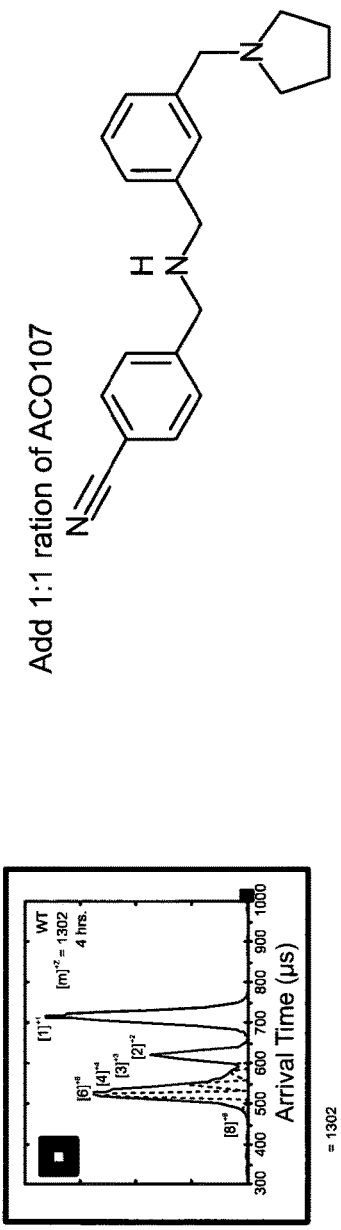
FIG. 5 shows a recovery study with AC0107.
Figure 5:
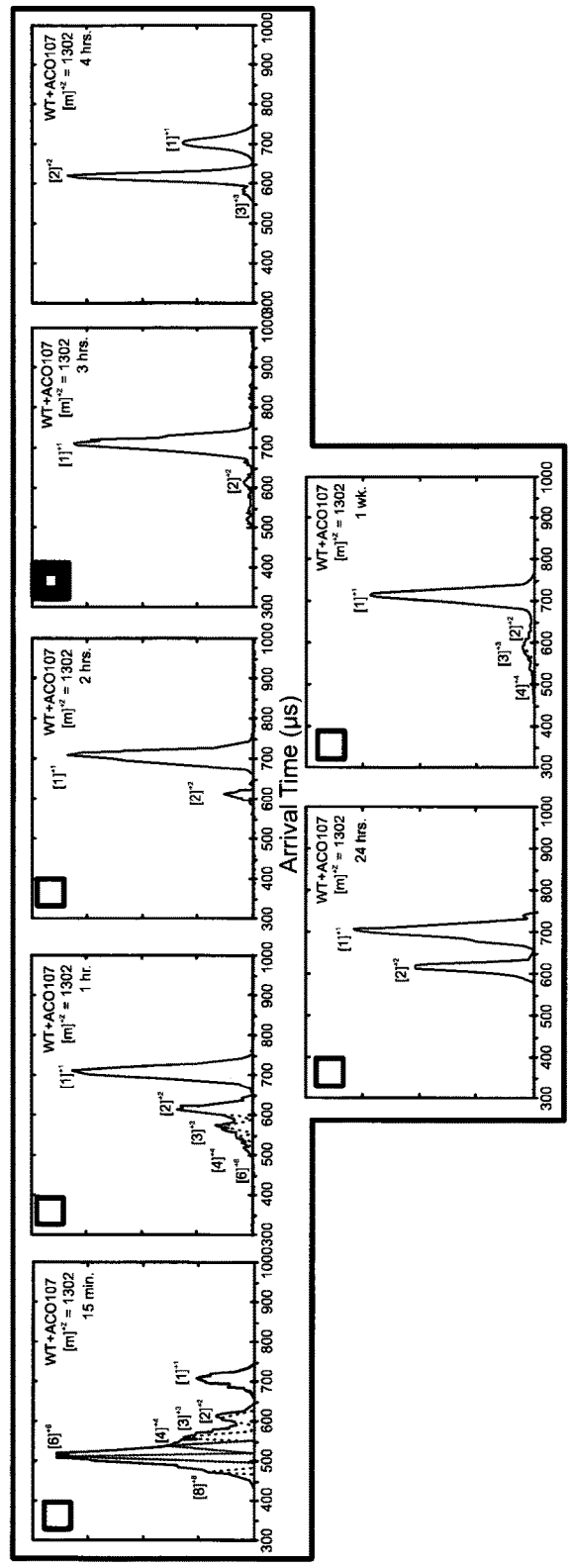
Figure 6:
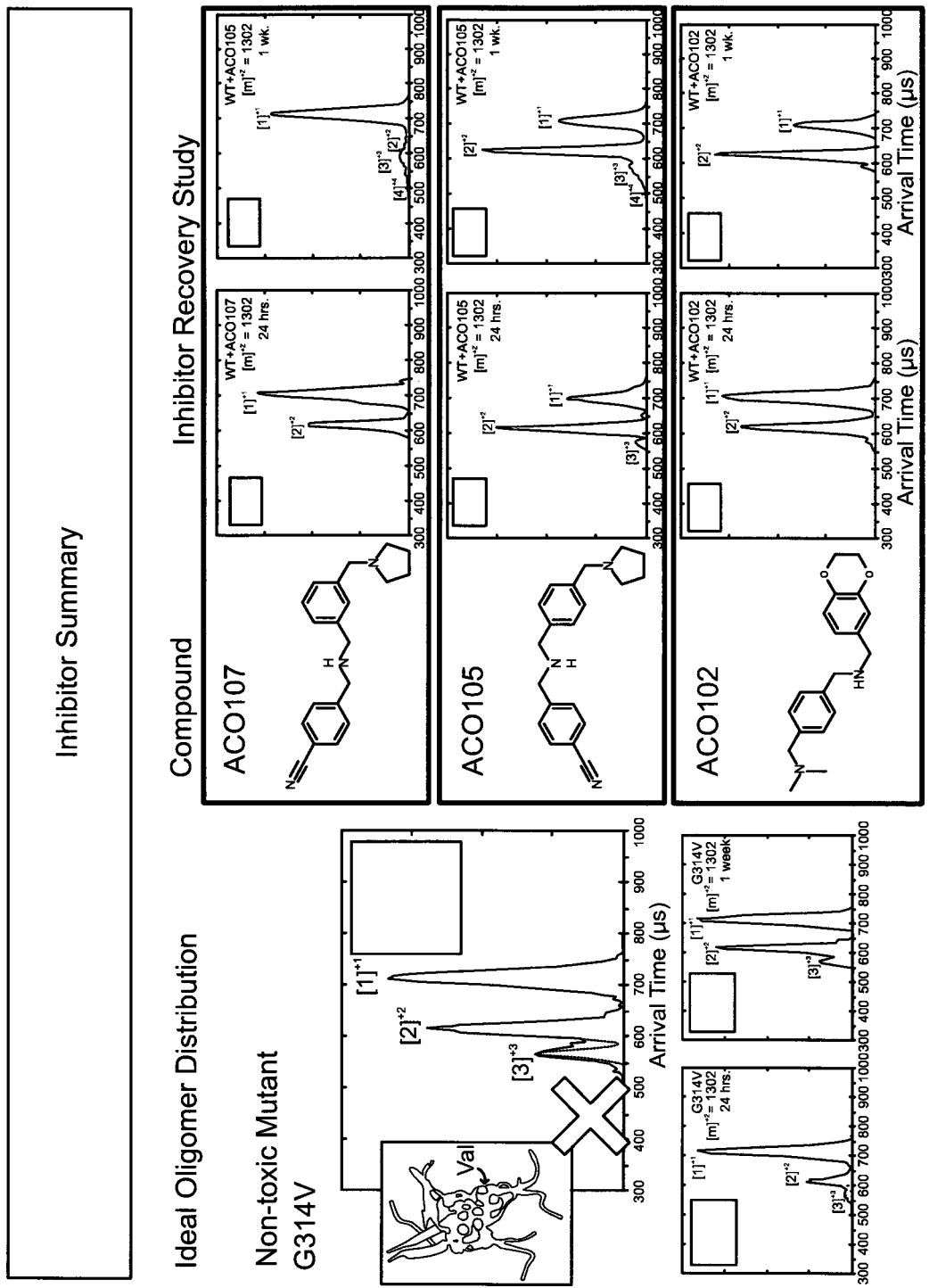
FIG. 6 shows an inhibitor summary.
Figure 7:
FIG. 7 shows a TDP-43 (307-319) recovery study with AC0201.
Figure 7:
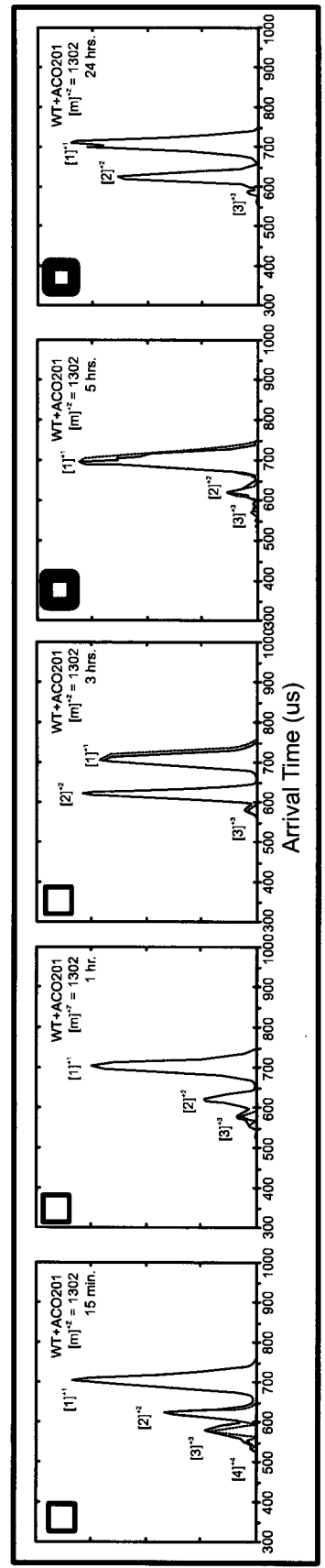
Figure 8:
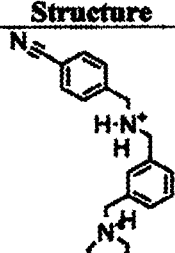
FIG. 8 shows certain compounds of the present invention, AC0101-AC0107.
Figure 8:
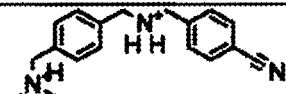
Figure 8:
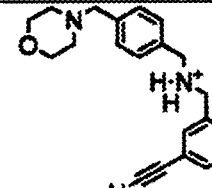
Figure 8:
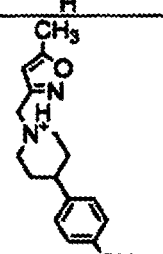
Figure 8:
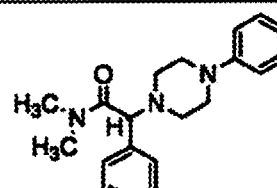
Figure 8:
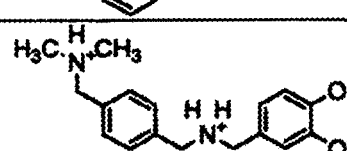
Figure 8:
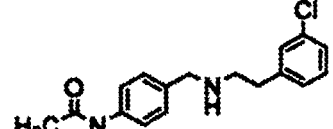

"Amyotrophic lateral sclerosis ("ALS")" is a progressive, neurodegenerative disease that affects nerve cells in the brain and spinal cord. It is the most prevalent motor neuron disease. There is currently no cure for ALS, and the average life expectancy for a person who has contracted the disease is two to five years. There are two different types of ALS, sporadic and familial. Sporadic ALS is the most common form of the disease in the US, accounting for approximately 90 to 95 percent of all cases. Familial ALS, which is inherited, accounts for five to 10 percent of cases in the US. Symptoms of ALS include: difficulty walking or doing your normal daily activities; tripping and falling; weakness in one's leg, feet or ankles; hand weakness or clumsiness; slurred speech or trouble swallowing; muscle cramps and twitching in one's arms, shoulders an tongue; difficulty holding one's head up or keeping good posture. It often starts in the hands, feet or limbs and then spreads to other parts of one's body. Muscles progressively weaken and nerve cells are destroyed as the disease advances. Eventually, this affects chewing, swallowing, speaking and breathing.

"Frontotemporal dementia" is a term used for a diverse group of disorders that primarily affect the frontal and temporal lobes of the brain. Portions of the frontal and temporal lobes shrink, or atrophy, in frontotemporaral dementia. Symptoms of this disease include behavioral changes, speech and language problems and movement disorders. Examples of behavioral changes comprise: increasingly inappropriate actions; loss of empathy and other interpersonal skills; lack of judgment and inhibition; apathy; repetitive compulsive behavior; a decline in personal hygiene; changes in eating habits, predominantly overeating; oral exploration and consumption of inedible objects; lack of awareness of thinking or behavioral changes. Examples of speech and language problems comprise: primary progressive aphasia; semantic dementia; progressive agrammatic aphasia. Examples of movement disorders comprise: tremor; rigidity; muscle spasms; poor coordination; difficulty swallowing; muscle weakness.

"Chronic traumatic encephalopathy ("CTE")" is a term used for brain degeneration probably caused by repeated head traumas. Symptoms of this disease include: difficulty thinking (cognitive impairment); impulsive behavior; depression or apathy; short-term memory loss; difficulty planning and carrying out tasks (executive function); emotional instability; substance misuse; suicidal thoughts or behavior.

"Progressive supranuclear palsy", or Steele-Richardson-Olszewski syndrome, is a brain disorder resulting from the deterioration of brain cells that control body movement and thinking. Symptoms of this disease include: a loss of balance while walking; an inability to aim one's eyes properly; stiffness and awkward movements; falling; problems with speech and swallowing; sensitivity to light; sleep disturbances; loss of interest in pleasurable activities; impulsive behavior, possibly including laughing or crying for no reason; difficulties with memory, reasoning, problem-solving and decision making; depression and anxiety; a surprised or frightened facial expression, resulting from rigid facial muscles.

"Corticobasal degeneration" is a term used to describe shrinkage of certain brain areas, such as the cerebral cortex and basal ganglia, and nerve cell degeneration or death. This causes growing difficulty in movement on one or both sides of one's body. Examples of symptoms include: poor coordination; stiffness; thinking (cognitive) difficulties; speech or language difficulty.

"Parkinson's disease" is a progressive nervous system disorder. The disease affects movement, and examples of symptoms include: tremor; slowed movement (bradykinesia); rigid muscles; impaired posture and balance; loss of automatic movements; speech changes; writing changes. Complications associated with Parkinson's include: thinking difficulties; depression and emotional changes; swallowing problems; chewing and eating problems; sleep problems and sleep disorders; bladder problems; constipation.

"Huntington's disease" is a term used for an inherited disease that causes the progressive degeneration of nerve cells in the brain. It has a substantial impact on a person's functional abilities and can result in movement, cognitive and psychiatric disorders. Examples of symptoms associated with movement disorders include: involuntary jerking or writhing movements (chorea); muscle problems, such as rigidity or muscle contracture (dystonia); slow or abnormal eye movements; impaired gait, posture and balance; difficulty with the physical production of speech or swallowing. Examples of symptoms associated with cognitive disorders include: difficulty organizing, prioritizing or focusing on tasks; lack of flexibility of the tendency to get stuck on a thought, behavior or action (perseveration); lack of impulse control that can result in outbursts, acting without thinking and sexual promiscuity; lack of awareness of one's own behaviors and abilities; slowness in processing thoughts; difficulty in learning new information. Examples of symptoms associated with psychiatric disorders include: feelings of irritability, sadness or apathy; social withdrawal; insomnia; fatigue and loss of energy; frequent thoughts of death, dying or suicide; obsessive-compulsive disorder; mania; bipolar disorder.

"Limbic-predominant age-related TDP-43 encephalopathy" ("LATE") is a type of dementia. The symptoms of LATE are similar to the symptoms of Alzheimer's, but LATE is caused by deposits of TDP-43 in the brain rather than beta-amyloid.

"Alpha-synuclein" is a protein that is abundant in the human brain and that is present in certain other body tissues (e.g., heart, muscle, gut). The protein tends to be concentrated near nerve cell (i.e., neuron) tips in association with synaptic vesicles that initiate the release of neurotransmitters. In certain disease states (e.g., Parkinson's) alpha-synuclein misfolds and forms a toxic aggregate.

"Tau proteins" are proteins that stabilize microtubules. The proteins are abundant in neurons. Diseases such as Alzheimer's and Parkinson's are associated with tau proteins that have become defective and aggregate.

"TDP-43" is a transcriptional repressor. It also regulates alternate splicing of the CFTR gene. A hyper-phosphorylated, ubiquitinated, cleaved form of TDP-43 is associated with ubiquitin-positive, tau-, and alpha-synuclein-negative frontotemporal dementia and amyotrophic lateral sclerosis.

"Huntingtin's protein" is a protein that is highly expressed in neurons and testes. It upregulates the expression of Brain Derived Neurotrophic Factor and is primarily associated with vesicles and microtubules.

The present invention is directed to small molecule compounds that reduce or inhibit or disrupt TDP-43, alpha-synuclein, tau protein and Huntingtin's protein oligomers, thereby treating or preventing ALS, LATE, Huntington's disease, Parkinson's disease, Alzheimer's, corticobasal degeneration, progressive supranuclear palsy, CTE, frontotemporaral dementia and/or related motor neuron diseases.

The term "oligomeric" or "oligomer" means a protein complex of a finite number of monomer subunits. In the context of the invention, oligomers are referred to as trimers, low-n-mers, hexamers, dodecamers (12-mers), and large-n-multimers composed of TDP-43 peptides, alpha-synuclein, tau protein and/or Huntingtin's protein.

The term "patient" or "subject" refers to animals, including mammals, humans, and non-human mammals. In certain embodiments, a patient is an animal, particularly an animal selected from a mammalian species including rat, rabbit, bovine, ovine, porcine, canine, feline, murine, equine, and primate, particularly human. In a preferred embodiment, the patient or subject is human.

"Treating" or "treatment of" a disease includes: (1) preventing the disease, i.e., causing the clinical symptoms of the disease not to develop in a patient that may be exposed to or predisposed to the disease but does not yet experience or display symptoms of the disease; (2) inhibiting the disease, i.e., arresting or reducing the development of the disease or its clinical symptoms; (3) relieving the disease, i.e., causing regression of the disease or its clinical symptoms; or (4) reducing the clinical symptoms of the disease.

The term "suffering" or "in need thereof" as it related to the term "treatment" refers to a patient or individual who has been diagnosed with or is predisposed to a disease. A patient may also be referred to being "at risk of suffering" from a disease. This patient has not yet developed characteristic disease pathology, however, are known to be predisposed to the disease due to family history, being genetically predisposed to developing the disease, or diagnosed with a disease or disorder that predisposes them to developing the disease to be treated.

In therapeutic applications, a pharmaceutical composition containing one or more compounds described herein is administered to a patient suspected of, or already suffering from ALS, LATE, Huntington's disease, Parkinson's disease, Alzheimer's, corticobasal degeneration, progressive supranuclear palsy, CTE, frontotemporaral dementia and/or related motor neuron diseases, wherein said compounds are administered in an amount sufficient to cure, or at least partially arrest, the symptoms of the disease (biochemical, histological and/or behavioral), including its complication and intermediate pathological phenotypes in development of the disease. In prophylactic applications, a pharmaceutical composition containing one or more compounds described herein is administered to a patient susceptible to, or otherwise at risk of, ALS, LATE, Huntington's disease, Parkinson's disease, Alzheimer's, corticobasal degeneration, progressive supranuclear palsy, CTE, frontotemporaral dementia and/or related motor neuron diseases, wherein said compounds are administered in an amount sufficient to eliminate or reduce the risk, lessen the severity, or delay the outset of the disease. This includes biochemical, histological and/or behavioral symptoms of the disease, its complications and intermediate pathological phenotypes presenting during development of the disease.

The "therapeutically effective amount" will vary depending on the compound, the disease and its severity and the age, weight, etc., of the patient to be treated all of which is within the skill of the attending clinician. It is contemplated that a therapeutically effective amount of one or more of the compounds described herein will alter or prevent TDP-43, alpha-synuclein, tau protein and/or Huntingtin's protein oligomer accumulation in the patient as compared to the absence of treatment. As such, movement impairment is decreased or prevented.

In some methods, administration of the compound reduces or eliminates muscle weakening in patients that have not yet developed characteristic ALS pathology. In particular embodiments, a therapeutically effective amount intends to indicate the amount of one or more compounds described herein administered or delivered to the patient, which is most likely to result in the desired response to treatment. In other methods, administration of the compound reduces or eliminates muscle weakening, behavioral changes, speech and language problems, and/or movement in patients that have frontotemporal dementia. In other methods, administration of the compound reduces or eliminates cognitive impairment, impulsive behavior, depression or apathy in patients that have CTE. In other methods, administration of the compound reduces or eliminates loss of balance, an inability to aim one's eyes properly and movement issues in patients that have progressive supranuclear palsy. In other methods, administration of the compound reduces or eliminates poor coordination, stiffness, cognitive difficulties and speech or language difficulties in patients that have corticobasal degeneration. In other methods, administration of the compound reduces or eliminates tremor, slowed movement, rigid muscles, impaired posture and balance, loss of automatic movements, speech changes and writing changes in patients that have Parkinson's disease. In other methods, administration of the compound reduces or eliminates movement disorders, cognitive disorders and psychiatric disorders in patients that have Huntington disease. In other methods, administration of the compound reduces or eliminates dementia-related symptoms in patients that have LATE.

Embodiments of the present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile (ACN) are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

For oral administration, the pharmaceutically acceptable formulation may include a carrier, which may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The disclosed compositions may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

Examples of the carrier, the excipient, and the diluent suitable for the pharmaceutical formulations include, without limitation, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Effective doses of the compositions of the present invention, for the treatment of the above described diseases vary depending upon may different factors, including means of administration, physiological state of the patient, whether the patient is human or an animal, other medications administered, and whether treatment is prophylactic or therapeutic. Usually, the patient is a human, but in certain embodiments, a patient is an animal, particularly an animal selected from a mammalian species including canine, feline, murine, equine, and primate.

The compounds can be administered on multiple occasions, wherein intervals between single dosages can be daily, weekly, monthly, or yearly. Intervals can also be irregular as indicated by measuring blood levels of TDP-43 protein, alpha-synuclein, tau protein, Huntingtin's protein or related oligomers in the patient. Alternatively, one or more of the compounds of the invention can be administered as a sustained-release formulation, in which case less frequent administration is required. Dosage and frequency may vary depending on the half-life of the compounds of the invention. In therapeutic applications, a relatively high dosage at relatively short intervals is sometimes required until progression of the disease is reduced or terminated, and preferably until the patient shows partial or complete amelioration of symptoms of the disease. Thereafter, the patient can be administered a prophylactic regime.

Administration of a pharmaceutical composition of the compounds described herein can be carried out via a variety of routes including, but are not limited to, oral, topical, pulmonary, rectal, subcutaneous, intradermal, intranasal, intracranial, intramuscular, intraocular, or intra-articular injection and the like. The most typical route of administration is oral, although other routes can be equally effective.

One or more compounds described herein can optionally be administered in combination with other biological or chemical agents that are at least partly effective in treatment of a TDP-43 oligomer, alpha-synuclein oligomer, Huntingtin's protein oligomer or tau oligomer associated disease. An example of such an agent is, but are not limited to, TDP-43 directed antibodies as described in The Journal of Chemical Investigation, published Jan. 22, 2019.

The compounds described herein may be administered to a patient in an amount sufficient to inhibit, regulate and/or TDP-43, alpha-synuclein, Huntingtin's protein or tau protein oligomers in said patient. A skilled clinician would be able to readily ascertain appropriate amounts of the compounds described here to effectively inhibit, regulate and/or modulate the formation of TDP-43, alpha-synuclein, Huntingtin's protein or tau protein oligomers in said patient. Contemplated amounts of the compounds described herein include for example, but are not limited to, from about 0.05 to 2000 mg/m2/day of one compound or more than one compound.

As noted above, the compounds described herein may be administered for example, but are not limited to, orally, topically, pulmonarily, rectally, subcutaneously, intradermally, intranasally, intracranially, intramuscularly, intraocularly, or intra-arterially and the like. The carrier or excipient or excipient mixture can be a solvent or a dispersive medium containing for example, but are not limited to, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Moreover, other or supplementary active ingredients can also be incorporated into the final composition.

Diseases that are treated by the methods described herein include ALS, Alzheimer's, LATE, Huntington's disease, Parkinson's disease, corticobasal degeneration, progressive supranuclear palsy, CTE, frontotemporaral dementia and/or related motor neuron diseases.

When employed as pharmaceuticals, the compounds of this invention are usually administered in the form of pharmaceutical compositions. These compounds can be administered by a variety of routes including oral, topical, pulmonary, rectal, subcutaneous, intradermal, intranasal, intracranial, intramuscular, intraocular, or intra-articular injection. These compounds are effective as both injectable and oral compositions. Such compositions are prepared in a manner well known in the pharmaceutical art and comprise at least one active compound.

This invention also includes pharmaceutical compositions that contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to patient. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated to provide quick, sustained or delayed release of the active ingredient after administration to the patient by employing procedures known in the art.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost effective. All of these factors ultimately determine the overall success and usefulness of an intravenous formulation.

Other accessory additives that may be included in pharmaceutical formulations of compounds of the present invention as follow: solvents: ethanol, glycerol, propylene glycol; stabilizers: ethylene diamine tetra acetic acid (EDTA), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer may be necessary to maintain the aqueous pH in the range of from about 4 to about 8 and more preferably in a range of from about 4 to about 6. The buffer system is generally a mixture of a weak acid and a soluble salt thereof, e.g., sodium citrate/citric acid; or the monocation or di-cation salt of a dibasic acid, e.g., potassium hydrogen tartrate; sodium hydrogen tartrate, phosphoric acid/potassium di-hydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffer:drug (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

One useful buffer in the invention is sodium citrate/citric acid in the range of 5 to 50 mg per mL of sodium citrate to 1 to 15 mg per mL of citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/mL, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

The intravenous formulation can be administered by direct intravenous injection, i.v. bolus, or can be administered by infusion by addition to an appropriate infusion solution such as 0.9% sodium chloride injection or other compatible infusion solution.

The compositions can be formulated in an oral unit dosage form. The term "unit dosage forms" refers to physically discrete units suitable as unitary dosages for a patient, each unit containing a predetermined quantity of active material calculated to produce the desired therapeutic effect, in association with a suitable pharmaceutical excipient.

The total effective dose of the compositions disclosed herein may be administered to a patient in a single dose or may be administered for a long period of time in multiple doses according to a fractionated treatment protocol. In the pharmaceutical composition disclosed herein, the content of active ingredient may vary depending on the disease severity. Preferably, the total daily dose of the compounds disclosed herein may be approximately 0.0001 to 500 mg per 1 kg of body weight of a patient. However, the effective dose of the compound is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows suitable effects. Moreover, the pharmaceutical composition may be administered alone or in combination or coincident with other pharmaceutical formulations showing prophylactic or therapeutic efficacy In one embodiment, the dose of the composition may be administered daily, semi-weekly, weekly, bi-weekly, or monthly. The period of treatment may be for a week, two weeks, a month, two months, four months, six months, eight months, a year, or longer. The initial dose may be larger than a sustaining dose. In one embodiment, the dose ranges from a weekly dose of at least 0.10 mg, at least 0.50 mg, at least 1.0 mg, at least 5.0 mg, at least 10.0 mg, at least 50.0 mg, at least 100.0 mg, at least 500.0 mg, at least 1.0 g, at least 5.0 g, or at least 10.0 g. In one embodiment, a weekly dose may be at most 0.5 mg, at most 2.5 mg, at most 5.0 mg, at most 25.0 mg, at most 50.0 mg, at most 250.0 mg, at most 500.0 mg, at most 2.50 g, at most 5.0 g, at most 25.0 g or at most 50.0 g. In a particular aspect, the weekly dose may range from 1.0 mg to 50.0 g, from 10.0 mg to 25.0 g, or from 100 mg to 5.0 g.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.05 to about 2000 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices that deliver the formulation in an appropriate manner.

Compounds for the Treatment of ALS, Alzheimer's, LATE, Huntington's Disease, Parkinson's Disease, Corticobasal Degeneration, Progressive Supranuclear Palsy, CTE, Frontotemporaral Dementia and/or Related Motor Neuron Diseases.

"Acyl" refers to a ketone substituent, C(O)R, where R is alkyl or substituted alkyl, aryl or substituted aryl as defined herein.

"Alkenyl" refers to an unsaturated "alkyl" group that contains a double bond.

"Alkoxy" refers to an —OR group, where R is alkyl, or a substituted analogue thereof. Suitable alkoxy groups include, for example, methoxy, ethoxy, t-butoxy, etc.

"Alkyl" refers to a branched or unbranched, saturated or unsaturated, monovalent and hydrocarbon group, generally having from about 1-30 carbons and preferably, from 4-20 carbons and more preferably from 6-18 carbons. When the alkyl group has from 1-6 carbon atoms, it is referred to as a "lower alkyl." Branched structures have a branching motif similar to i-propyl, t-butyl, i-butyl, 2-ethylpropyl, etc. As used herein, the term encompasses "substituted alkyls," and "cyclic alkyl." The term (C1-C8)alkyl refers to an alkyl that has between one and eight carbon atoms.

"Alkynyl" refers to an unsaturated "alkyl" group that contains a triple bond.

"Amino" refers to —NRR', wherein R and R' are independently H, alkyl, aryl or substituted analogues thereof. "Amino" encompasses "alkylamino" denoting secondary and tertiary amines and "acylamino" describing the group RC(O) NR'. "Aryl" refers to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl" and "substituted aryl."

"Arylalkyl" refers to a subset of "aryl" in which the aryl group is attached to another group by an alkyl group as defined herein.

"Aryloxy" refers to aromatic groups that are linked to another group directly through an oxygen atom. This term encompasses "substituted aryloxy" moieties in which the aromatic group is substituted as described above for "substituted aryl." Exemplary aryloxy moieties include phenoxy, substituted phenoxy, benzyloxy, phenethyloxy, etc.

"Aryloxyalkyl" refers to aromatic groups attached, through an oxygen atom to an alkyl group, as defined herein. The term "aryloxyalkyl" encompasses "substituted aryloxyalkyl" moieties in which the aromatic group is substituted as described for "substituted aryl."

"Electron withdrawing group" refers to an atom or group that draws electron density from neighboring atoms towards itself through resonance or inductive effects. This includes groups such as —$NO_2$, —CN, —C(O)H, —C(O)R where "R" is an alkyl group, —$CO_2R$ where "R" is an alkyl group, and —$CO_2H$.

"Halogen" refers to fluorine, bromine, chlorine and iodine atoms.

"Heteroaryl" refers to aromatic rings in which one or more carbon atoms of the aromatic ring(s) are replaced by a heteroatom such as nitrogen, oxygen or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a diazo, methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" refers to a subset of "heteroaryl" wherein an alkyl group, as defined herein, links the heteroaryl group to another group.

"Heterocyclic" refers to a monovalent saturated or unsaturated non-aromatic group having a single ring or multiple condensed rings from 1-12 carbon atoms and from 1-4 heteroatoms selected from nitrogen, sulfur or oxygen within the ring. Such heterocycles are, for example, tetrahydrofuran, morpholine, piperidine, pyrrolidine, etc.

"Heterocyclicalkyl" refers to a subset of "heterocyclic" wherein an alkyl group, as defined herein, links the heterocyclic group to another group.

"Hydroxy" refers to the group —OH.

"Mercapto" refers to moieties of the general structure —S—R wherein R is H, alkyl, aryl or heterocyclic as described herein.

"Saturated cyclic hydrocarbon" refers to groups such as the cyclopropyl, cyclobutyl, cyclopentyl, etc., and substituted analogues of these structures. These cyclic hydrocarbons can be single- or multi-ring structures.

"Substituted alkenyl" refers to an "alkenyl" that includes one or more substituents such as, for example, lower alkyl, aryl, acyl, halogen (e.g., alkylhalos), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkenyl moiety. Additionally, these groups may be pendent from, or integral to, the alkenyl chain.

"Substituted alkyl" refers to an "alkyl" that includes one or more substituents such as, for example, lower alkyl, aryl, acyl, halogen (e.g., alkylhalos), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

"Substituted alkynyl" refers to an "alkynyl" that includes one or more substituents such as, for example, lower alkyl, aryl, acyl, halogen (e.g., alkylhalos), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkynyl moiety. Additionally, these groups may be pendent from, or integral to, the alkynyl chain.

"Substituted aryl" refers to an "aryl" that includes one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a diazo, methylene or ethylene moiety. The linking group may also be a carbonyl such as in cyclohexyl phenyl ketone. The term "substituted aryl" encompasses "substituted arylalkyl."

"Substituted arylalkyl" refers to a subset of "substituted aryl" wherein the substituted aryl group is attached to another group by an alkyl group as defined herein.

"Substituted heteroaryl" refers to a heteroaryl wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" in which an alkyl group, as defined herein, links the heteroaryl group to another group.

"Substituted heterocyclic" refers to a subset of "heterocyclic" wherein the heterocycle nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

"Unsaturated cyclic hydrocarbon" refers to a monovalent non-aromatic group with at least one double bond, such as cyclopentene, cyclohexene, etc. and substituted analogues thereof. These cyclic hydrocarbons can be single- or multi-ring structures.

FIGS. 9-29 show certain compounds according to the present invention for the treatment of ALS, LATE, Huntington's Disease, Parkinson's Disease, Alzheimer's, Corticobasal Degeneration, Progressive Supranuclear Palsy, CTE, Frontotemporaral Dementia and/or Related Motor Neuron Diseases. Where a cation is shown (e.g., compounds 102 and 106) a negatively charged, pharmaceutically acceptable counterion (e.g., AcO—) is implied.

Figure 9:
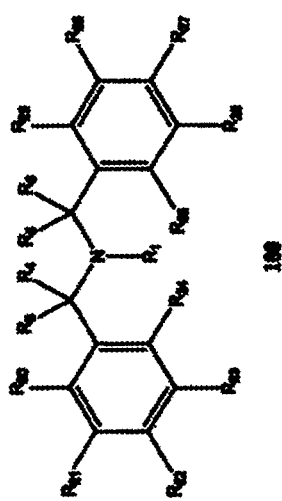
FIGS. 9-29 show certain compounds according to the present invention for the treatment of ALS or a related disease.
Figure 9:
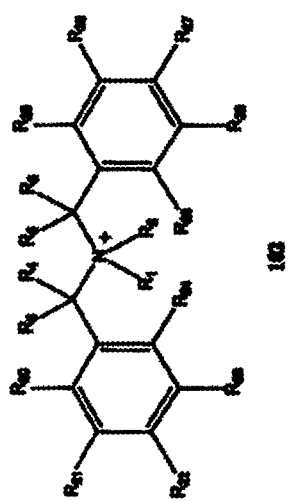
Figure 9:
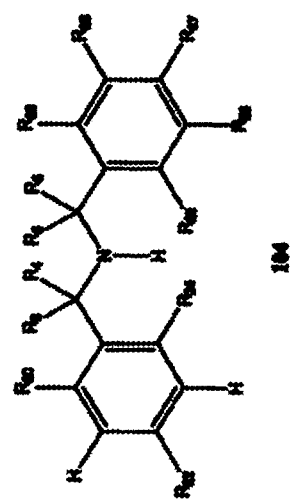

Referring to FIG. 9, compound 100, substituents $R_1$, $R_3$-$R_6$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 9, compound 102, substituents $R_1$-$R_6$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 9, compound 104, substituents $R_3$-$R_6$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 10:
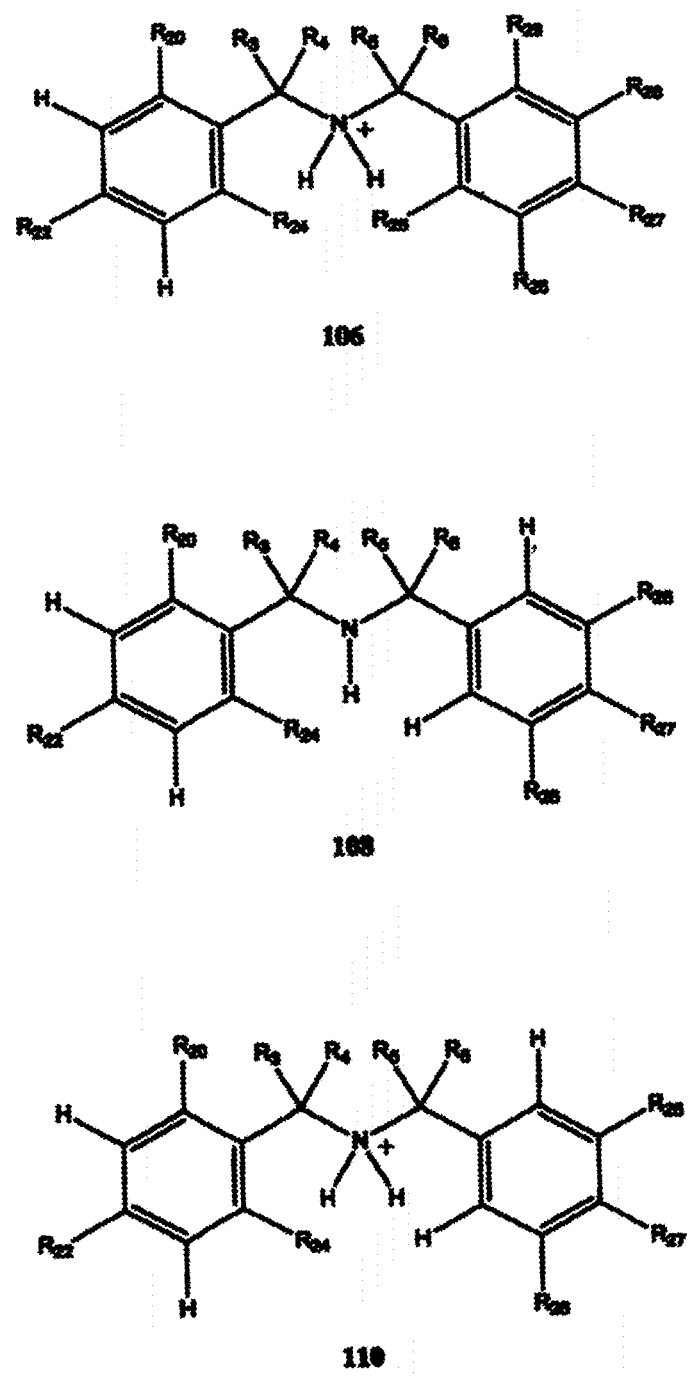

Referring to FIG. 10, compound 106, substituents $R_3$-$R_6$, $R_{20}$, $R_{22}$, $R_{24}$, $R_{25}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 10, compound 108, substituents $R_3$-$R_6$, $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 10, compound 110, substituents $R_3$-$R_6$, $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 11:
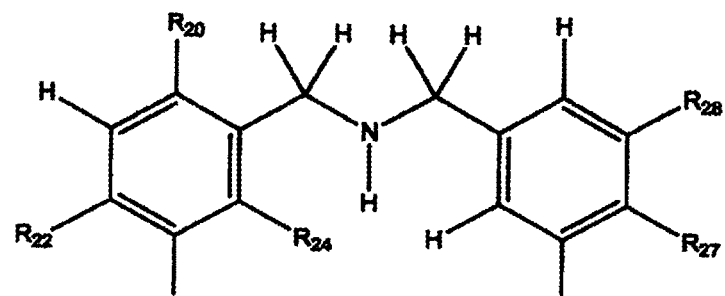
Figure 11:
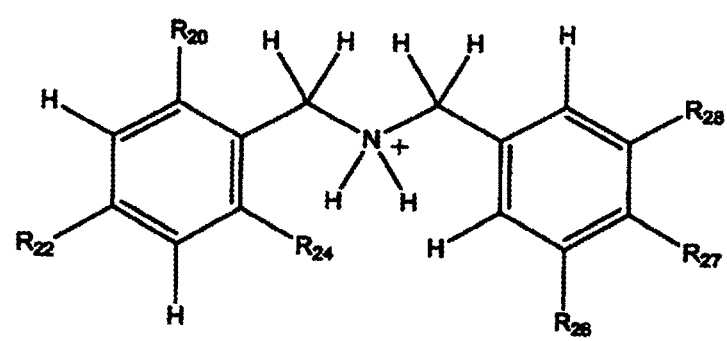
Figure 11:
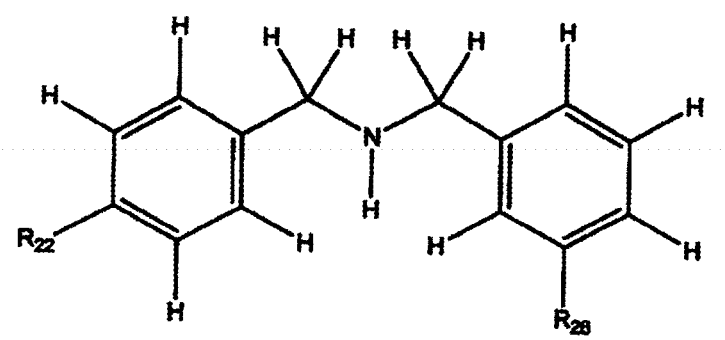

Referring to FIG. 11, compound 112, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 11, compound 114, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 11, compound 116, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 12:
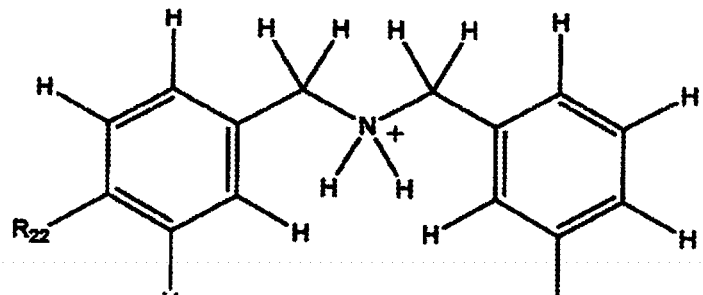
Figure 12:
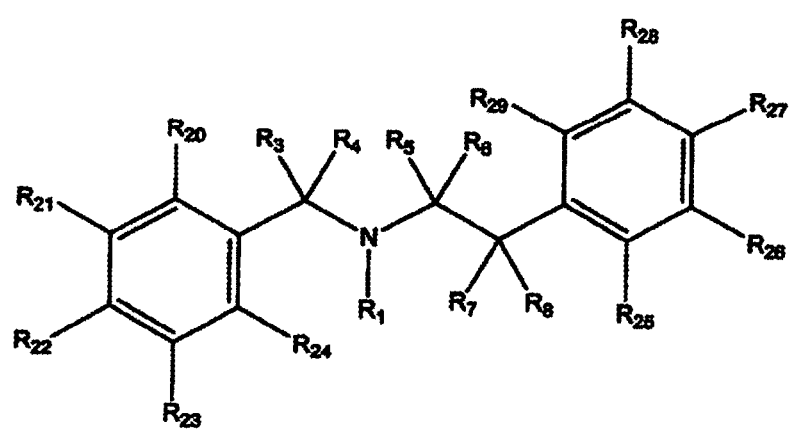
Figure 12:
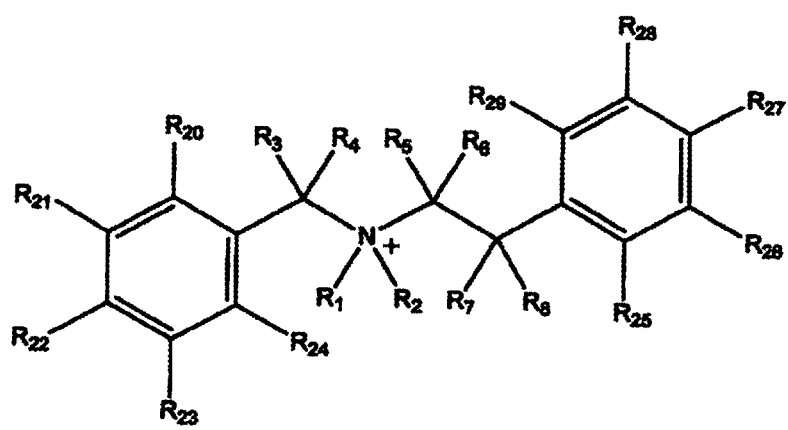

Referring to FIG. 12, compound 118, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 12, compound 120, substituents $R_1$, $R_3$-$R_8$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 12, compound 122, substituents $R_1$-$R_8$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 13:
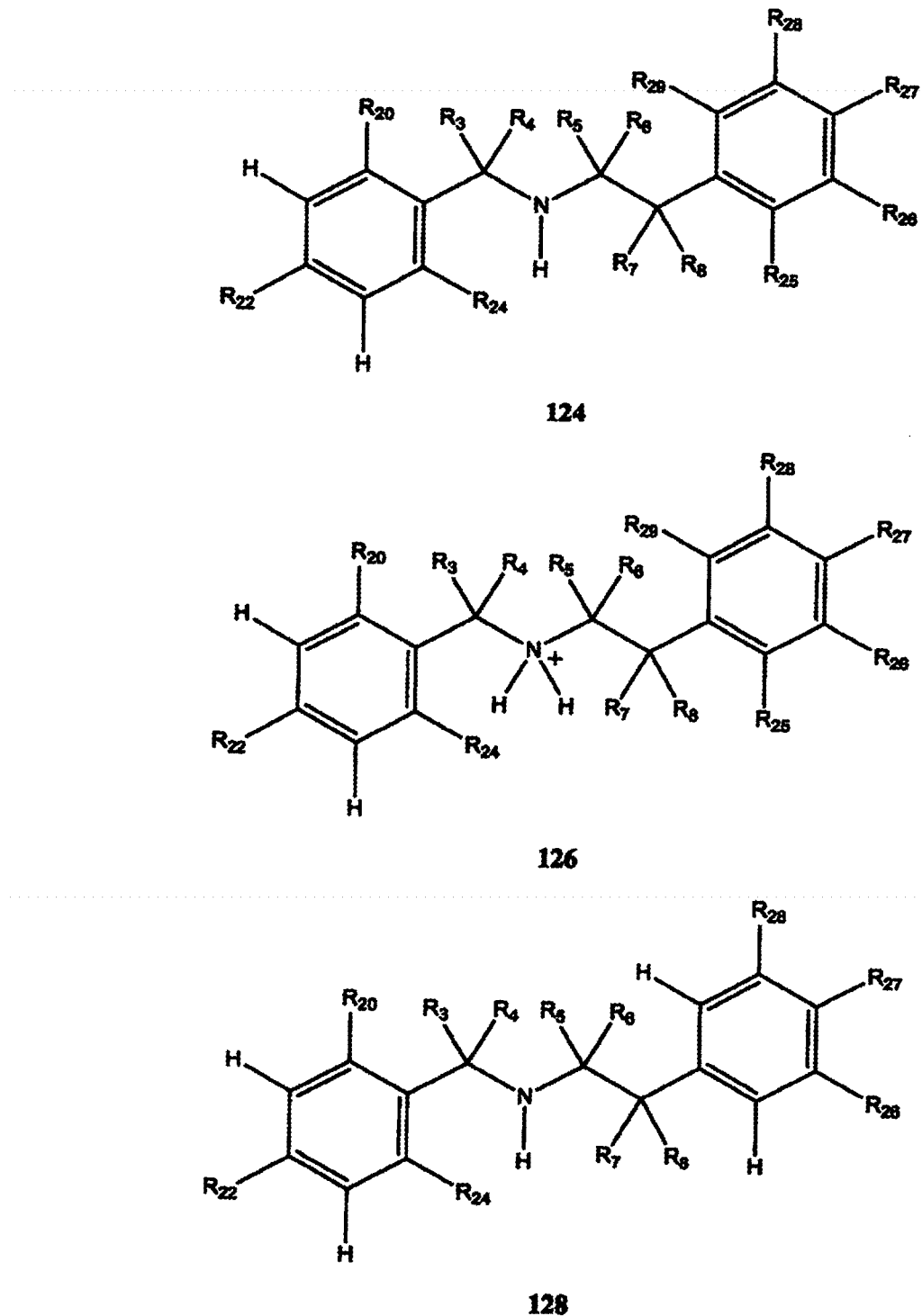

Referring to FIG. 13, compound 124, substituents $R_3$-$R_8$, $R_{20}$, $R_{22}$, $R_{24}$, $R_{25}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 13, compound 126, substituents $R_3$-$R_8$, $R_{20}$, $R_{22}$, $R_{24}$, $R_{25}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 13, compound 128, substituents $R_3$-$R_8$, $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 14:
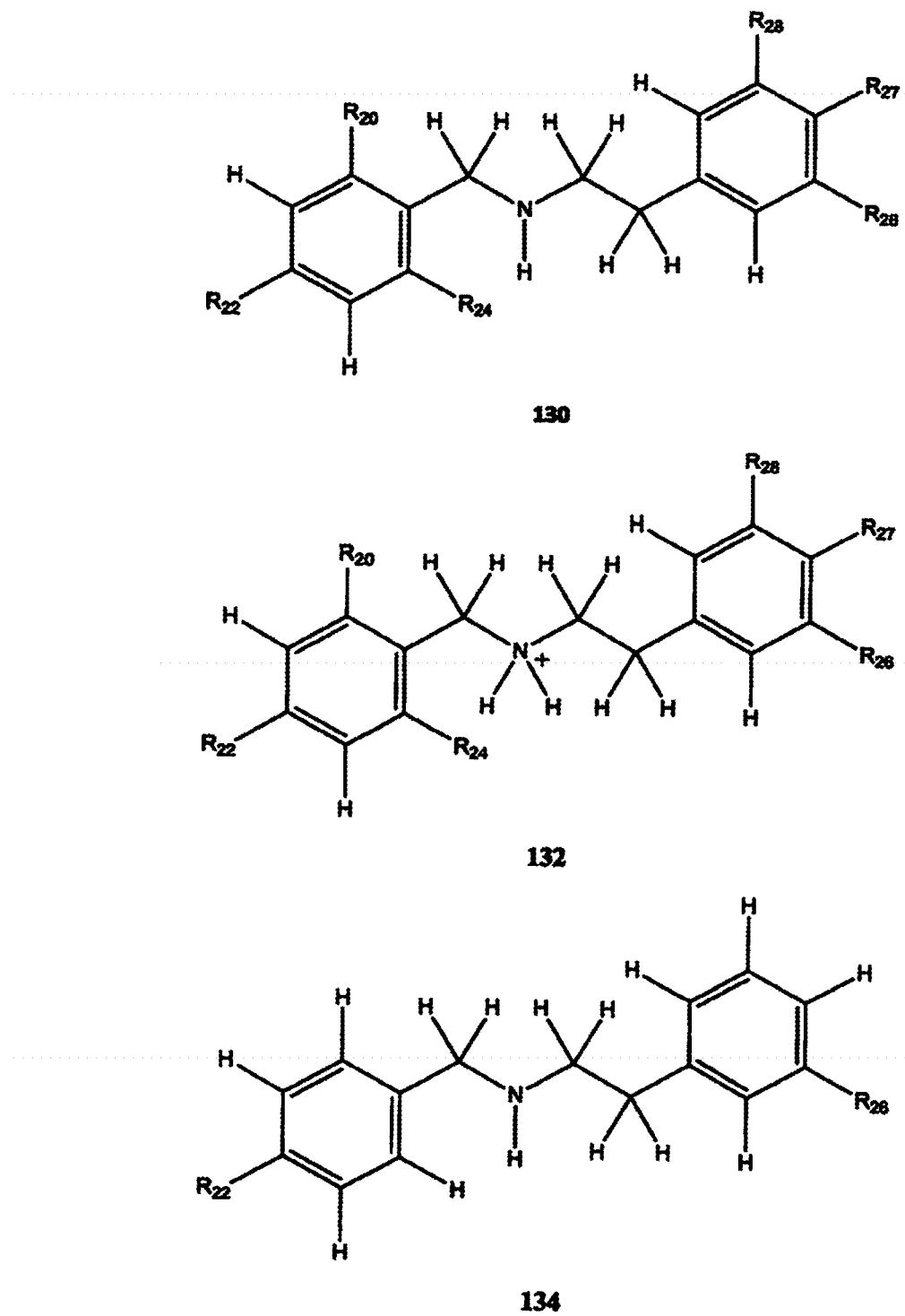

Referring to FIG. 14, compound 130, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 14, compound 132, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 14, compound 134, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 15:
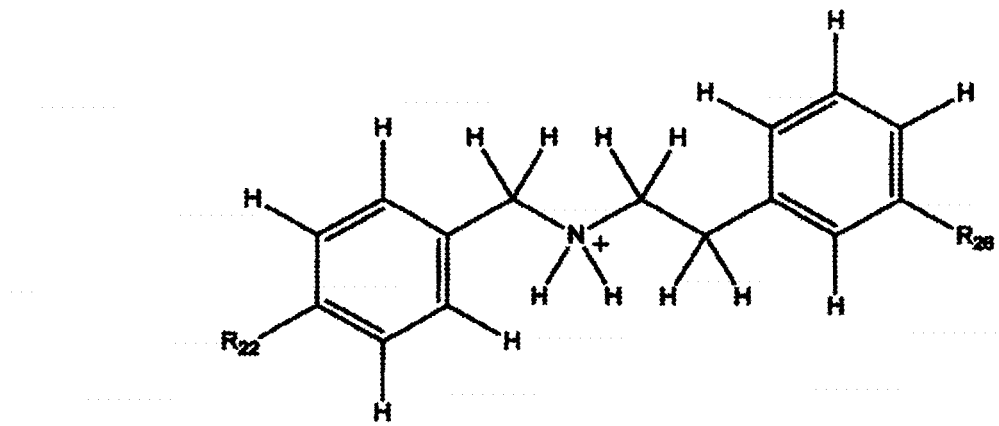
Figure 15:
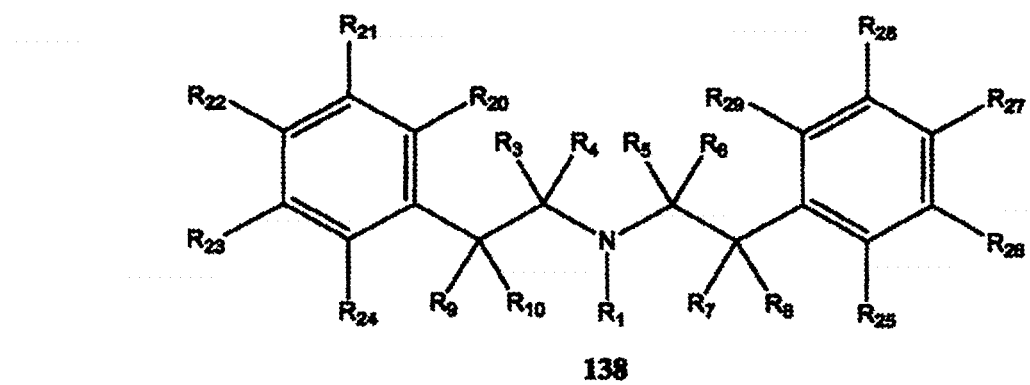
Figure 15:
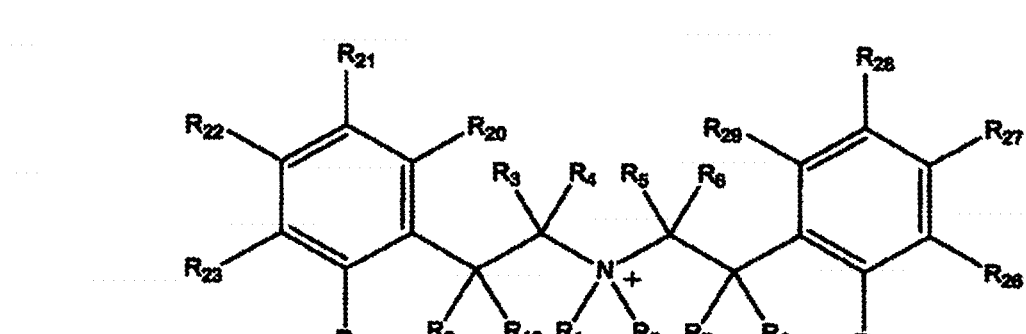

Referring to FIG. 15, compound 136, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 15, compound 138, substituents $R_1$, $R_3$-$R_{10}$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 15, compound 140, substituents $R_1$-$R_{10}$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 16:
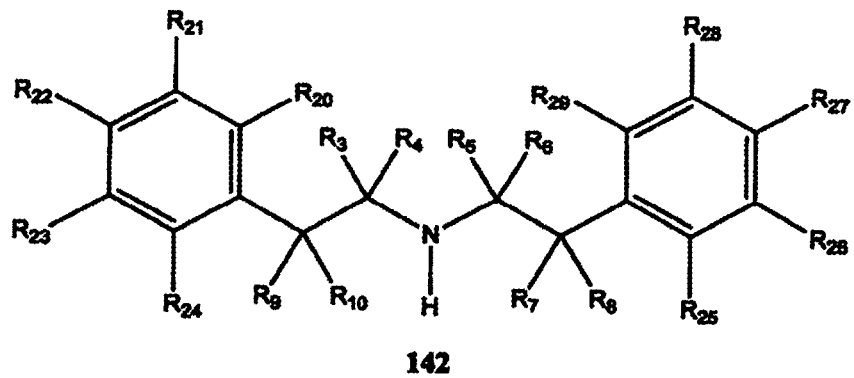
Figure 16:
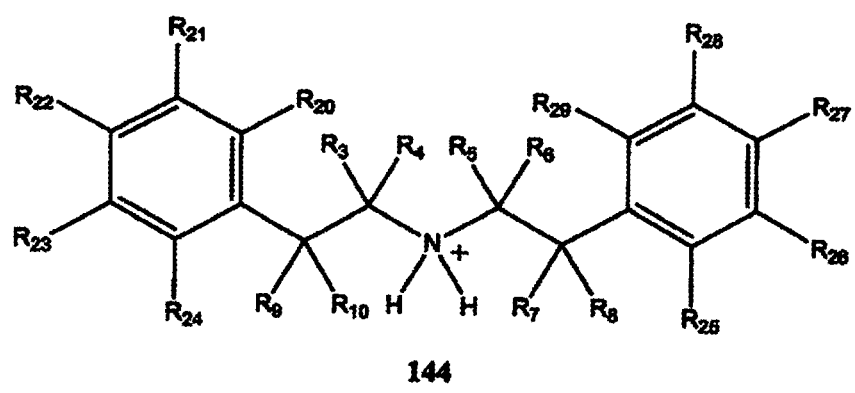
Figure 16:
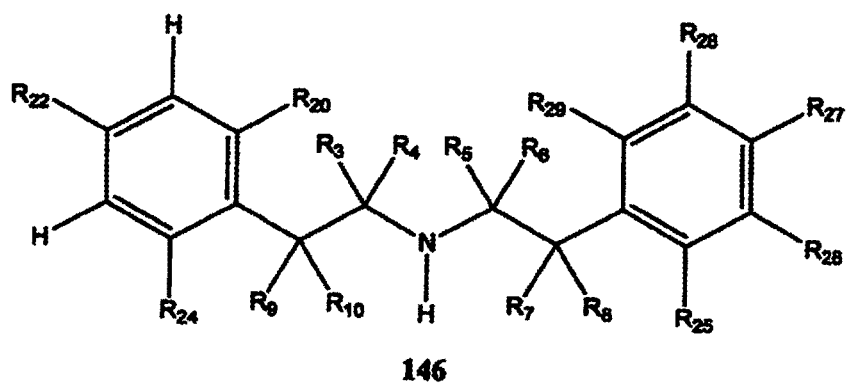

Referring to FIG. 16, compound 142, substituents $R_3$-$R_{10}$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 16, compound 144, substituents $R_3$-$R_{10}$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 16, compound 146, substituents $R_3$-$R_{10}$, $R_{20}$, $R_{22}$, $R_{24}$, $R_{25}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 17:
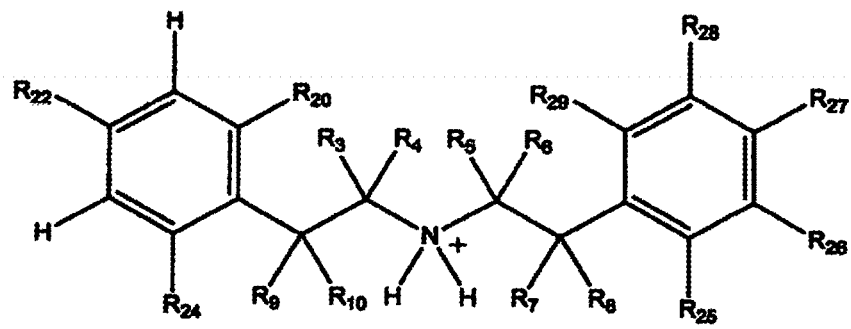
Figure 17:
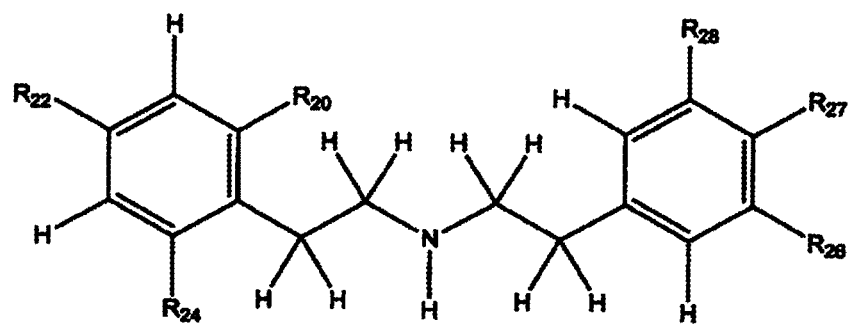
Figure 17:
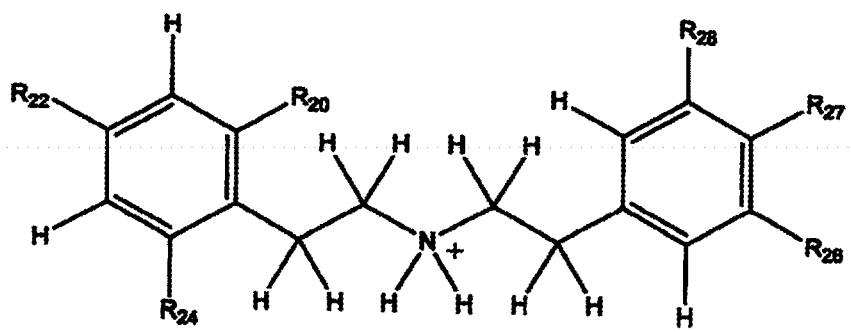

Referring to FIG. 17, compound 148, substituents $R_3$-$R_{10}$, $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 17, compound 150, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 17, compound 152, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 18:
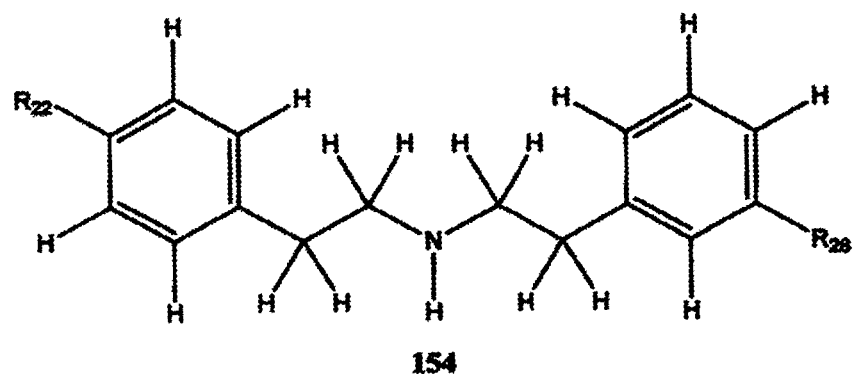
Figure 18:
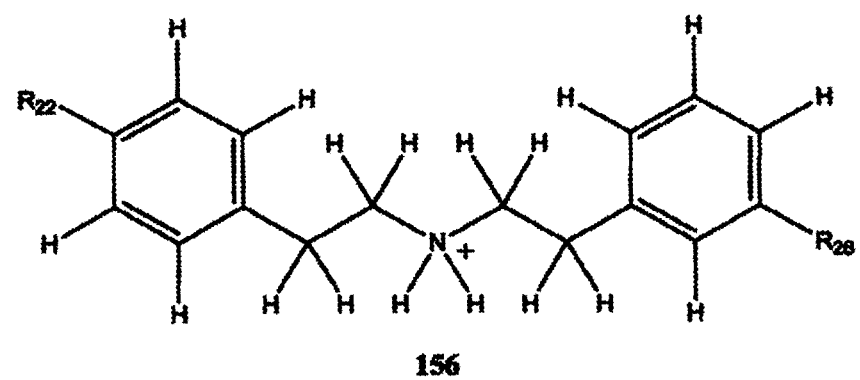
Figure 18:
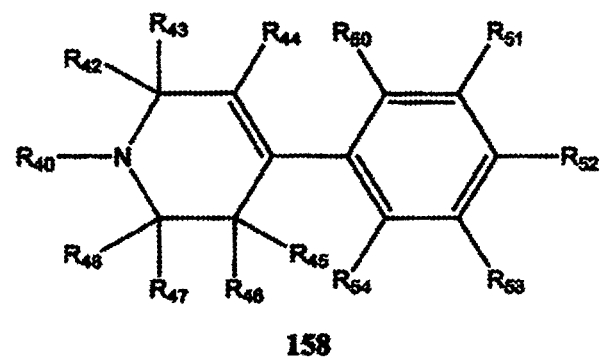

Referring to FIG. 18, compound 154, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 18, compound 156, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 18, compound 158, substituents $R_{40}$, $R_{42}$-$R_{48}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 19:
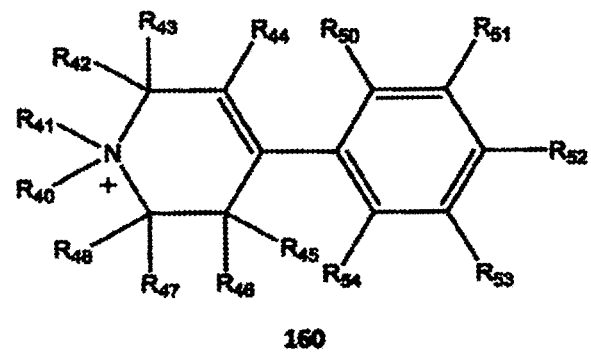
Figure 19:
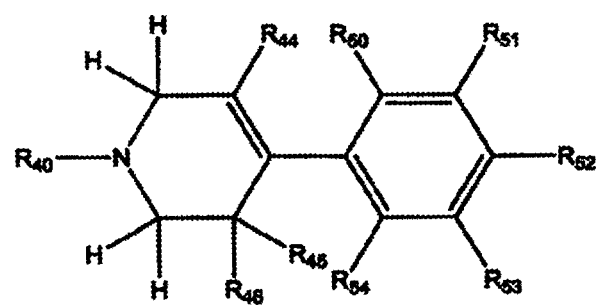
Figure 19:
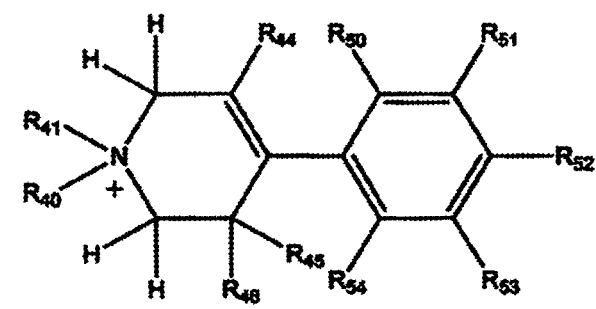

Referring to FIG. 19, compound 160, substituents $R_{40}$-$R_{48}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 19, compound 162, substituents $R_{40}$, $R_{44}$-$R_{46}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 19, compound 164, substituents $R_{40}$, $R_{41}$, $R_{44}$-$R_{46}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 20:
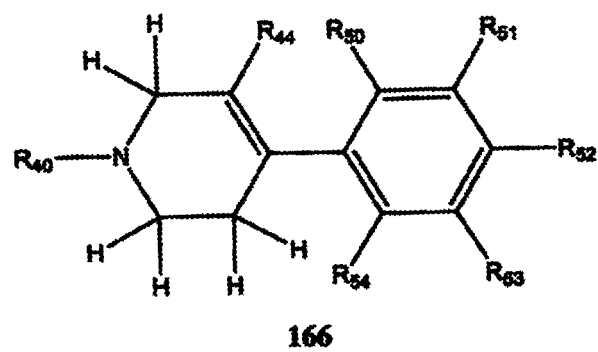
Figure 20:
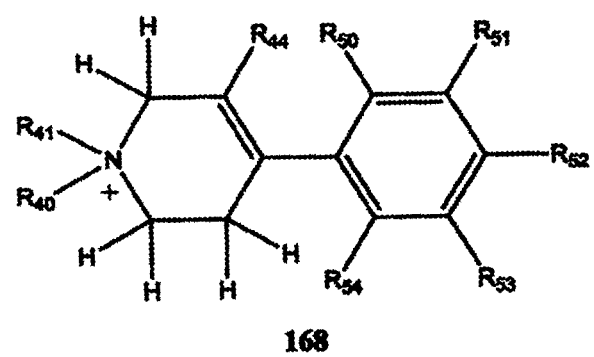
Figure 20:
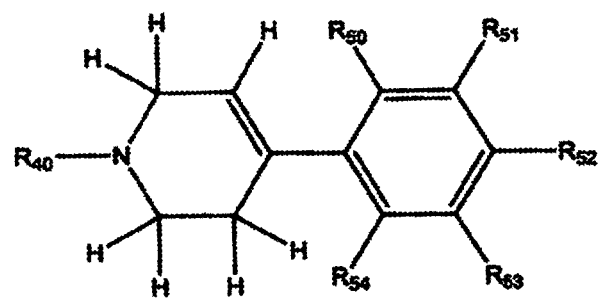

Referring to FIG. 20, compound 166, substituents $R_{40}$, $R_{44}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 20, compound 168, substituents $R_{40}$, $R_{41}$, $R_{44}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 20, compound 170, substituents $R_{40}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 21:
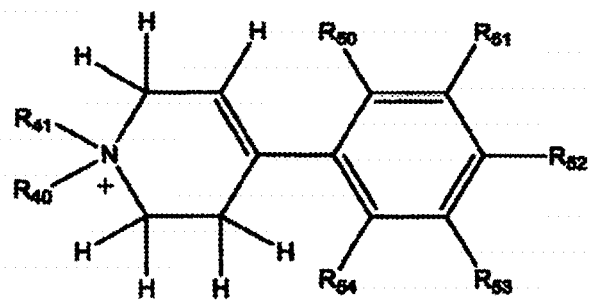
Figure 21:
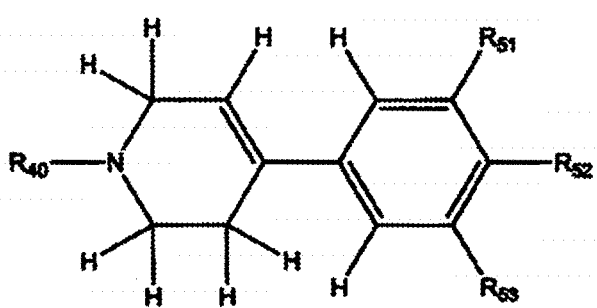
Figure 21:
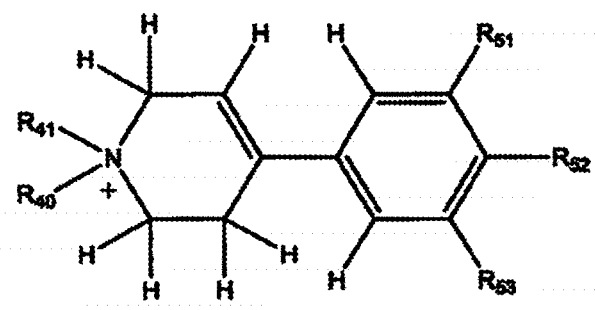

Referring to FIG. 21, compound 172, substituents $R_{40}$, $R_{41}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 21, compound 174, substituents $R_{40}$, $R_{51}$-$R_{53}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 21, compound 176, substituents $R_{40}$, $R_{41}$, $R_{51}$-$R_{53}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 22:
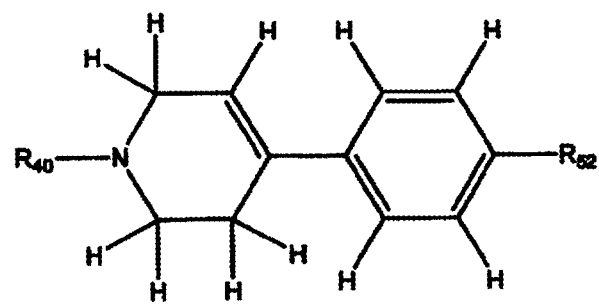
Figure 22:
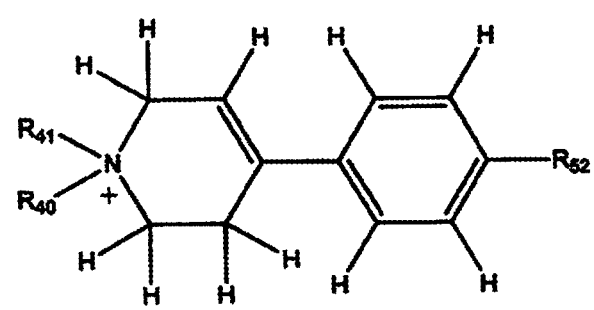
Figure 22:
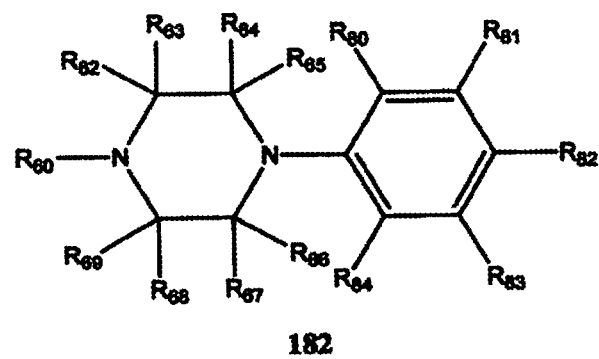

Referring to FIG. 22, compound 178, substituents $R_{40}$, $R_{52}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 22, compound 180, substituents $R_{40}$, $R_{41}$, $R_{52}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 22, compound 182, substituents $R_{60}$, $R_{62}$-$R_{69}$, $R_{80}$-$R_{84}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 23:
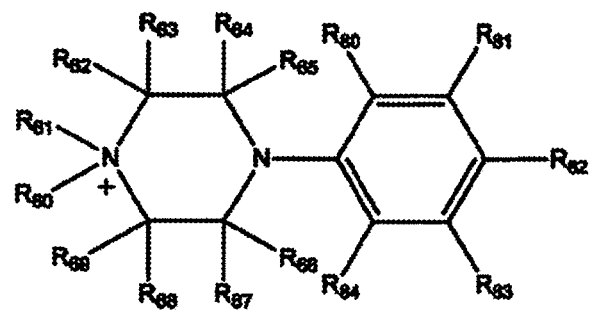
Figure 23:
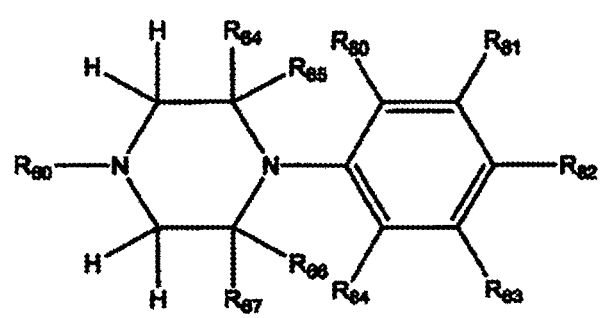
Figure 23:
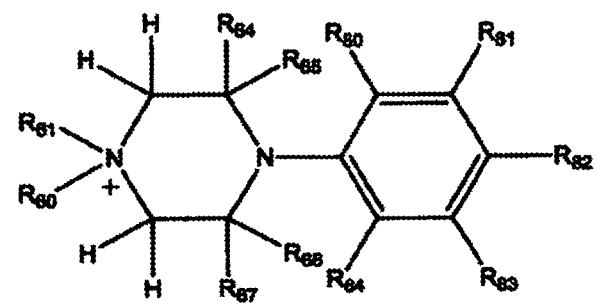

Referring to FIG. 23, compound 184, substituents $R_{60}$, $R_{61}$, $R_{62}$-$R_{69}$, $R_{80}$-$R_{84}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 23, compound 186, substituents $R_{60}$, $R_{64}$-$R_{67}$, $R_{80}$-$R_{84}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 23, compound 188, substituents $R_{60}$, $R_{61}$, $R_{64}$-$R_{67}$, $R_{80}$-$R_{84}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 24:
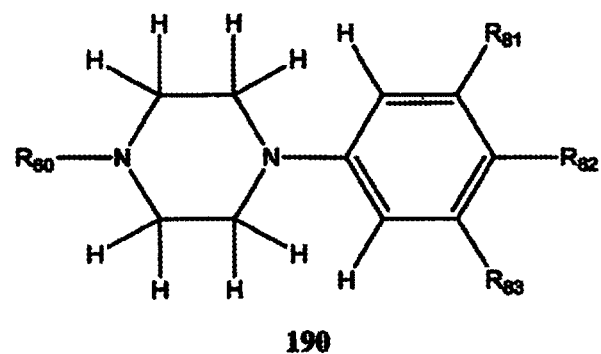
Figure 24:
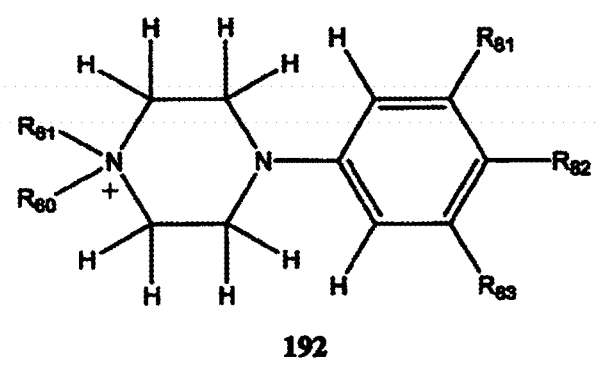
Figure 24:
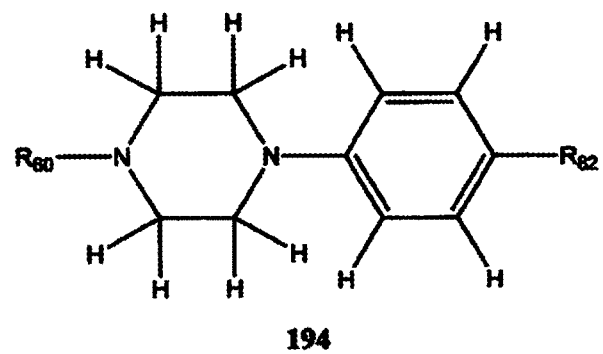

Referring to FIG. 24, compound 190, substituents $R_{60}$, $R_{81}$-$R_{83}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 24, compound 192, substituents $R_{60}$, $R_{61}$, $R_{81}$-$R_{83}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 24, compound 194, substituents $R_{60}$, $R_{82}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 25:
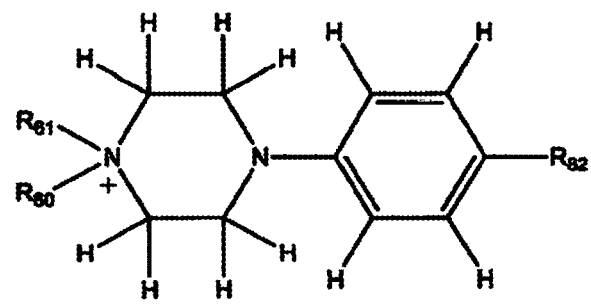
Figure 25:
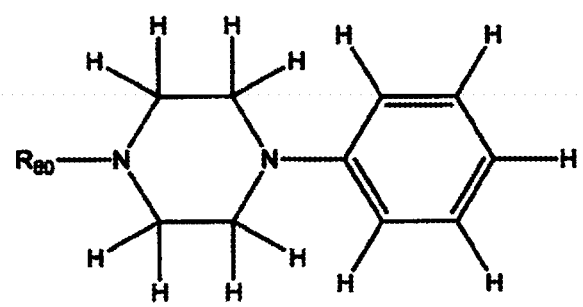
Figure 25:
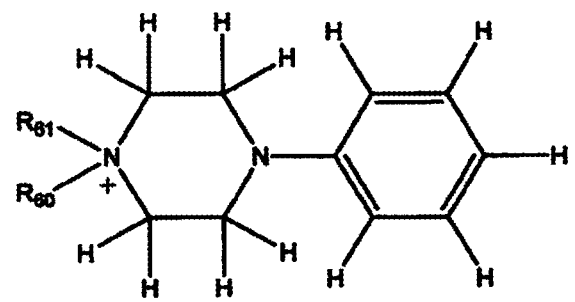

Referring to FIG. 25, compound 196, substituents $R_{60}$, $R_{61}$, $R_{82}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 25, compound 198, substituents Roo is independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 25, compound 200, substituents $R_{60}$, $R_{61}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 26:
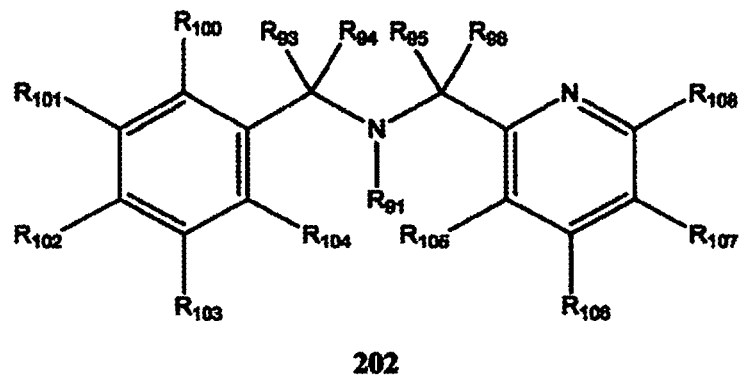
Figure 26:
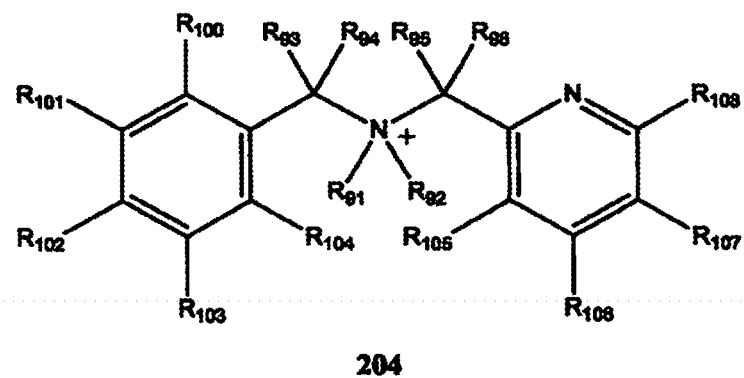
Figure 26:
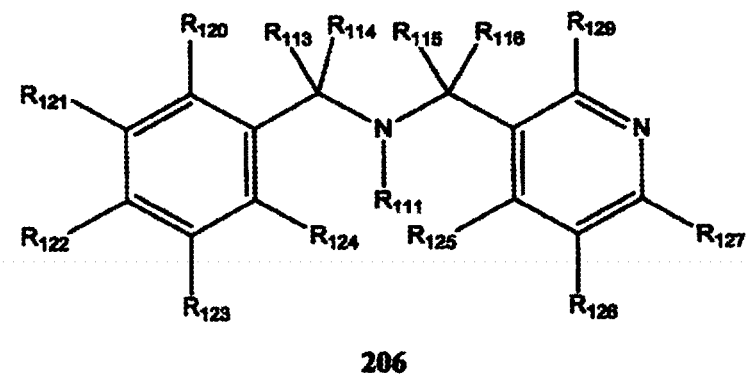

Referring to FIG. 26, compound 202, substituents $R_{91}$, $R_{93}$-$R_{96}$, $R_{100}$-$R_{108}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 26, compound 204, substituents $R_{91}$-$R_{96}$, $R_{100}$-$R_{108}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 26, compound 206, substituents $R_{111}$, $R_{113}$-$R_{116}$, $R_{120}$-$R_{127}$, $R_{129}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 27:
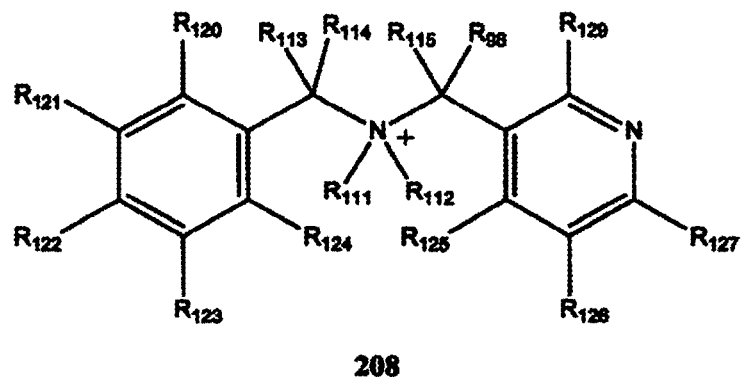
Figure 27:
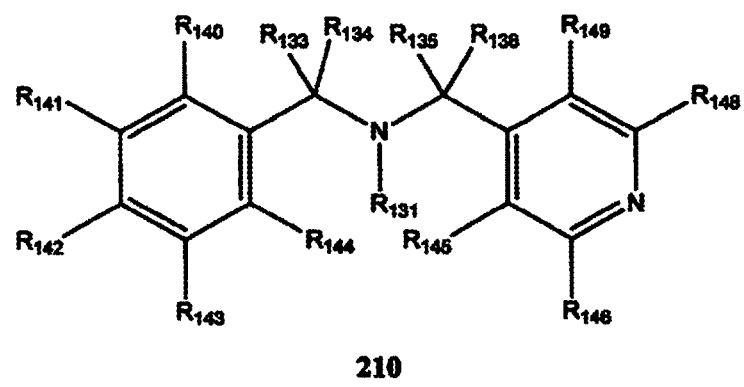
Figure 27:
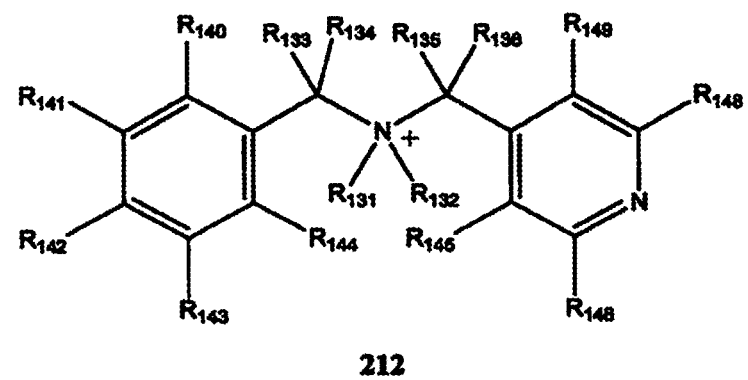

Referring to FIG. 27, compound 208, substituents $R_{111}$-$R_{116}$, $R_{120}$-$R_{127}$, $R_{129}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 27, compound 210, substituents $R_{131}$, $R_{133}$-$R_{136}$, $R_{140}$-$R_{146}$, $R_{148}$, $R_{149}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 27, compound 212, substituents $R_{131}$-$R_{136}$, $R_{140}$-$R_{146}$, $R_{148}$, $R_{149}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Figure 28:
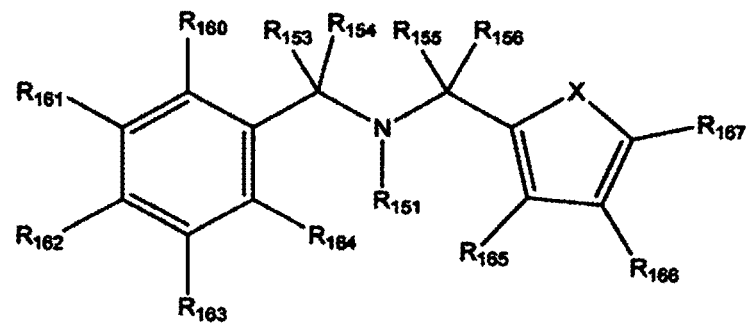
Figure 28:
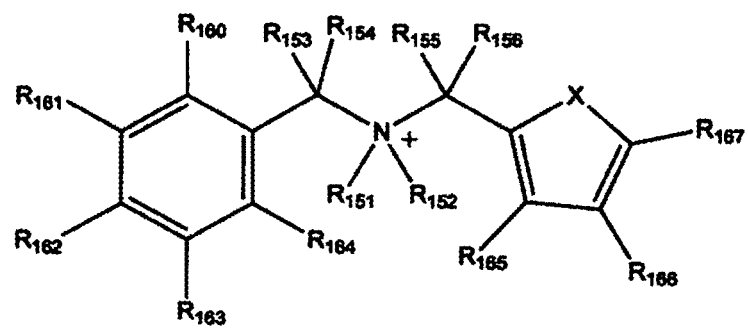
Figure 28:
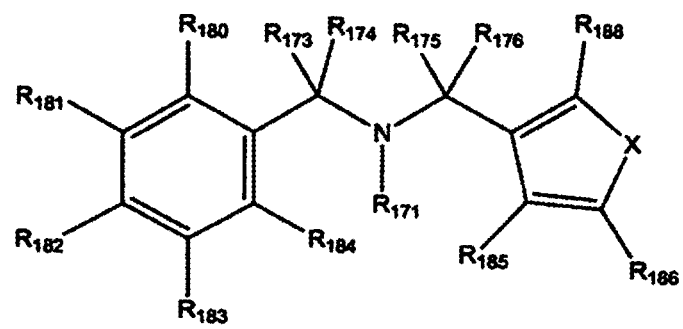

Referring to FIG. 28, compound 214, substituents $R_{151}$, $R_{153}$-$R_{156}$, $R_{163}$-$R_{167}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon. "X" is O, S or NR where R is hydrogen or alkyl.

Referring to FIG. 28, compound 216, substituents $R_{151}$-$R_{156}$, $R_{163}$-$R_{167}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon. "X" is O, S or NR where R is hydrogen or alkyl.

Referring to FIG. 28, compound 218, substituents $R_{171}$, $R_{173}$-$R_{176}$, $R_{180}$-186, $R_{188}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon. "X" is O, S or NR where R is hydrogen or alkyl.

Figure 29:
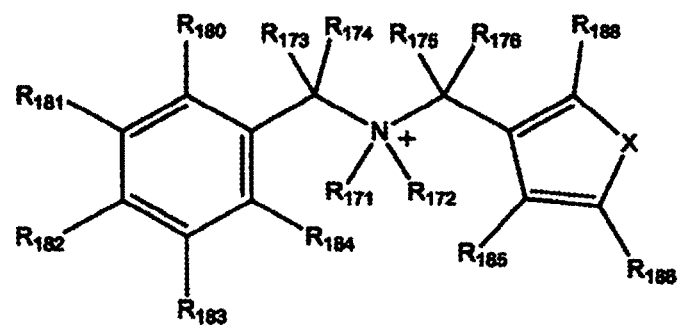
Figure 29:
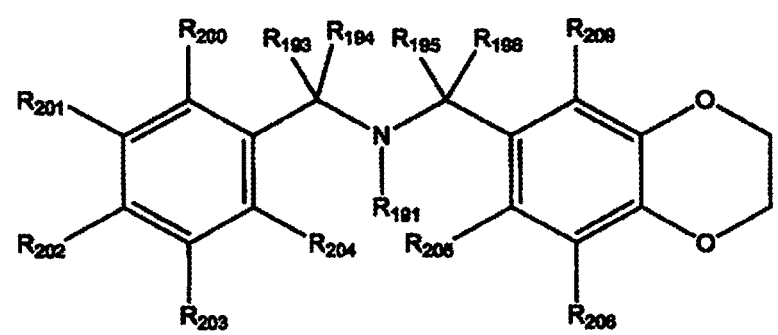
Figure 29:
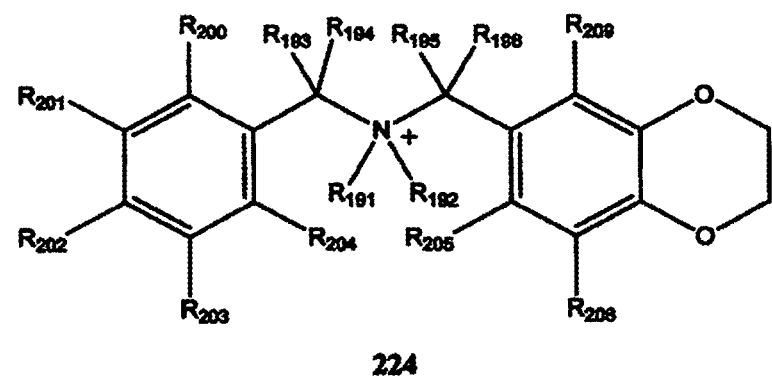
Figure 30:
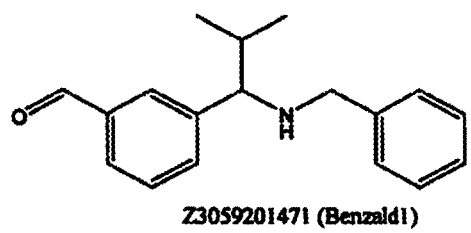
FIGS. 30-34 show further compounds according to the present invention for the treatment of ALS or a related disease.
Figure 30:
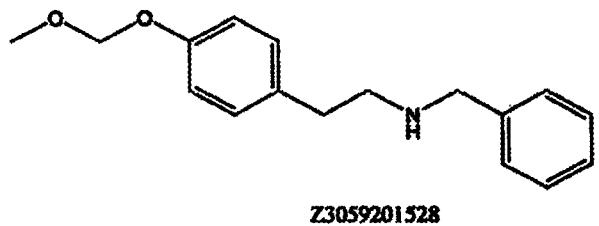
Figure 30:
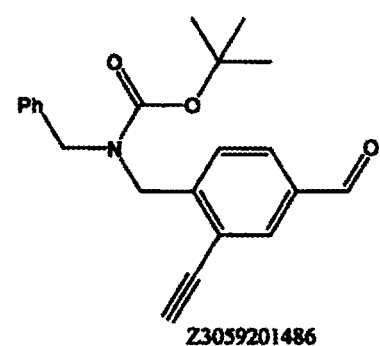
Figure 30:
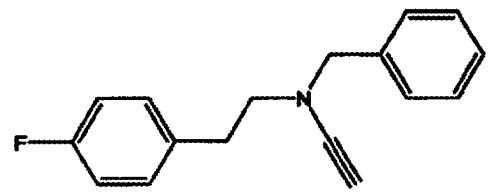
Figure 30:
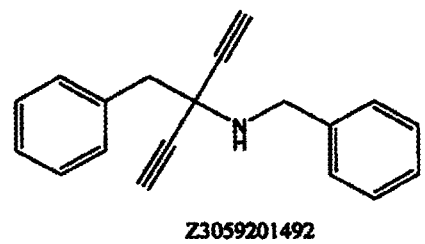
Figure 30:
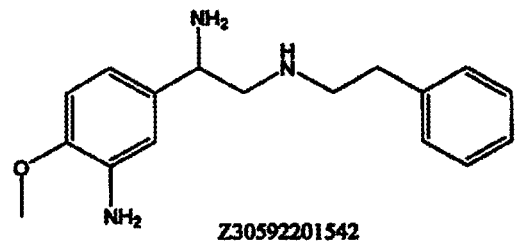
Figure 30:
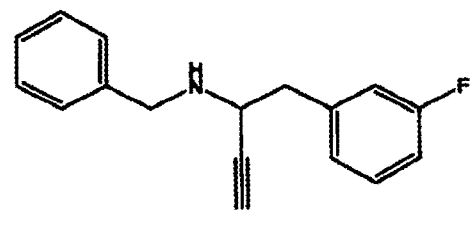
Figure 30:
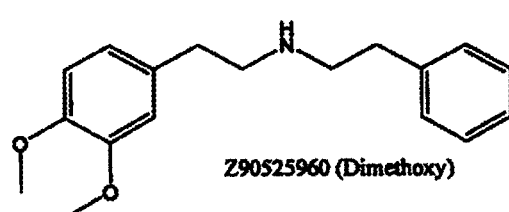
Figure 30:
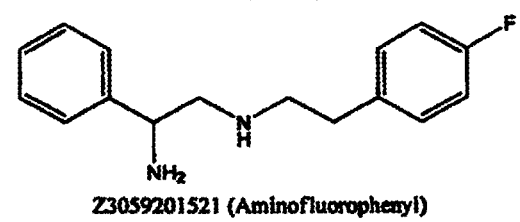
Figure 30:
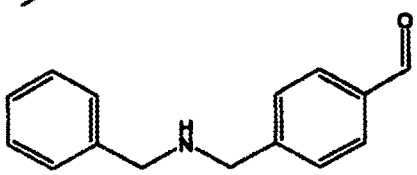
Figure 31:
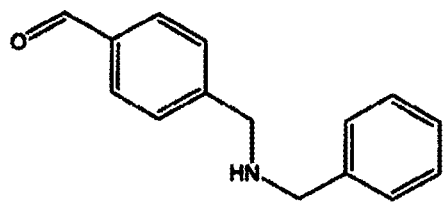
Figure 31:
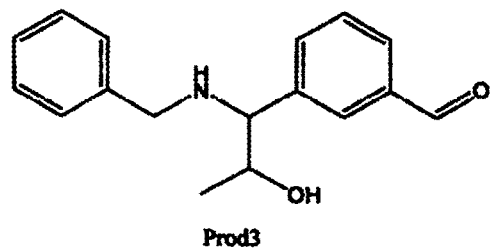
Figure 31:
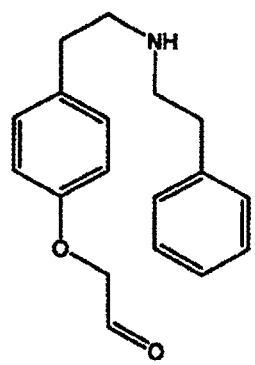
Figure 31:
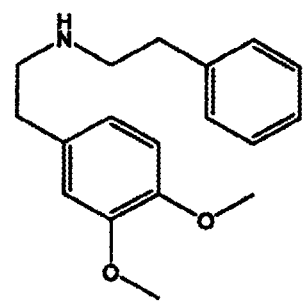
Figure 31:
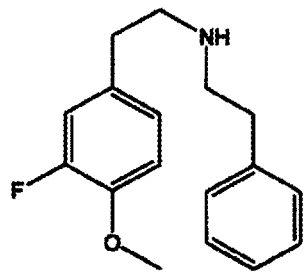
Figure 31:
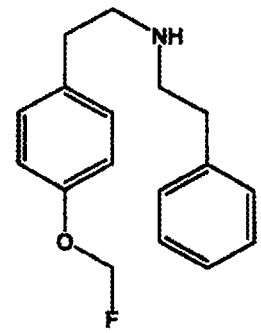
Figure 31:
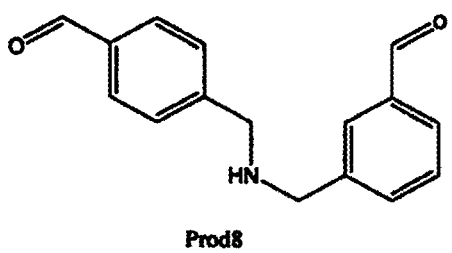
Figure 31:
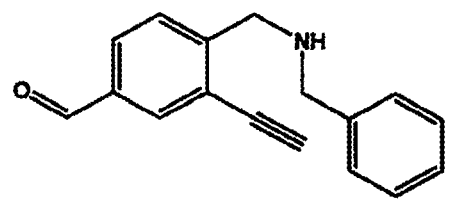
Figure 32:
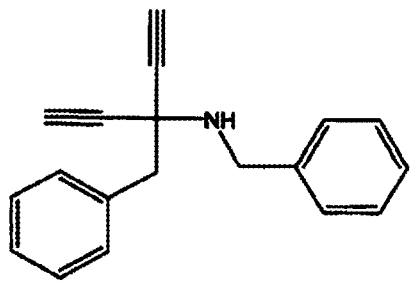
Figure 32:
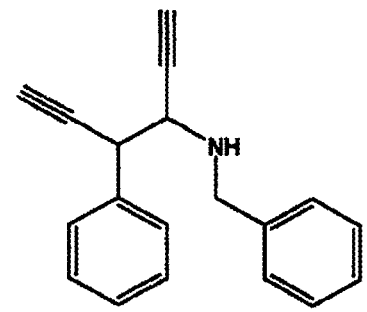
Figure 32:
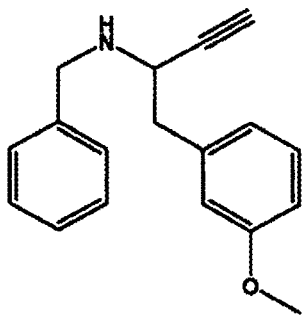
Figure 32:
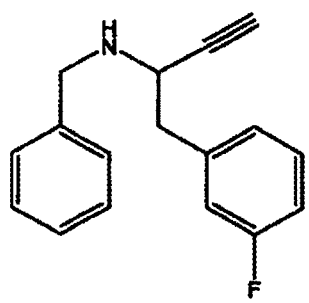
Figure 32:
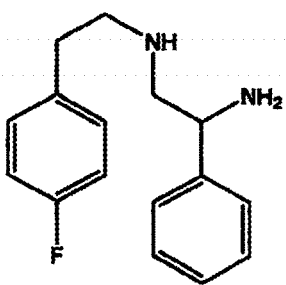
Figure 32:
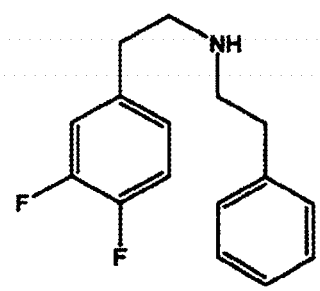
Figure 32:
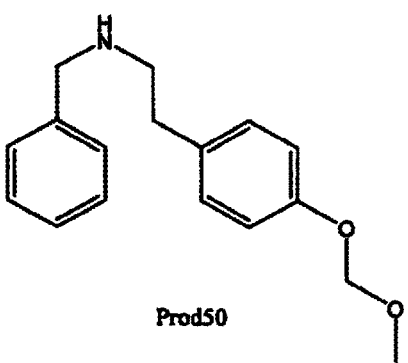
Figure 32:
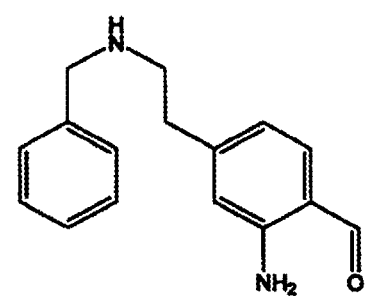
Figure 33:
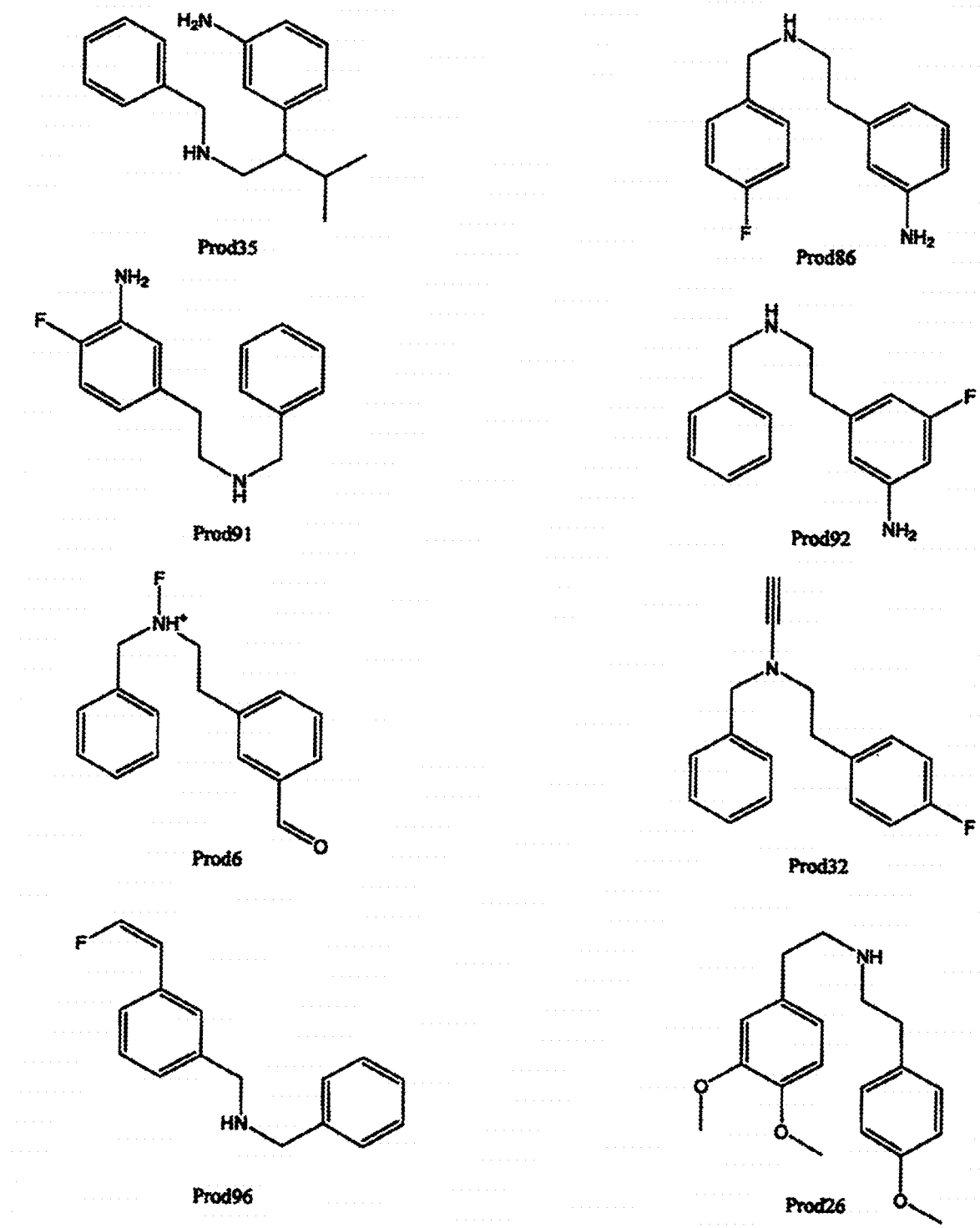
Figure 34:
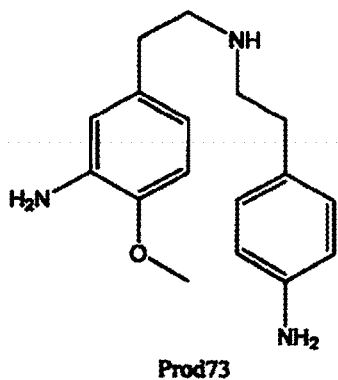
Figure 34:
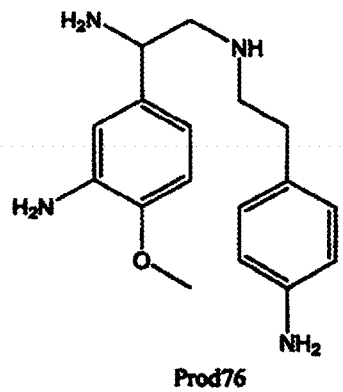
Figure 34:
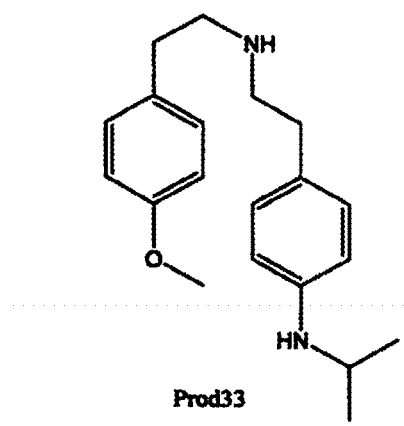
Figure 34:
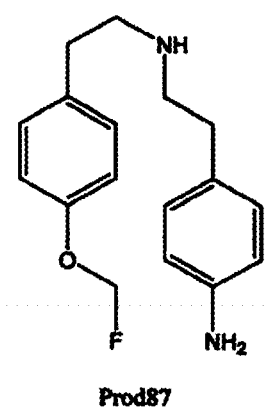
Figure 34:
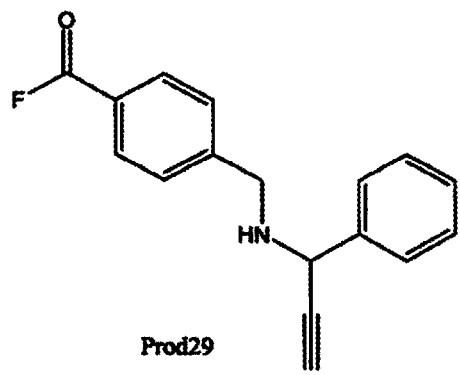
Figure 35:
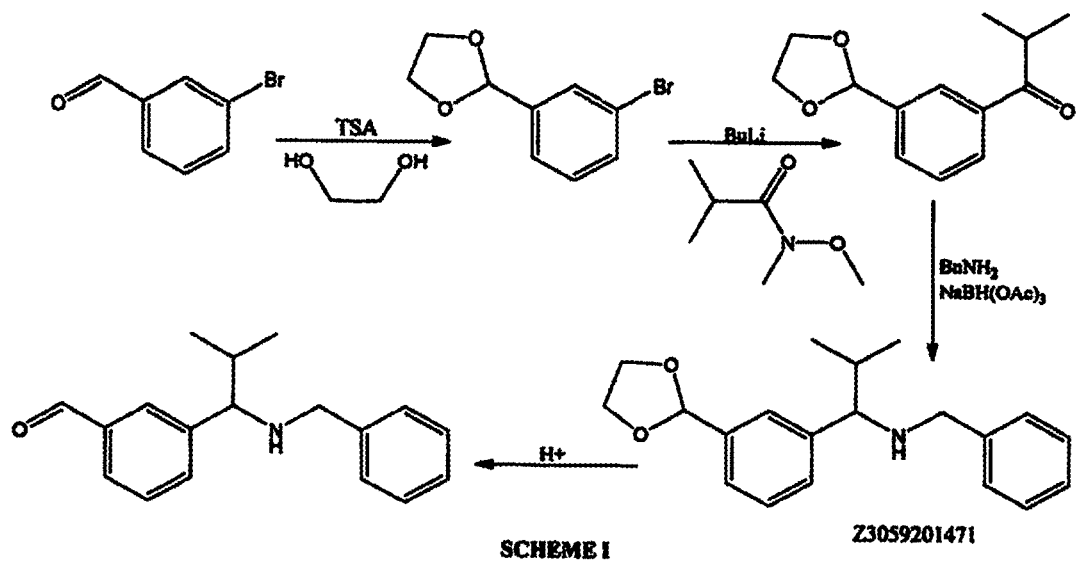
FIGS. 35-40 show synthetic schemes to make certain compounds according to the present invention.
Figure 35:
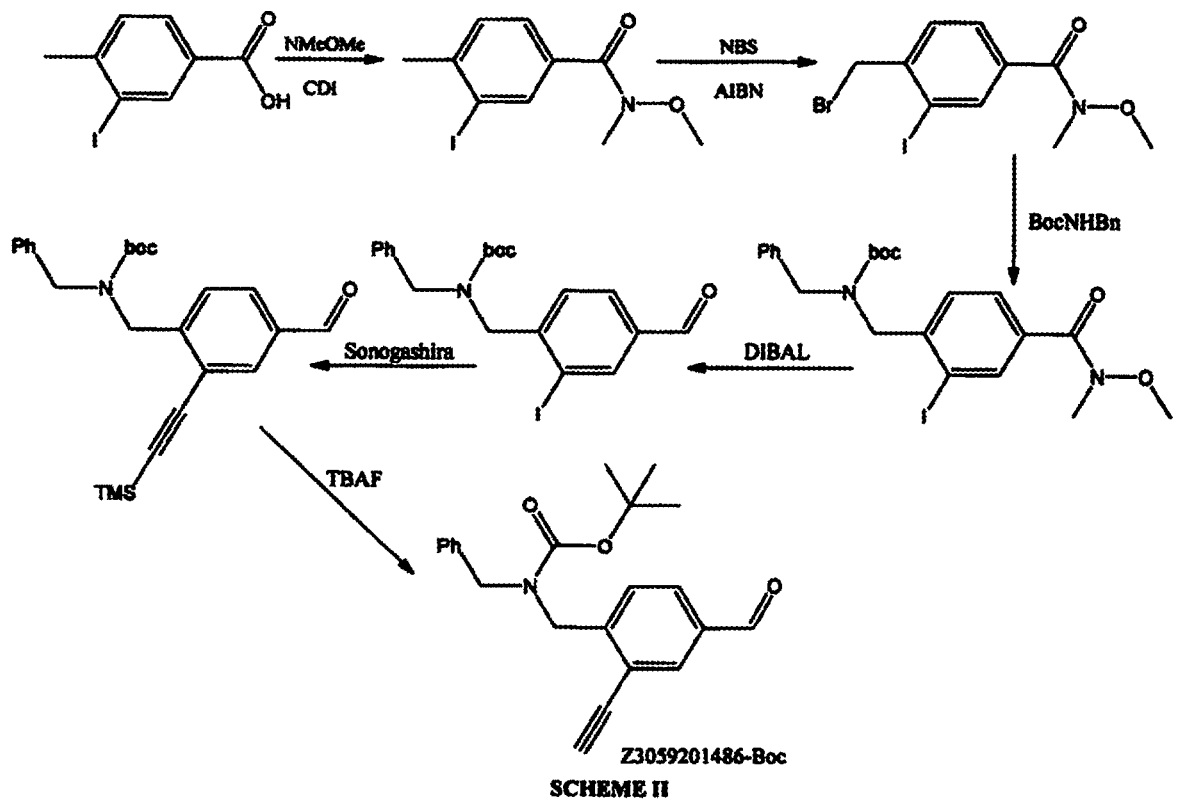
Figure 36:
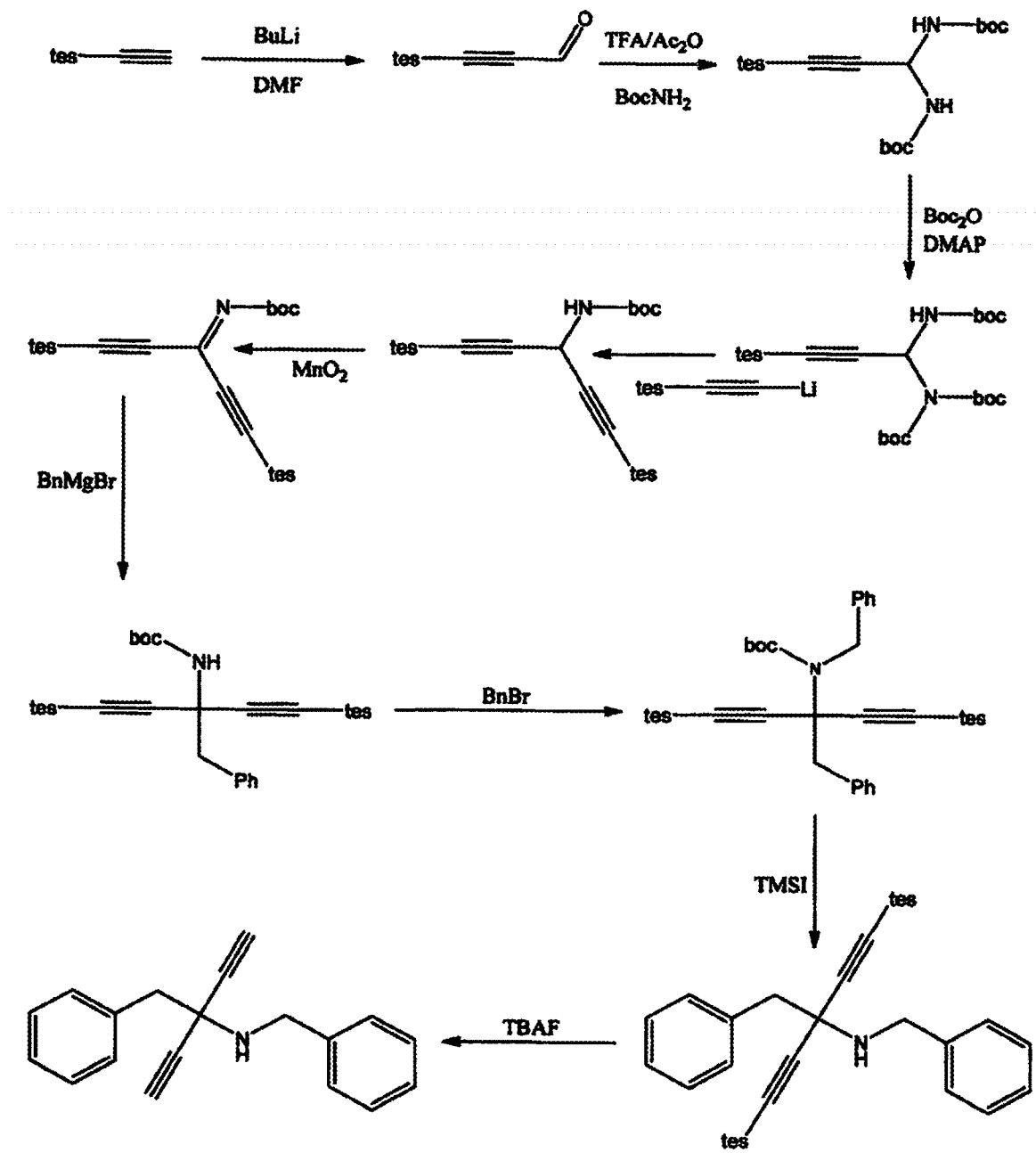
Figure 37:
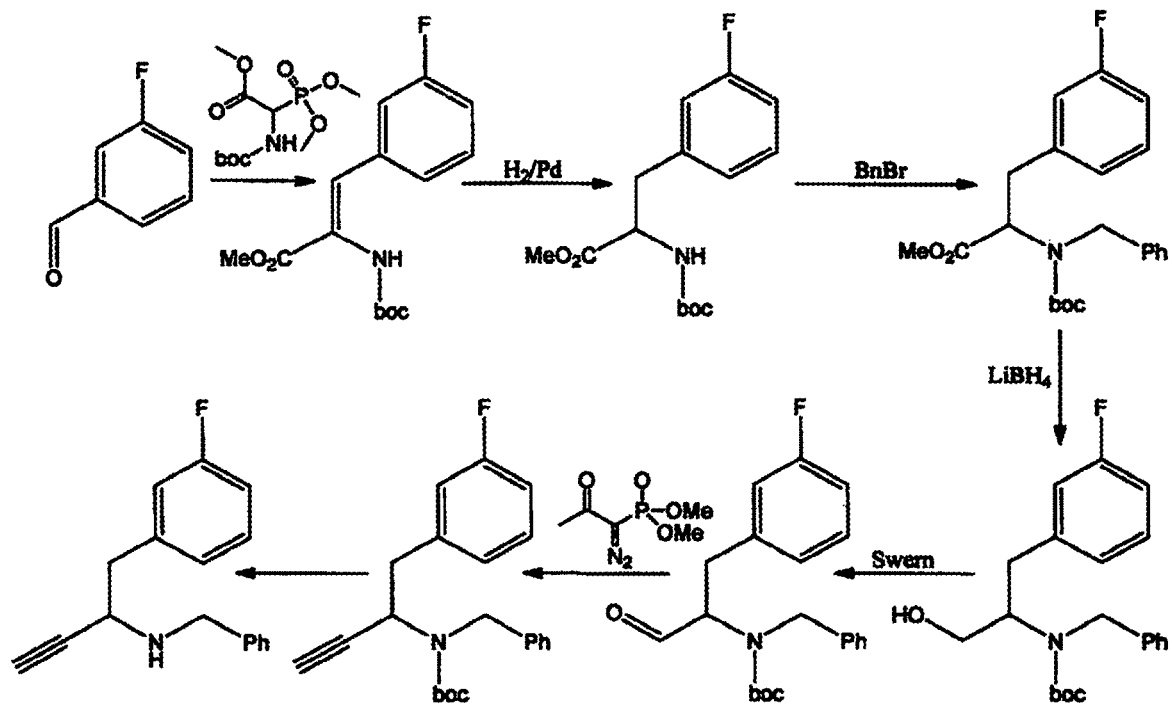
Figure 37:
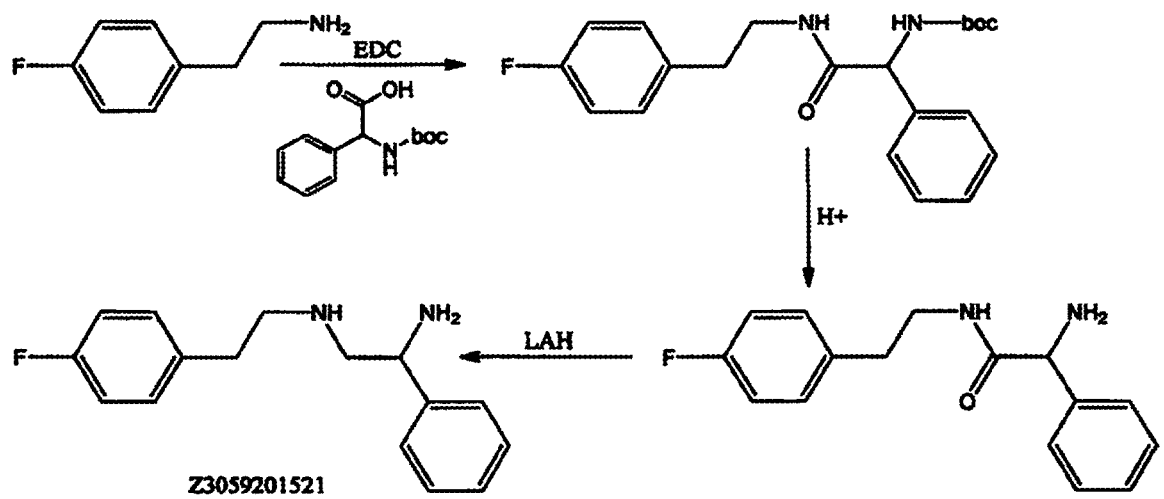
Figure 38:
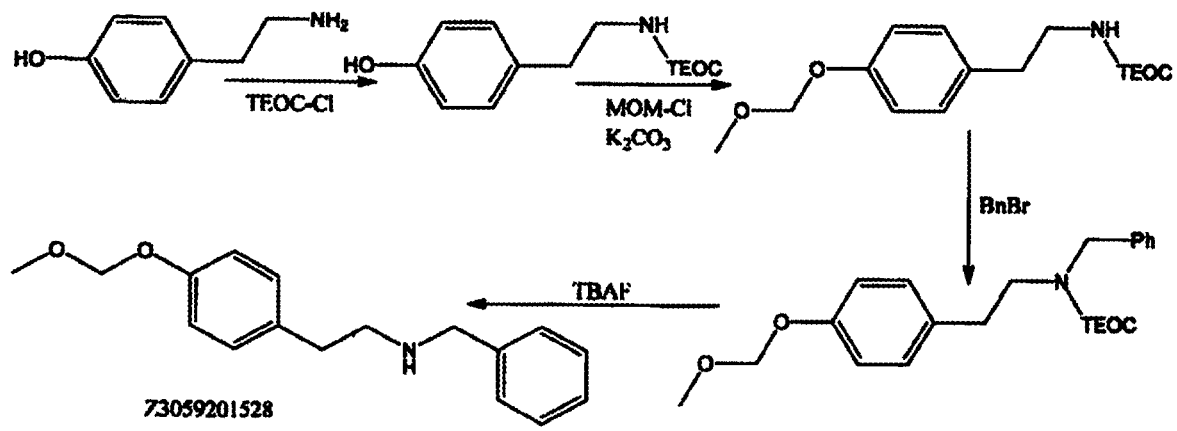
Figure 38:
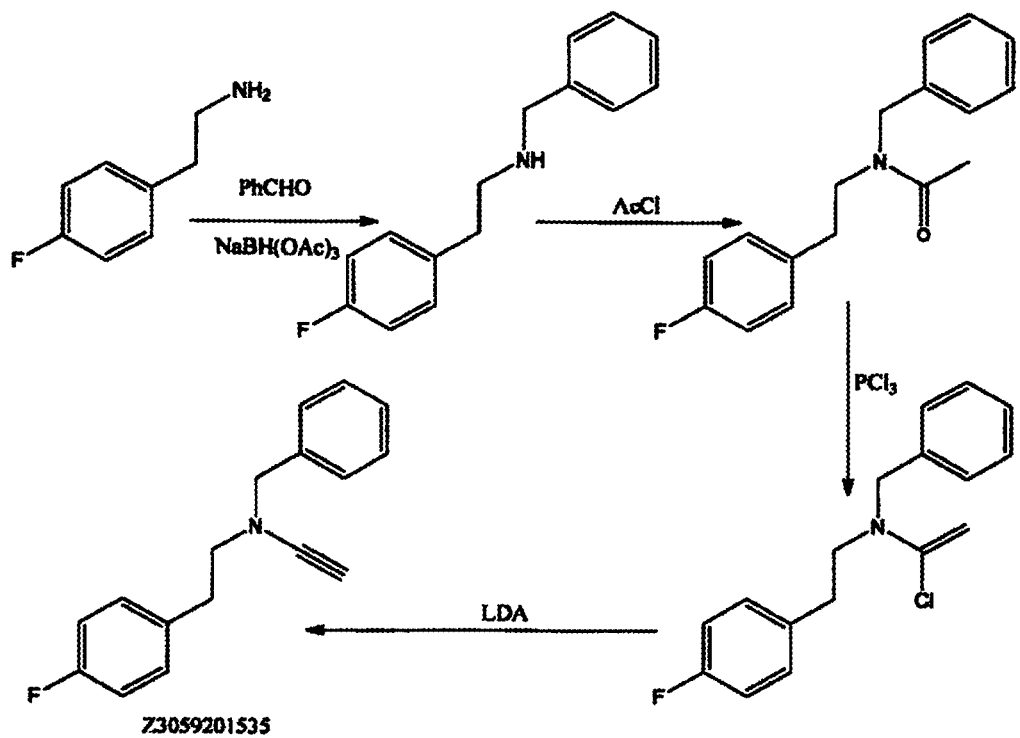
Figure 39:
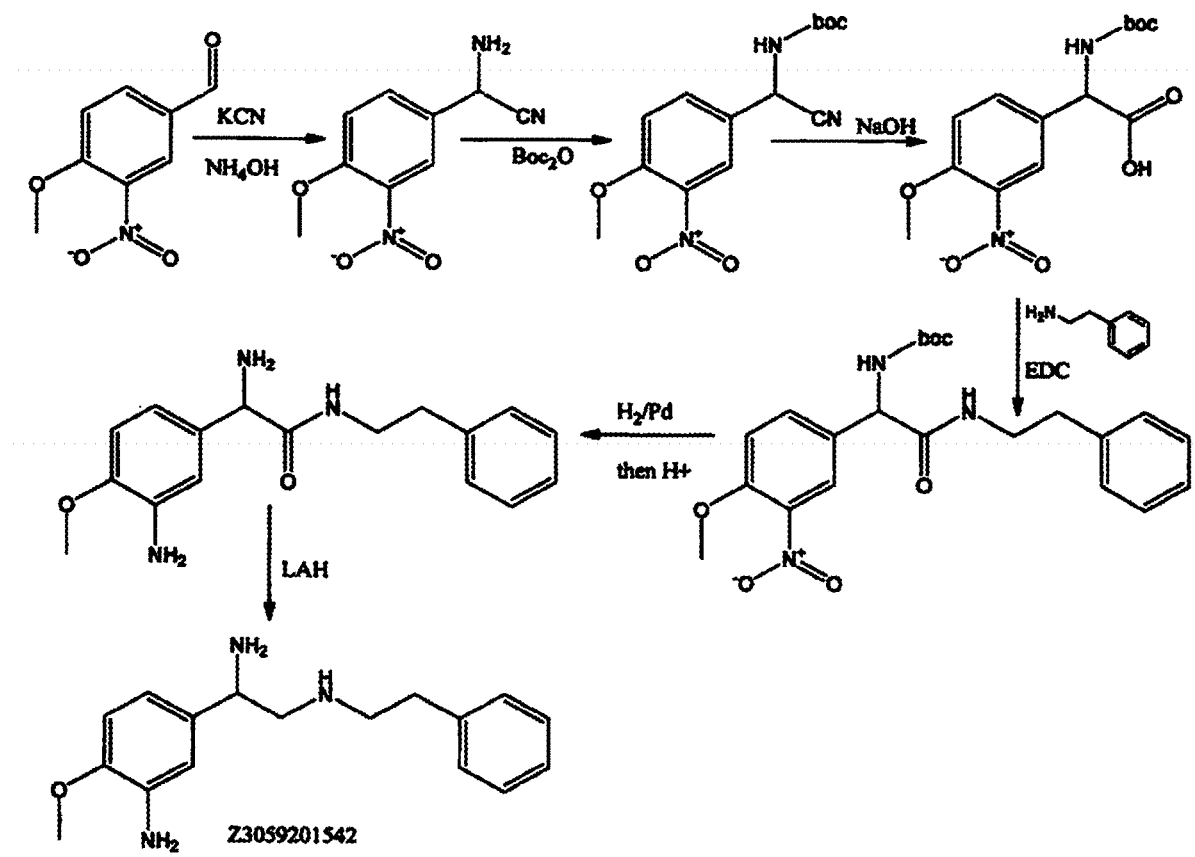
Figure 39:
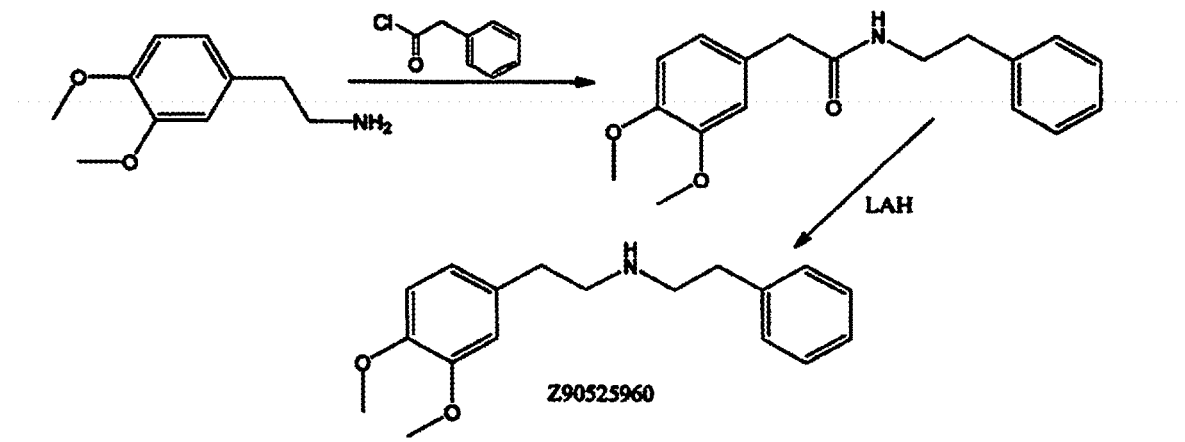
Figure 40:
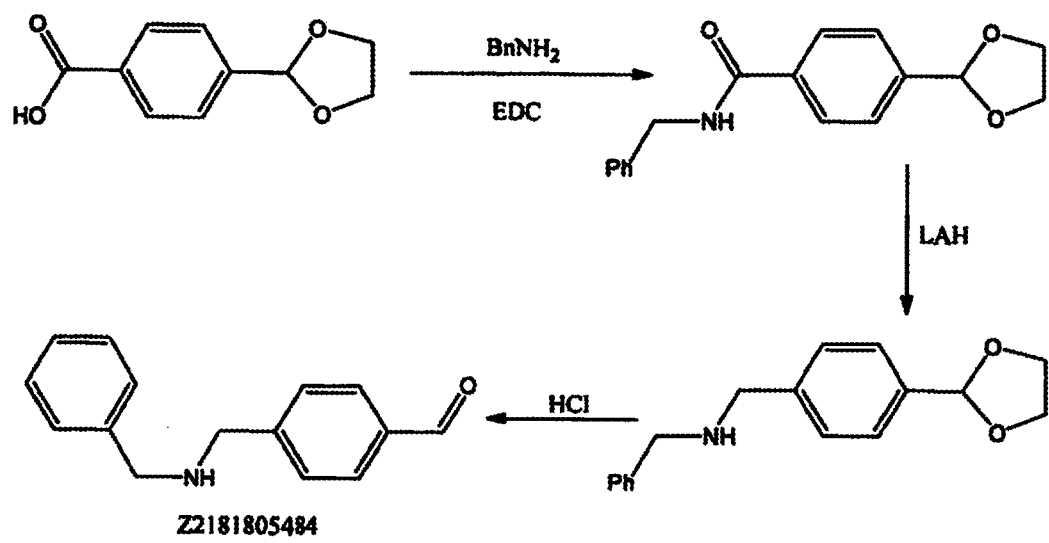
Figure 41:
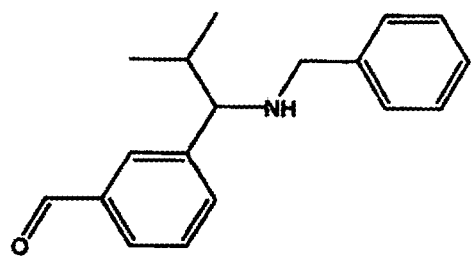
FIG. 41 shows Benzald1, Fluorophenyl, Aminofluorophenyl, Dimethoxy, Verapamil, and Dobutamine.
Figure 41:
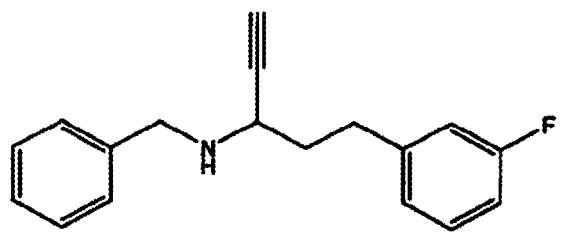
Figure 41:
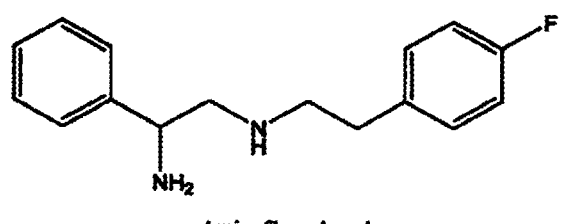
Figure 41:
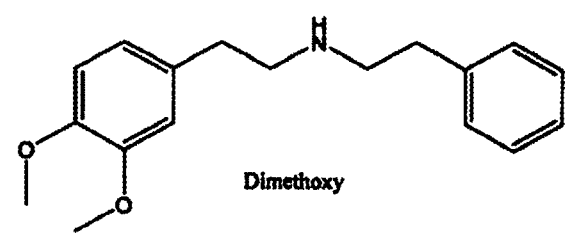
Figure 41:
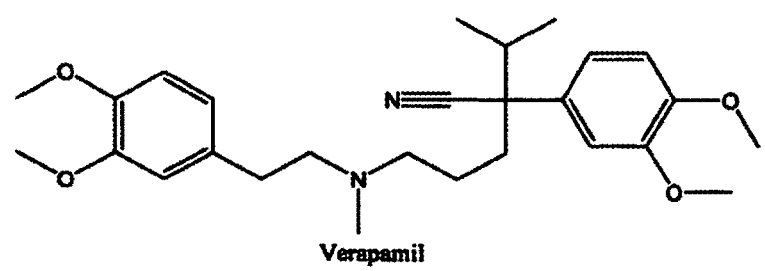
Figure 41:
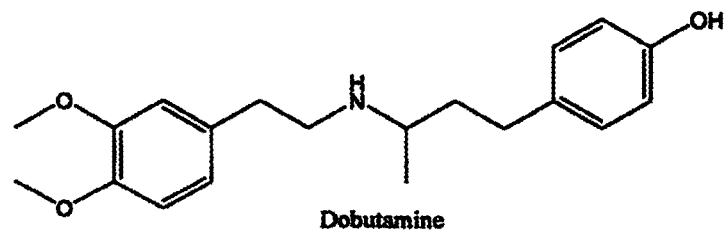

Referring to FIG. 29, compound 220, substituents $R_{171}$-$R_{176}$, $R_{180}$-186, $R_{188}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon. "X" is O, S or NR where R is hydrogen or alkyl.

Referring to FIG. 29, compound 222, substituents $R_{191}$, $R_{193}$-$R_{196}$, $R_{200}$-$R_{206}$, $R_{209}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 29, compound 224, substituents $R_{191}$-$R_{196}$, $R_{200}$-$R_{206}$, $R_{209}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Other, nonlimiting examples of compound according to the present invention for the treatment of ALS, LATE, Huntington's Disease, Parkinson's Disease, Corticobasal Degeneration, Progressive Supranuclear Palsy, CTE, Frontotemporaral Dementia and/or Related Motor neuron diseases include: N-[4-({[2-(3-chlorophenyl)ethyl]amino}methyl)-phenyl]acetamide (AC0101); (2,3-dihydro-1,4-benzodioxin-6-ylmethyl)({4 [(dimethylamino)-methyl]phenyl}methyl)amine (AC0102); 2-[4-(4-hydroxyphenyl)piperazin-1-yl]-N,N-dimethyl-2 phenylacetamide (AC0103); 3-[({[4-(morpholin-4 ylmethyl)phenyl]methyl}-amino)methyl]benzonitrile (AC0104); 4-({[3-(1-pyrrolidinylmethyl)benzyl]amino}methyl)-benzonitrile (AC0105); 4-{1-[(5-methyl-1,2-oxazol-3-yl)methyl]-1,2,3,6 tetrahydropyridin-4-yl}phenol (A0106); 4-[({[3-(pyrrolidin-1-ylmethyl)phenyl]methyl}amino)methyl]-benzonitrile (AC0107); AC0201; AC0202; AC0203; and AC0204.

CERTAIN EMBODIMENTS

A compound of the following structure:

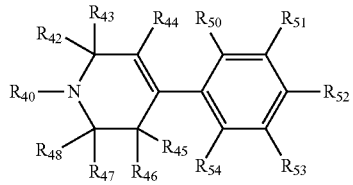

wherein $R_{40}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{42}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{43}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{44}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{45}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{46}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{47}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{48}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{50}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{51}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{52}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{53}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{54}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

The compound wherein $R_{40}$ is hydrogen, alkyl or acyl.

The compound wherein $R_{42}$, $R_{43}$, $R_{47}$ and $R_{48}$ are independently hydrogen or alkyl.

The compound wherein $R_{44}$-$R_{46}$ is hydrogen or alkyl.

The compound wherein $R_{50}$-$R_{54}$ is hydrogen, alkyl or halogen.

A method of treating or preventing ALS, LATE, Huntington's Disease, Parkinson's Disease, Corticobasal Degeneration, Progressive Supranuclear Palsy, CTE, Frontotemporal Dementia and/or Related Motor Neuron Diseases using the preceding compound.

A method of reducing or preventing formation of TDP-43, alpha-synuclein, Huntingtin's protein and/or tau protein oligomers using the preceding compound.

A compound of the following structure:

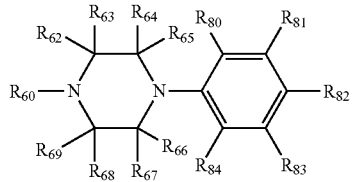

wherein $R_{60}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{62}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{63}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{64}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{65}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{66}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{67}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{68}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{69}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{80}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

R<sub>81</sub> is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{82}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{83}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon; and $R_{84}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

The compound wherein $R_{60}$ is hydrogen, alkyl or acyl.

The compound wherein $R_{62}$, $R_{63}$, $R_{68}$ and $R_{69}$ are independently hydrogen or alkyl.

The compound wherein $R_{64}$, $R_{65}$, $R_{66}$ and $R_{67}$ are independently hydrogen or alkyl.

The compound wherein $R_{80}$-$R_{84}$ are independently hydrogen, alkyl or halogen.

A method of treating or preventing ALS, LATE, Huntington's Disease, Parkinson's Disease, Alzheimer's, Corticobasal Degeneration, Progressive Supranuclear Palsy, CTE, Frontotemporaral Dementia and/or Related Motor Neuron Diseases using the preceding compound.

A method of reducing or preventing formation of TDP-43, alpha-synuclein, Huntingtin's protein and/or tau protein oligomers using the preceding compound.

A method of reducing formation of or disrupting TDP-43, alpha-synuclein, Huntingtin's protein and/or tau protein oligomers in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, Benzald1, Fluorophenyl, Aminofluorophenyl, and Dimethoxy.

A method of treating or preventing ALS in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, Benzald1, Fluorophenyl, Aminofluorophenyl, and Dimethoxy.

A method of treating or preventing LATE in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, Benzald1, Fluorophenyl, Aminofluorophenyl, and Dimethoxy.

A method of treating Huntington's disease in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, Benzald1, Fluorophenyl, Aminofluorophenyl, and Dimethoxy.

A method of treating or preventing Parkinson's disease in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, Benzald1, Fluorophenyl, Aminofluorophenyl, and Dimethoxy.

A method of treating or preventing corticobasal degeneration in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, Benzald1, Fluorophenyl, Aminofluorophenyl, and Dimethoxy.

A method of treating or preventing progressive supranuclear palsy in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, Benzald1, Fluorophenyl, Aminofluorophenyl, and Dimethoxy.

A method of treating or preventing CTE in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, Benzald1, Fluorophenyl, Aminofluorophenyl, and Dimethoxy.

A method of treating or preventing frontotemporal dementia in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, Benzald1, Fluorophenyl, Aminofluorophenyl, and Dimethoxy.

Certain Compounds of the Invention

Experimental Section—Cellular Assays

INTRODUCTION

Amyotrophic lateral sclerosis (ALS) is one of the most common degenerative diseases of the motor neuron system. TDP-43 related pathologies seem to be a dominant type of pathologies across sporadic ALS types. A novel fluorescence cell-based assay for High Content Screening that allows the quantification of pathological TDP43 granules has been developed. In this work we have used this model to screen the effects of three compounds, using Riluzole as a positive control. The TDP-43 U2OS cell line contains U2OS cells stably expressing the tGFP tagged human TDP-43. This cell line has been designed to test compounds and to analyse their capability to modulate TDP43 granule formation after cytotoxic stress induction. The cell line was generated in Innoprot. It is a stable cell line that express the LacRI repressor protein and the TDP43-turboGFP protein. The cell line was generated using the pCMVLacRI-Hygro plasmid (Hygromycin resistance) and the pPuro-TDP43tGFP plasmid (that confers the puromycin resistance). The cell line was generated transfecting these plasmids with Lipofectamine LTX reagent, and the transfected cells were diluted until critical dilution. The negative control show a diffuse nuclear distribution of the fluorescence, but after sodium arsenite treatment the phenotype turns into a cyto-

| ID # | CAS# | Chemical name |
|---|---|---|
| AC0101 | 1209424-09-8 | N-[4-({[2-(3-chlorophenyl)ethyl]amino}methyl)phenyl]acetamide |
| AC0102 | 1014247-57-4 | (2,3-dihydro-1,4-benzodioxin-6-ylmethyl)({4[(dimethylamino)methyl]-phenyl}methyl)amine |
| AC0103 | 1214022-77-1 | 2-[4-(4-hydroxyphenyl)piperazin-1-yl]-N,N-dimethyl-2 phenylacetamide |
| AC0104 | 1241566-06-2 | 3-[({[4-(morpholin-4 ylmethyl)phenyl]methyl}amino)methyl]benzonitrile |
| AC0105 | 1241332-16-0 1384724-10-0 | 4-[({[4-(pyrrolidin-1 ylmethyl)phenyl]methyl}amino)methyl]benzonitrile |
| AC0106 | 1311839-93-6 | 4-{1-[(5-methyl-1,2-oxazol-3-yl)methyl]-1,2,3,6 tetrahydropyridin-4-yl}phenol |
| AC0107 | 1355835-03-8 1384715-28-9, | 4-[({[3-(pyrrolidin-1-ylmethyl)phenyl]methyl}amino)methyl]benzonitrile |
| AC0201 | | |
| AC0202 | | |
| AC0203 | | |
| AC0204 | | |

Three different assays have been performed regarding the activity of compounds AC0101-AC0107 and AC0201-AC0204. The first is a computational assay. The second is a cellular based assay directed to TDP43 granule formation inhibition in cells after arsenite treatment. The third utilized IM-MS to monitor the oligomerization of TDP-43307-319 in the presence of molecules.

Experimental Section—Computational Methods

The molecules AC0101-AC0107, AC0201-AC0204, and their derivatives have been discovered and assessed to be active against the proteins through computational methods. Essentially, a machine learning model was trained using a set of positives and negatives and was used to predict activities of molecules from a chosen subspace. The computational actives may be subjected to further assays, such as IM-MS. Mechanistically, it is widely held that intrinsically disordered, aggregation prone proteins (for example, tau, TDP-43, alpha-synuclein) adopt prion-like properties. Upon transmission from the donor cell to the recipient cell, the prion-like transferred protein serves to template and thereby corrupt the endogenous protein, which serves to spread the toxic oligomeric/aggregated state from cell to cell. We utilize this aspect in the design of molecules that can affect many proteins.

solic vesicular pattern corresponding to stress granules and into an intensive nuclear granules pattern. The aim of this work was to assess different doses of 11 compounds.

AIM

The objective of these experiments was to screen the protective effect of 11 compounds and reference compound (arimoclomol) against cellular oxidative stress induced by sodium arsenite (i.e., arsenite). The compounds have been tested at 10 µM, 5 M, 2 µM and 1 µM each, and appropriate controls (vehicle, arsenite and controls) have been included as well. The compound tested were the following: 101, 102, 103, 104, 105, 106, 107, 201, 202, 203 and 204.

Abbreviations

Abbreviations: nm (nanometres); nM (nanomolar); mM (millimolar); SD (Standard Deviation); DMEM (Dulbecco's Modified Eagle Medium); Opti-MEM (Opti-Minimal Essential Medium); FBS (Fetal Bovine Serum); DMSO (Dimethyl sulfoxide).

Materials and Methods

U2OS cells from CLS company reference no. 300364; DMEM-F12 (Sigma-Aldrich D6421, batch RNBG7141);

Opti-MEM (Thermo-Fisher scientific 31985070, batch 1932076); FBS (Sigma-Aldrich F2442, batch BCBW6329); IPTG (Sigma Aldrich I5502, batch 077M4016V); Flat bottom black 96-well plates (Becton Dickinson 353219, batch E1804340); Arimoclomol (Sequoia, batch 067897776); Sodium arsenite solution (Sigma Aldrich 35000 Fluka, bach HC85455377); Cell Insight High-Content Bioimager CX7 from Thermofisher.

Compound Dissolution

Each compound was prepared in Optimem. In the final dilution, DMSO was added in order to obtain a final DMSO concentration of 0.1$, the same that the reference compound (arimoclomol). All compounds were tested at 0.1% DMSO (vehicle) final concentration.

Methods

Day 1 (Thursday). Recombinant TDP43-tGFP-U2OS cell line was thawed (2×106 cells per T75). Day 2 (Friday). After 24 hours, Cells were maintained in DMEM-F12 supplemented with 10% FBS at 37° C. in a humidified 5% CO2 atmosphere. Day 5 (Monday). Cells were plated in coated 96-well plates with a number of 10.000 cells (+/−2000 cells) per well. Cells were maintained in DMEM-F12 medium supplemented with 10% FBS for 24 h at 37° C. in a humidified 5% CO2 atmosphere. Day 6 (Tuesday). Cells were incubated with test compounds and IPTG 1 mM in triplicate assays during 24 hours. Day 7 (Wednesday). Culture medium was replaced, and cells were treated with 250 μM of sodium arsenite during 120 min and TDP-43 globs formation was quantified in both cell cytoplasm and cell nucleus. The TDP43 granules formation was quantified after the formaldehyde fixation (3.7 wt. %, 20 minutes) of the cells. The nuclei were stained using DAPI (2 μg/ml) and the fluorescence was measured using a Cell Insight High-Content Bioimager from Thermofisher. To detect the DAPI, the filters used were 380/10 and 460/10 nm for excitation and emission, respectively and to detect the TDP43 granules, the filters were 488/20 and 520/20 nm, respectively. The images were obtained with an objective of 20×, taking 9 pictures of each well. Cell quantification was performed delimitating the region of interest of the nuclei (stained with DAPI) and after quantification, the average of each triplicate was performed. Granule quantification was also performed using the Thermofisher Cellomics Scan Viewer 6.1.1. Spot detector application from Cell Software delimitated 2 regions of interest, the nuclei and cytosol. This software application quantified the number of granules per nuclei and the average granule number per cytosol of each well was calculated. After that, the average of the triplicates was performed. Both Excel 2003 and Sigmaplot 9.0 were used for data management.

Results

Before oxidative stress induction by sodium arsenite, cells were incubated with the compounds during 24 hours. Then, the nuclear granules number and the cytosol granules number was quantified using Thermofisher Cellomics Scan Viewer 6.1.1. Spot detector application from Cell Software. The ability of compound to inhibit the cytotoxic stress mediated by the sodium arsenite treatment was studied using a dose response experiment. The concentrations of compounds to be used were proposed by the sponsor.

Figure 42:
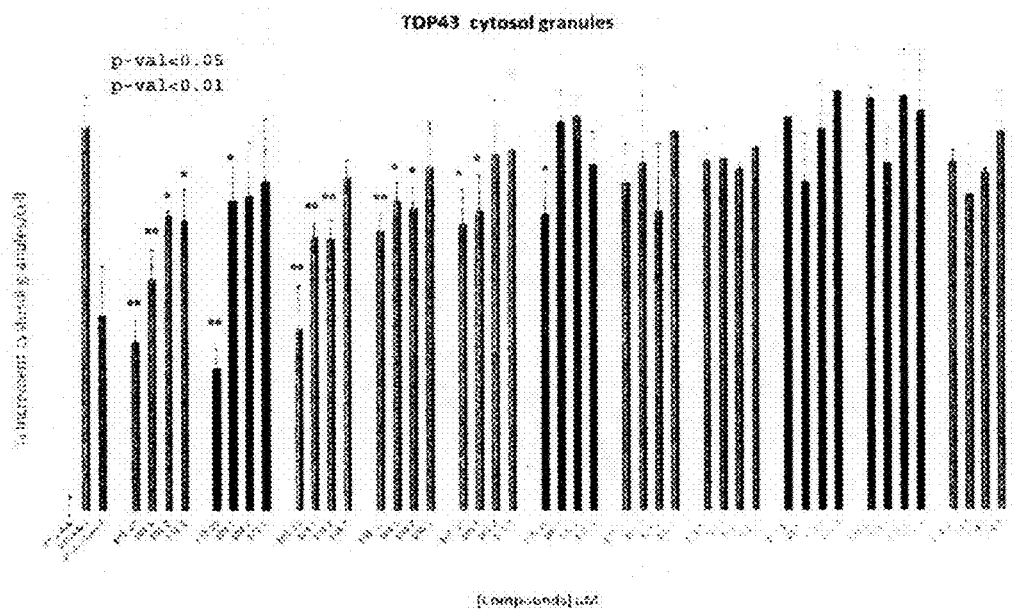
FIG. 42 shows the percentage of the cytosolic TDP43 granules increment quantification for different concentration for compounds AC0101, AC0102, AC0103, AC0104, AC0105, AC0106, AC0107, AC0201, AC0202, AC0203 and AC0204. Data points represent the mean +/−SD at each condition for a single experiment performed by triplicate. The images were obtained with an objective of 20×. 9 pictures of each well were taken. The results were normalized according to sodium arsenite and vehicle, considering sodium arsenite and vehicle as 100% and 0% respectively.
Figure 43:
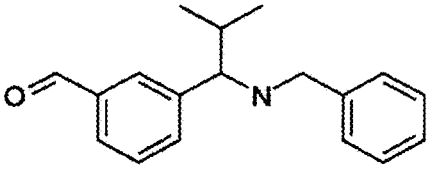
FIG. 43 shows compounds AC0201, AC0202, AC0203 and AC0204.
Figure 43:
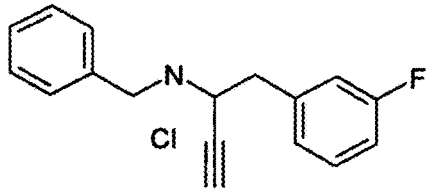
Figure 43:
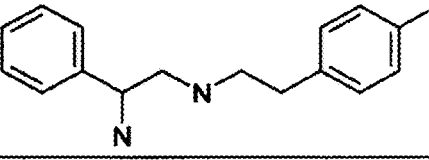
Figure 43:
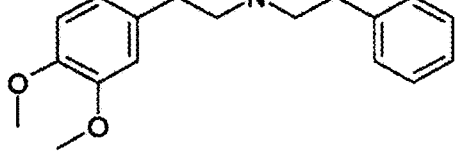
Figure 44:
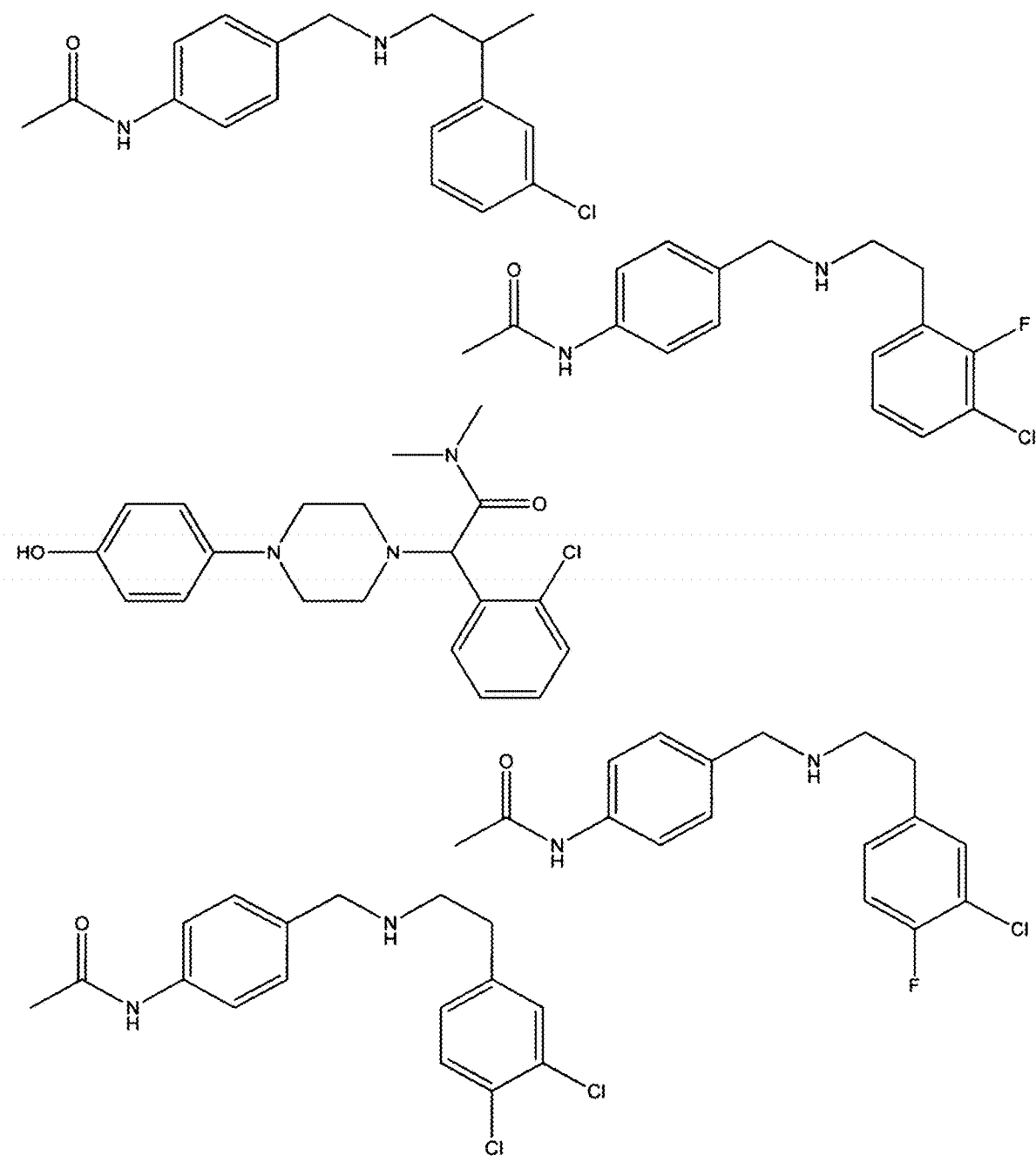
FIGS. 44-50 show further compounds according to the present invention for the treatment of ALS or a related disease.
Figure 45:
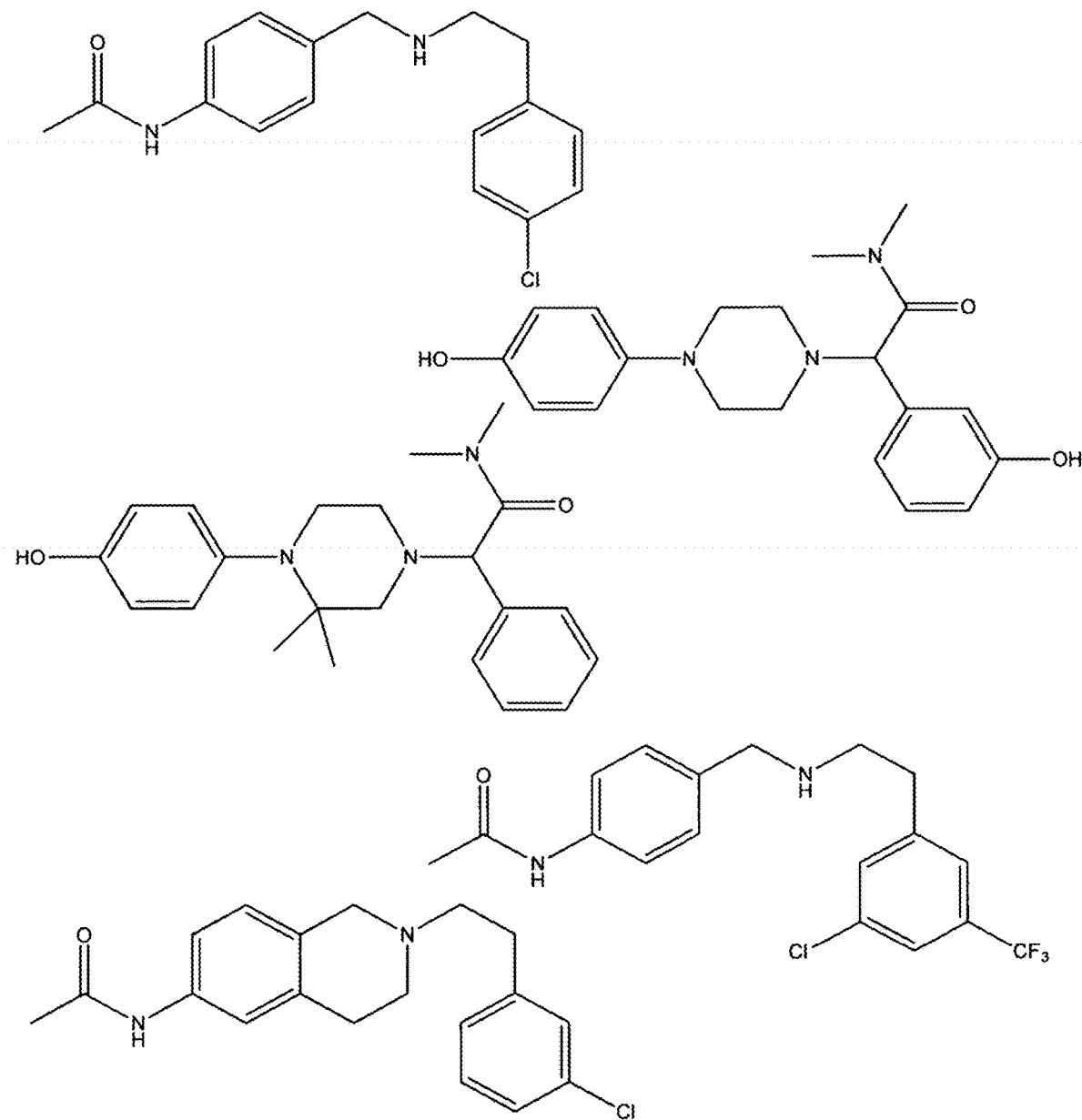
Figure 46:
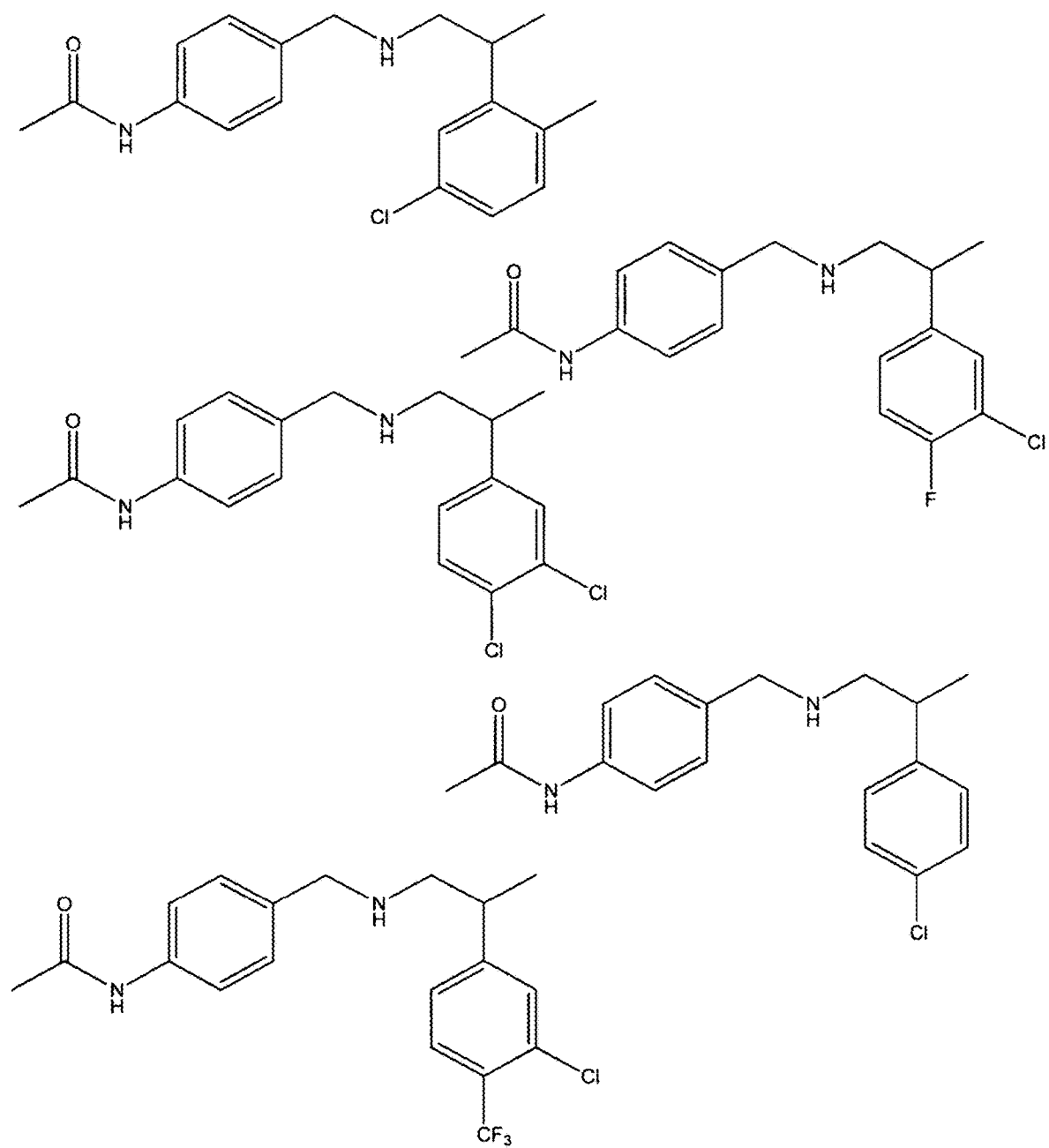
Figure 47:
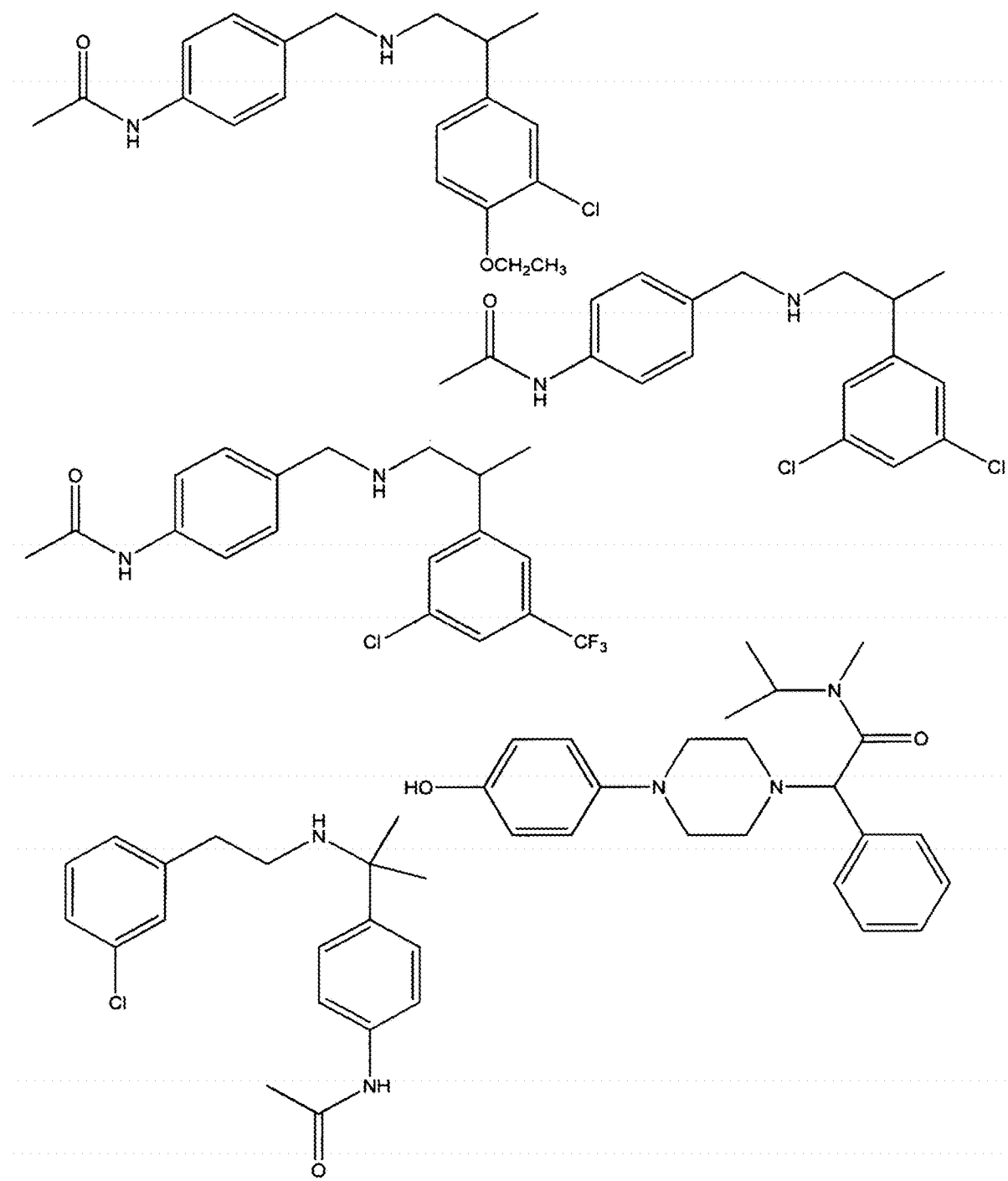
Figure 48:
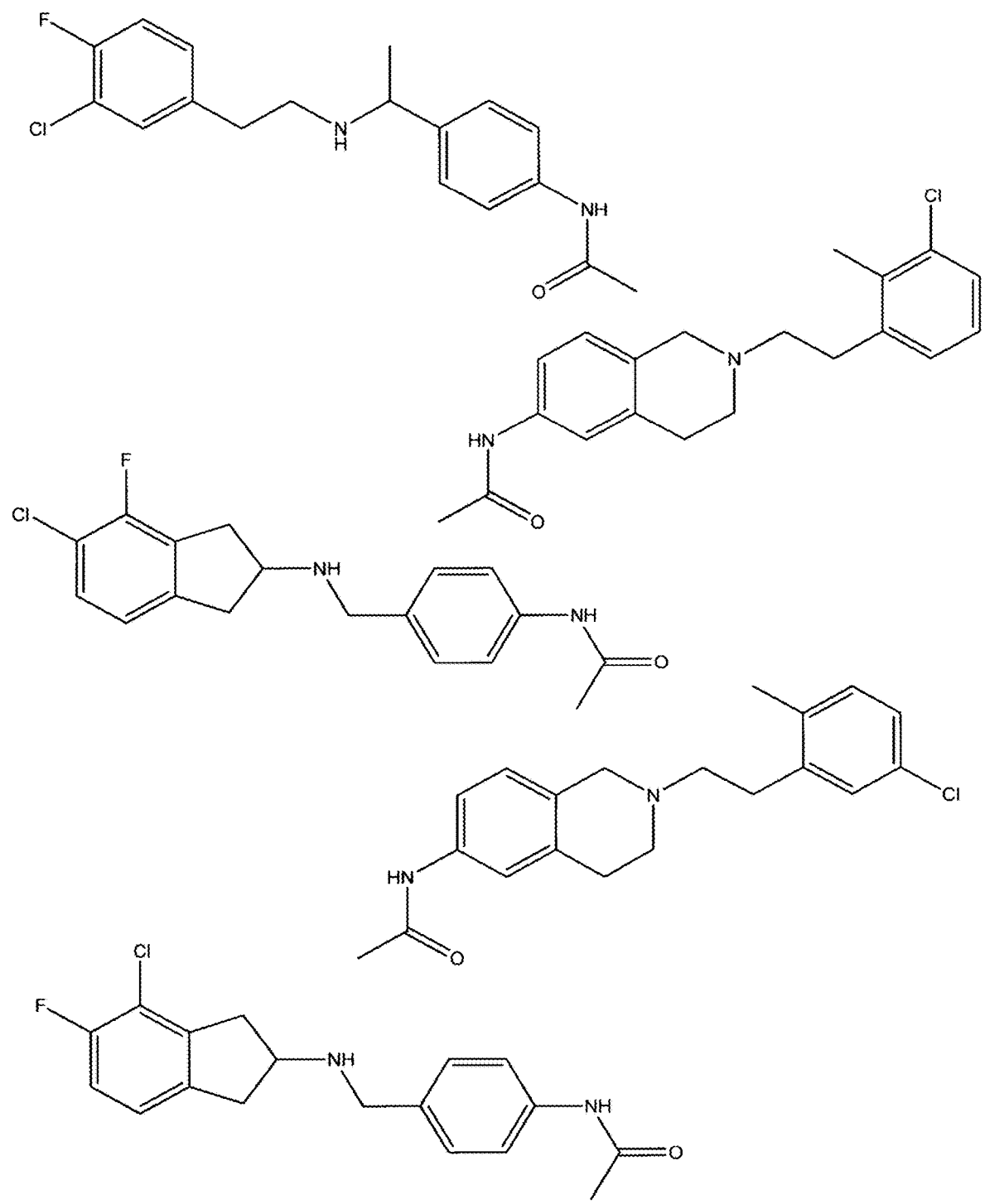
Figure 49:
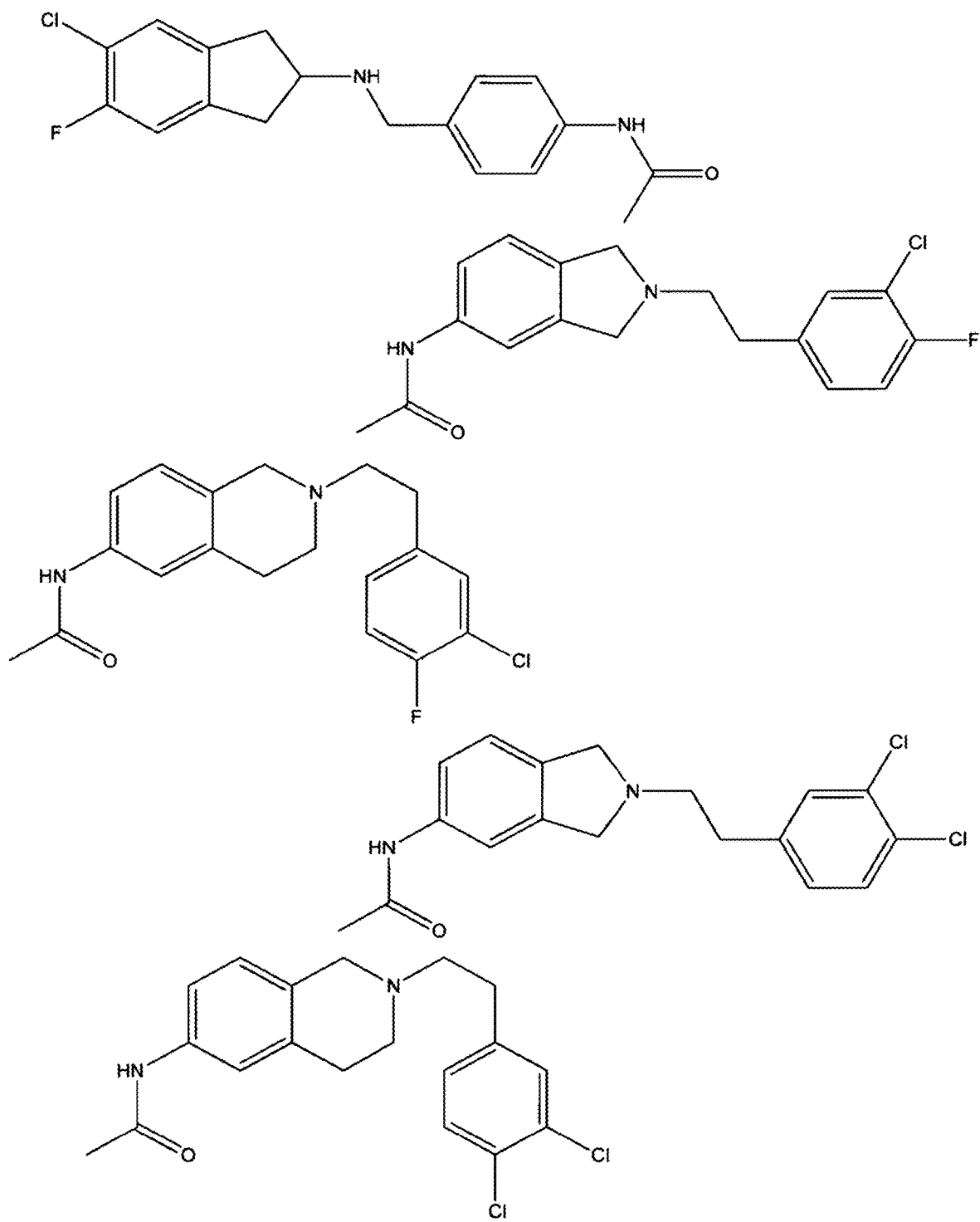
Figure 50:
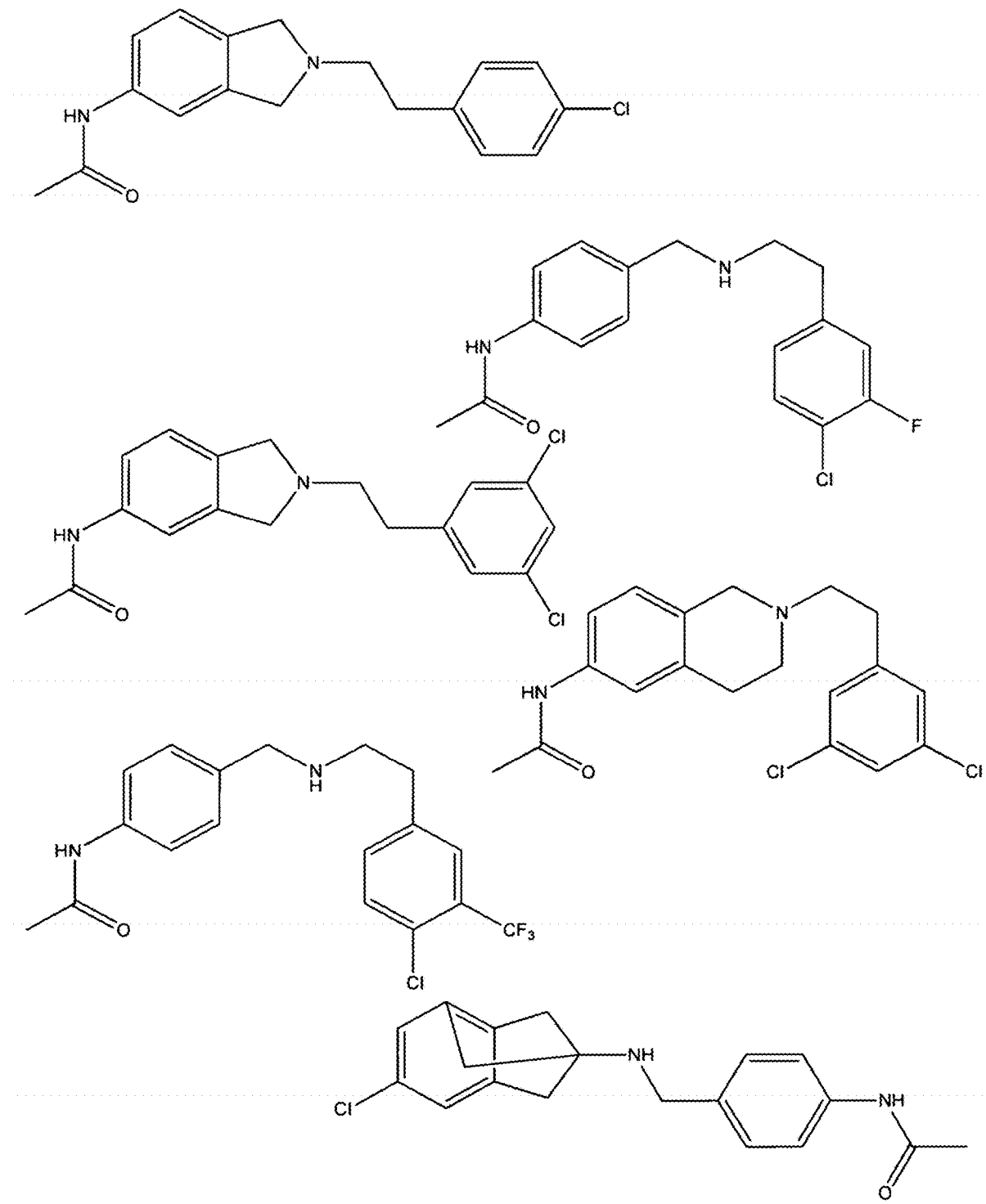

Eleven compounds were tested: AC0101-AC0107 and AC0201-AC0204. Compounds AC0101, AC0102 and AC0103 were positive in the TDP43 granule formation inhibition in cells after arsenite treatment. Compound AC0101 showed stress granule inhibition in a dose-dependent manner with a maximum of 62.47% in nucleus and 43.96% in cytosol at 5 and 10 μM, respectively. Compound AC0102 showed stress granule inhibition in a dose-dependent manner with a maximum of 27.70% in nucleus and 36.89% in cytosol at 10 μM. Compound AC0103 showed stress granule inhibition in a dose-dependent manner with a maximum of 47.20% in cytosol at 10 μM. Also, as shown in FIGS. 42, AC0104 and AC0105 were mildly active.

Experimental Section—IM-MS Assays

Materials and Methods

Peptide Synthesis and Purification. TDP-43307-319 WT peptide 307 [MGGGMNF GAFSIN]319 was synthesized using standard 9-fluorenylmethoxycarbonyl (Fmoc) chemistry using 2-(1H-benzotriazol-1-yl)-1,1,3,3-tetramethyluronium hexafluorophosphate/hydroxy-benzotriazole (HBTU/HOBT) manual solid phase peptide synthesis. The peptide was amidated with an Fmoc-Rink Amide resin (Anaspec). The peptide was cleaved from the resin using 94% TFA, 5% triisopropylsilane, and 1% phenol for 2 h at 295 K. The crude peptide was purified by reverse phase high performance liquid chromatography (RP-HPLC) on a semi-preparative C18 column (Phenomenex) using gradients of water [0.1% (v/v) TFA] and acetonitrile [0.1% (v/v) TFA]. The peptide was dissolved in 6 M guanidine hydrochloride (GdnHCl) prior to injection due to its insolubility in water and acetonitrile. The peptide purity was >93% as determined by analytical RP-HPLC. The molecular mass of the peptide was verified by ESI mass spectrometry.

Compounds: [AC0107], p-{[({[m-(1-pyrrolidinyl) methyl]phenyl}methyl)-amino]-methyl}benzonitrile; [AC0105], p-{[({[p-(1-pyrrolidinyl)-methyl] phenyl}methyl)-amino]methyl}benzonitrile; [AC0102], (2,3-dihydro-1,4-benzodioxin-6-yl) [({[p-(dimethylamino) methyl]-phenyl}methyl)amino]methane; [AC0201], 3-[1-(benzylamino)-2-methylpropyl]benzaldehyde; [AC0202].

Ion-Mobility Mass Spectroscopy (IM-MS)

IM-MS was utilized to monitor the oligomerization of TDP-43307-319 in the presence of molecules AC0107, AC0105, AC0102 and AC0201. The ability of IMMS to separate species of a specific [m]z+ (m=mass, z=charge) that contains different [n]z+ (n=oligomer number) by measuring the arrival time distributions (ATDs) yields oligomeric distributions. Samples were prepared as mentioned previously and incubated at room temperature under quiescent conditions.

Results

The TDP-43307-319 WT peptide was dissolved in 10 mM ammonium acetate (pH 7.4) with 2% HFIP to a final peptide concentration of 100 μM. The sample was incubated at room temperature under quiescent conditions for 4 h to develop higher-order oligomers. Two dominant mass/charge (m/z) peaks were always present in the mass spectra corresponding to [n]Z+=[1]1+ and [1]2+. Charge state [1]2+ shows a single structure in its ATD, while [1]1+ exhibits oligomers ranging from dimers to octamers. The mass spectrum at 15 min showed well-resolved peaks, but after incubation at room temperature for 4 h, the signal-to-noise ratio (S/N) decreased and a raised baseline appeared, indicating aggregation. A freshly prepared sample at 15 min showed a dominant monomer and some dimer in the ATD of the [1]1+ peak. After incubation at room temperature for 4 h, the distribution shifted toward the higher-order oligomers. Experimental collision cross sections (CCS) showed little change, consistent with no conformational change throughout the incubation period. Once the presence of higher-order oligomers was confirmed, an inhibitor (either [AC0107], [AC0105], [AC0102], [AC0201] or [AC0202]) was added in a 1:1 peptide (100 μM): inhibitor (100 μM) molar ratio. Subsequent time points were taken to monitor the remodeling properties of the inhibitors.

Mass spectra after the addition of [AC0107] showed no complexation between the WT peptide and the molecule. This suggests that the interaction between the peptide and molecule is very short-lived and fairly weak. An increase in the signal-to-noise ratio and a reduction in the baseline were also observed, suggesting the level of aggregation was reduced, consistent with the strong reduction of the [1]1+ peak in the mass spectrum. Similar results were obtained for [AC0105], [AC0102], [AC0201] and [AC0202]. Treatment of the aggregated WT peptide with molecule [AC0107] demonstrated an initial increase in the number of higher-order oligomers. By ≥3 h, we see a redistribution to mostly monomer and dimer. We suspect the initial increase in the number of higher-order oligomers may be from larger species (not detectable with IMMS) beginning to dissociate into species that can now be observed with IM-MS. Upon addition of the inhibitor [AC0105] to aggregated WT, we see an immediate dissociation of higher-order oligomers into monomer and dimer. This distribution among the lower-order oligomers was maintained for a week after this single treatment. Drug [AC0102] worked at a slower rate compared to those of the other inhibitors. After the initial addition of [AC0102], a shift toward higher-order oligomers occurred (similar to the results with [AC0107]). After 1 h, remnants of higher-order oligomers are present. By later time points, we see a distribution more similar to that of the other two inhibitors, composed primarily of monomer and dimer.

The second-generation molecule [AC0201] immediately pushed the bulk of the distribution back to monomer, dimer, and trimer. At 3-24 h, the spectra were dominated by monomer and dimer. A week after this single treatment, a dominate monomer peak was observed, demonstrating that [AC0201] successfully redistributed the oligomers to monomer and was able to prevent the re-formation of higher-order oligomers. Recovery experiments with different concentrations of molecule [AC0201] were carried out to determine the lower limit of the drug's efficacy. The WT peptide concentration was maintained at 100 μM, and experiments were conducted at 50 μM (2:1), 25 μM (4:1), and 10 μM (10:1) [AC0201]. Results show that 2:1 and 4:1 molar ratios are effective at redistributing and maintaining the population of lower-order oligomers. A 10:1 ratio takes a longer time to dissociate oligomers to mostly monomer, but even at this concentration, [AC0201] is a very effective inhibitor.

Molecules [AC0107], [AC0105], and [AC0102] were all able to remodel the developed higher-order oligomers and prevent the re-formation of these toxically related species. [AC0201] demonstrated the fastest and most efficient redistribution among all of the molecules and was shown to be effective at a relative concentration ratio of 10:1.

The invention claimed is:

1. A method of treating a disease in a subject in need thereof, wherein the disease is caused by deposits of TDP-43 in the brain of the subject and is selected from the group consisting of sporadic amyotrophic lateral sclerosis, frontotemporal dementia, chronic traumatic encephalopathy, progressive supranuclear palsy, corticobasal degeneration, Parkinson's disease, Huntington's disease, limbic-predominant age-related TDP-43 encephalopathy, and motor neuron diseases, the method comprising administering to the subject a therapeutically effective amount of a compound, wherein the compound is one of:

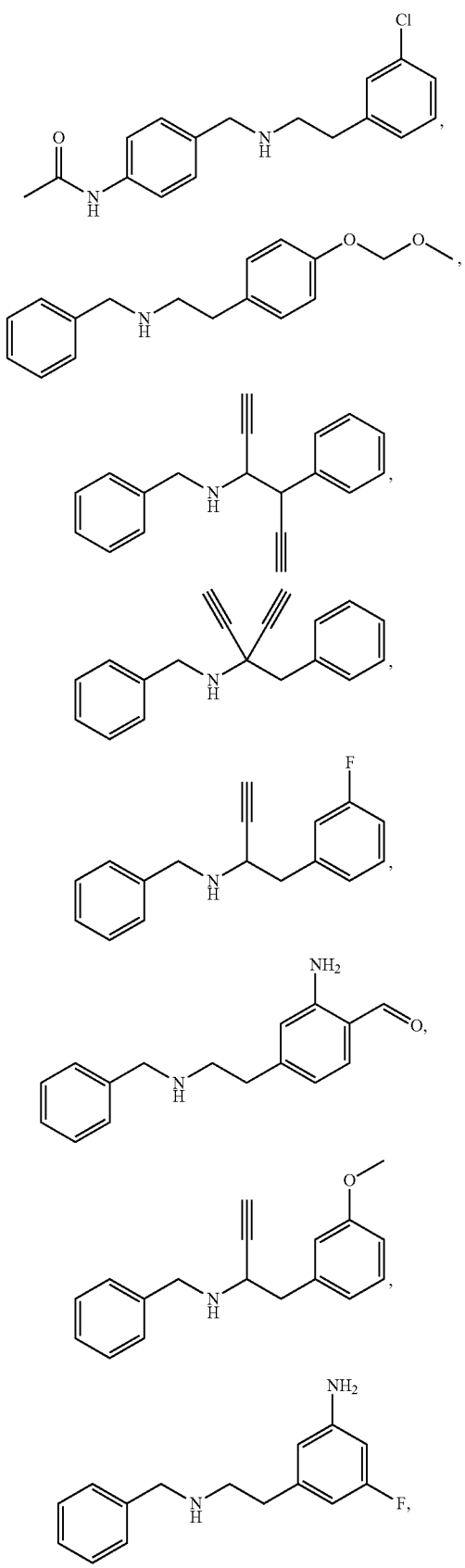

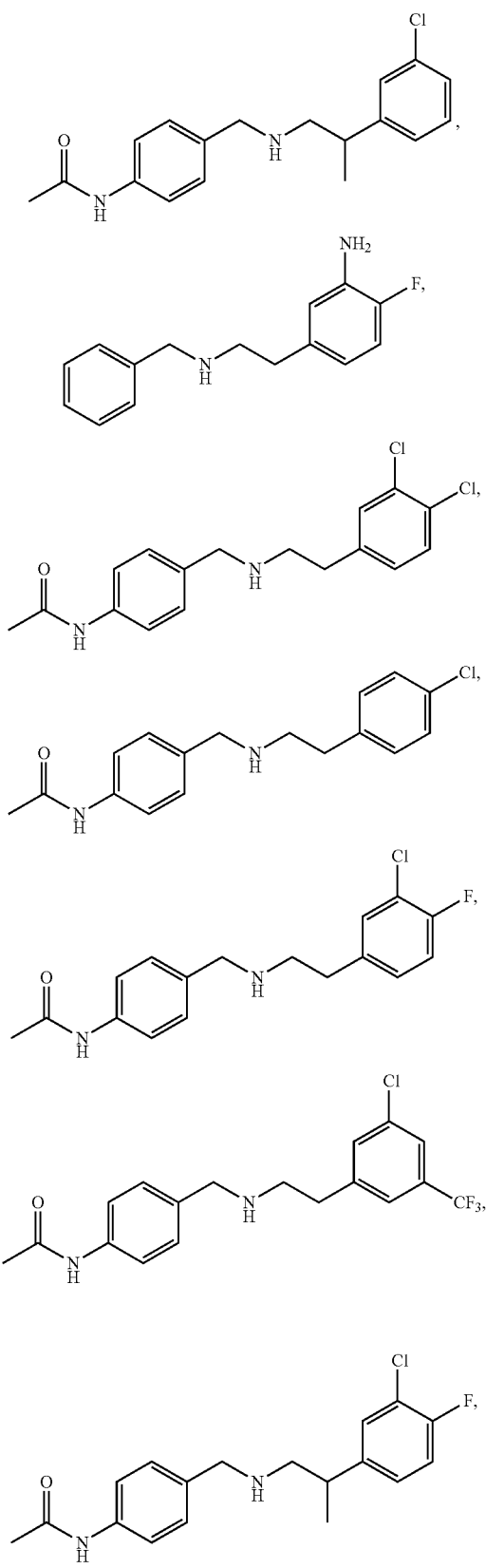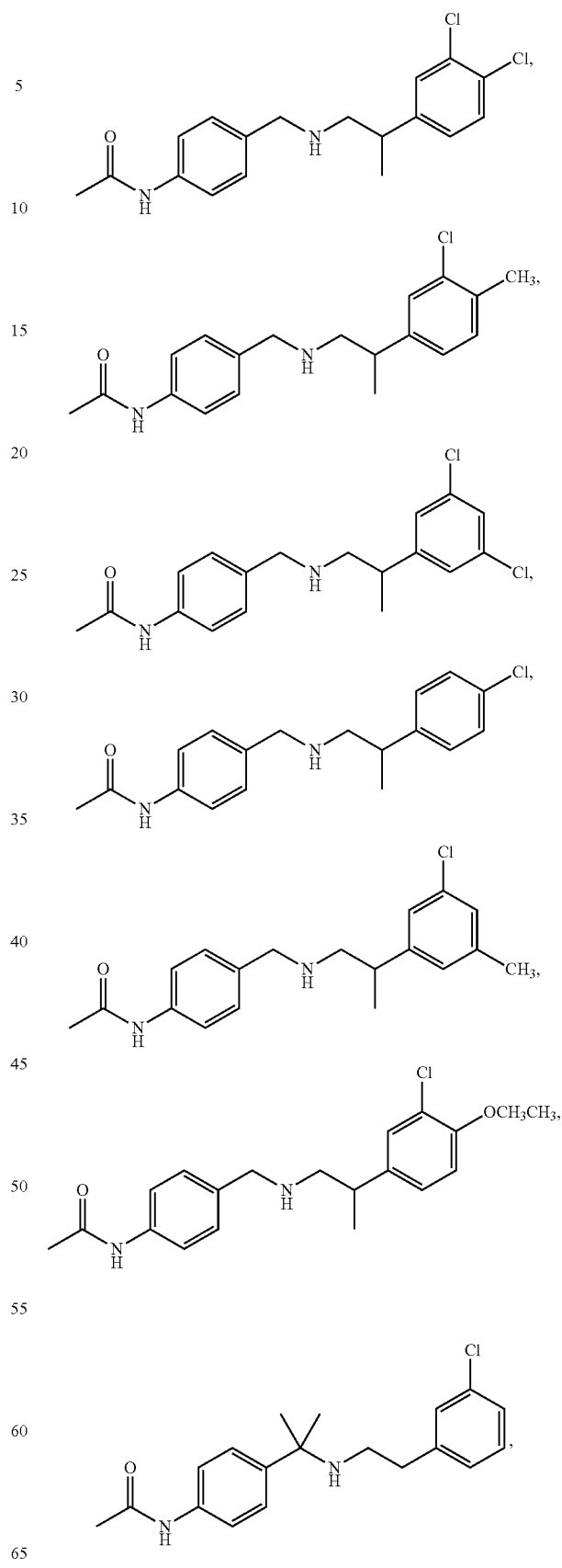

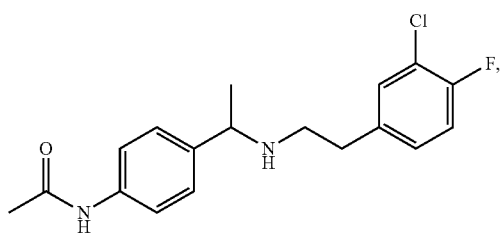

or a pharmaceutically acceptable salt of any of the foregoing.

2. The method of claim 1, wherein the compound is one of:

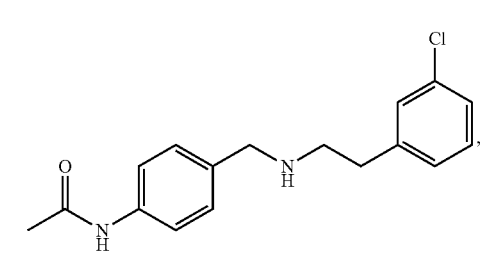

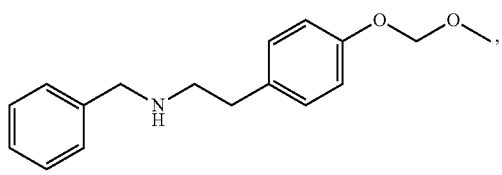

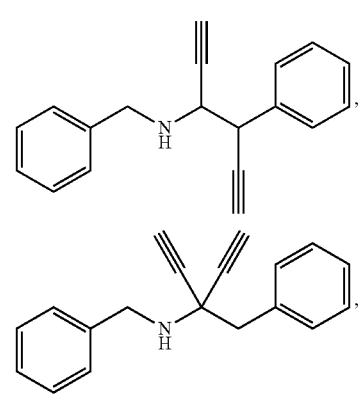

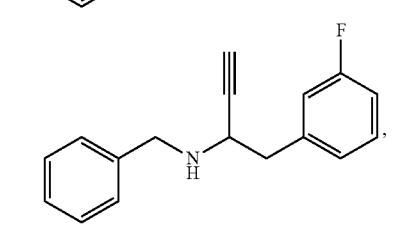

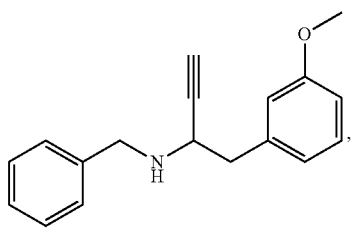

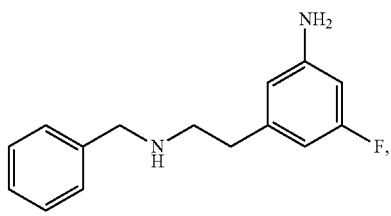

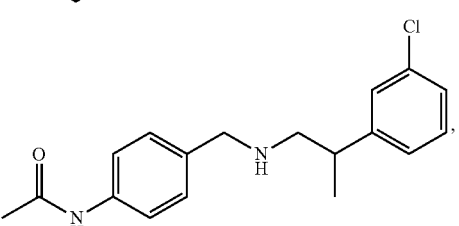

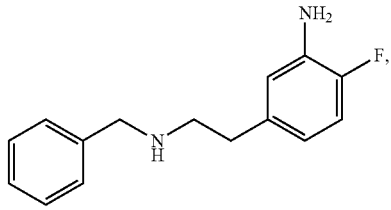

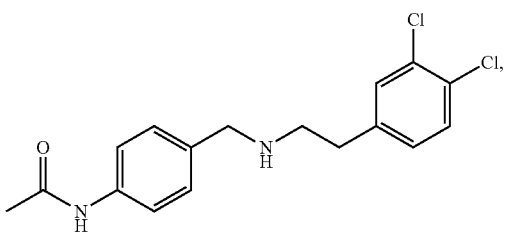

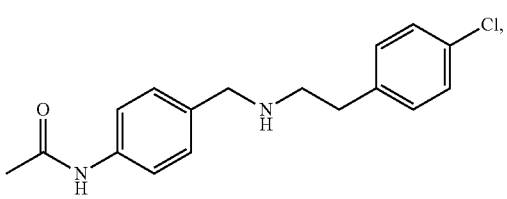

or a pharmaceutically acceptable salt of any of the foregoing.

3. A method of treating a disease in a subject in need thereof, wherein the disease is caused by deposits of TDP-43 in the brain of the subject and is selected from the group consisting of sporadic amyotrophic lateral sclerosis, frontotemporal dementia, chronic traumatic encephalopathy, progressive supranuclear palsy, corticobasal degeneration, Parkinson's disease, Huntington's disease, limbic-predominant age-related TDP-43 encephalopathy, and motor neuron diseases, the method comprising administering to the subject a therapeutically effective amount of a compound selected from the group consisting of

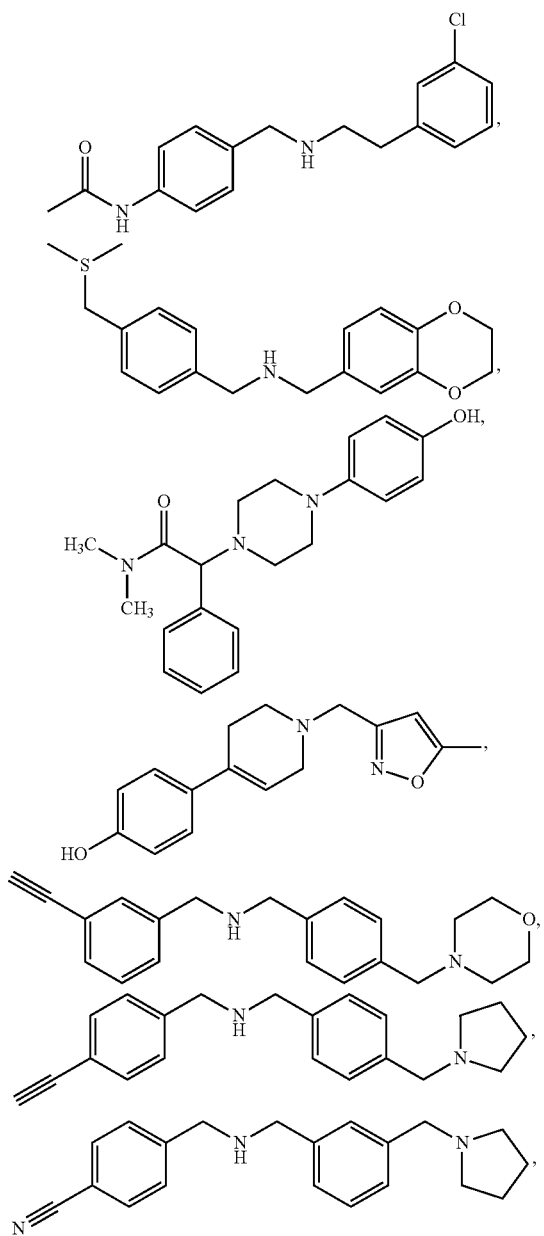
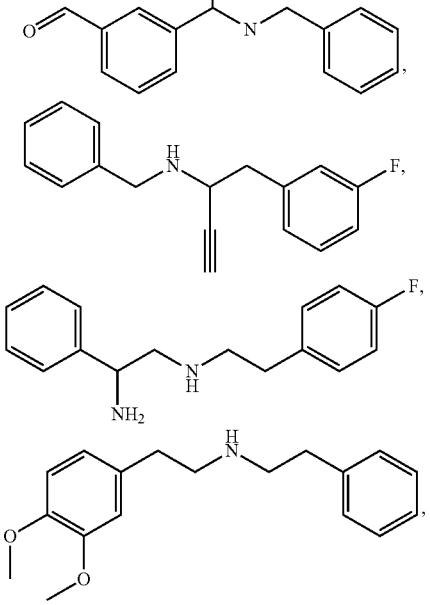
and a pharmaceutically acceptable salt of any of the foregoing.
4. The method of claim 3, wherein the subject has sporadic amyotrophic lateral sclerosis.
5. The method of claim 3, wherein the compound is:
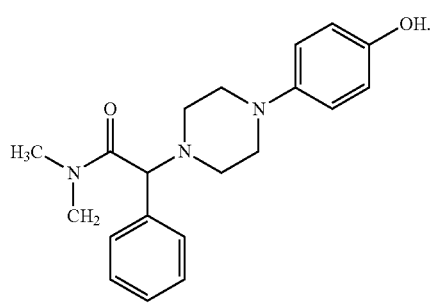 [SMILES: CN(C)C(=O)C(c1ccccc1)N1CCN(c2ccc(O)cc2)CC1]
* * * * *